US009422303B2

(12) United States Patent
Li et al.

(10) Patent No.: US 9,422,303 B2
(45) Date of Patent: Aug. 23, 2016

(54) FORMULATIONS OF WATER-INSOLUBLE CHEMICAL COMPOUNDS AND METHODS OF USING A FORMULATION OF COMPOUND FL118 FOR CANCER THERAPY

(75) Inventors: Fengzhi Li, Williamsville, NY (US); Xiang Ling, East Amherst, NY (US); Shousong Cao, East Amherst, NY (US)

(73) Assignee: Health Research, Inc., Buffalo, NY (US)

( * ) Notice: Subject to any disclaimer, the term of this patent is extended or adjusted under 35 U.S.C. 154(b) by 123 days.

(21) Appl. No.: 13/881,785

(22) PCT Filed: Oct. 31, 2011

(86) PCT No.: PCT/US2011/058558
§ 371 (c)(1),
(2), (4) Date: Nov. 18, 2013

(87) PCT Pub. No.: WO2012/058666
PCT Pub. Date: May 3, 2012

(65) Prior Publication Data
US 2014/0066470 A1 Mar. 6, 2014

Related U.S. Application Data

(60) Provisional application No. 61/407,996, filed on Oct. 29, 2010.

(51) Int. Cl.
| | | |
|---|---|---|
| A61K 31/695 | (2006.01) | |
| C07D 491/22 | (2006.01) | |
| A61K 31/475 | (2006.01) | |
| A61K 45/06 | (2006.01) | |
| A61K 47/10 | (2006.01) | |
| A61K 47/20 | (2006.01) | |
| A61K 47/40 | (2006.01) | |

(52) U.S. Cl.
CPC ............ *C07D 491/22* (2013.01); *A61K 31/475* (2013.01); *A61K 45/06* (2013.01); *A61K 47/10* (2013.01); *A61K 47/20* (2013.01); *A61K 47/40* (2013.01)

(58) Field of Classification Search
USPC .................................................. 514/63, 314
See application file for complete search history.

(56) References Cited

U.S. PATENT DOCUMENTS

| | | |
|---|---|---|
| 5,340,817 A | 8/1994 | Wall et al. |
| 6,653,319 B1 | 11/2003 | Xiang et al. |
| 2002/0142048 A1 | 10/2002 | Sands et al. |

FOREIGN PATENT DOCUMENTS

| | | |
|---|---|---|
| CN | 1446079 | 10/2003 |
| EP | 0556585 A1 | 8/1993 |
| WO | 0174401 A2 | 10/2001 |

OTHER PUBLICATIONS

Ling X, Cao S, Cheng Q, Keefe JT, Rustum YM, et al. (2012) A Novel Small Molecule FL118 That Selectively Inhibits Survivin, Mcl-1, XIAP and cIAP2 in a p53-Independent Manner, Shows Superior Antitumor Activity. PLoS ONE 7(9): e45571. doi:10.1371/journal.pone.0045571.*
Challa et al AAPS PharmSciTech 2005; 6 (2) Article 43.*
Rasheed et al Cyclodextrins as Drug Carriers Sci Pharm. 2008; 76; 567-598.*
Loftsson et al Expert Opin. Drug Deliv. (2005) 2(2): 335-351.*
Sharma U. S., et al., "Pharmaceutical and Physical Properties of Paclitaxel (Taxol) Complexes with Cyclodextrins," Journal of Pharmaceutical Sciences, vol. 84, No. 10, pp. 1223-1230. Oct. 1, 1995.
Adams, et al., "Camptothecin analogs with enhanced activity against human breast cancer cells. I. Correlation of potency with lipophilicity and persistence in the cleavage complex," Cancer Chemotherapy and Pharmacology, vol. 57, No. 2, pp. 135-144. Feb. 1, 2006.
Ma Xue-win, et al., Studies on the hydroxypropyl-B-cyclodextrin inclusion complexes of 10-hydroxycamptothecin, Chinese Journal of New Drugs, vol. 16, No. 17, pp. 1385-1387 (Sep. 8, 2007).
PubChem CID 437971, http://pubchem.ncbi.nlm.nih.gov/summary/summary.cgi?cid=437971, Create Date: Mar. 27, 2005, retrieved May 4, 2012.
Giovanella, et al. Science, 1989, vol. 246, p. 1046-1048.

* cited by examiner

*Primary Examiner* — Andrew D Kosar
*Assistant Examiner* — Raymond Covington
(74) *Attorney, Agent, or Firm* — Hodgson Russ LLP

(57) ABSTRACT

Provided are compositions, methods of making the compositions, and methods of using the compositions. The compositions can be provided as pharmaceutical preparations for use in disease treatment, such as cancer therapy. The compositions include novel pharmaceutical preparations which contain effective concentrations of a chemical compound. One compound used is 10H-1,3-Dioxolo[4,5-g]pyrano[3',4':6,7] indolizino[1,2-b]quinoline-8,11(7H,12H)-dione, 7-ethyl-7-hydroxy-, (S)-. The invention also provides methodologies for preparing pharmaceutical preparations for use in intravenous and oral pharmaceutical preparations that contain drug compounds that are difficult to dissolve in water.

11 Claims, 35 Drawing Sheets

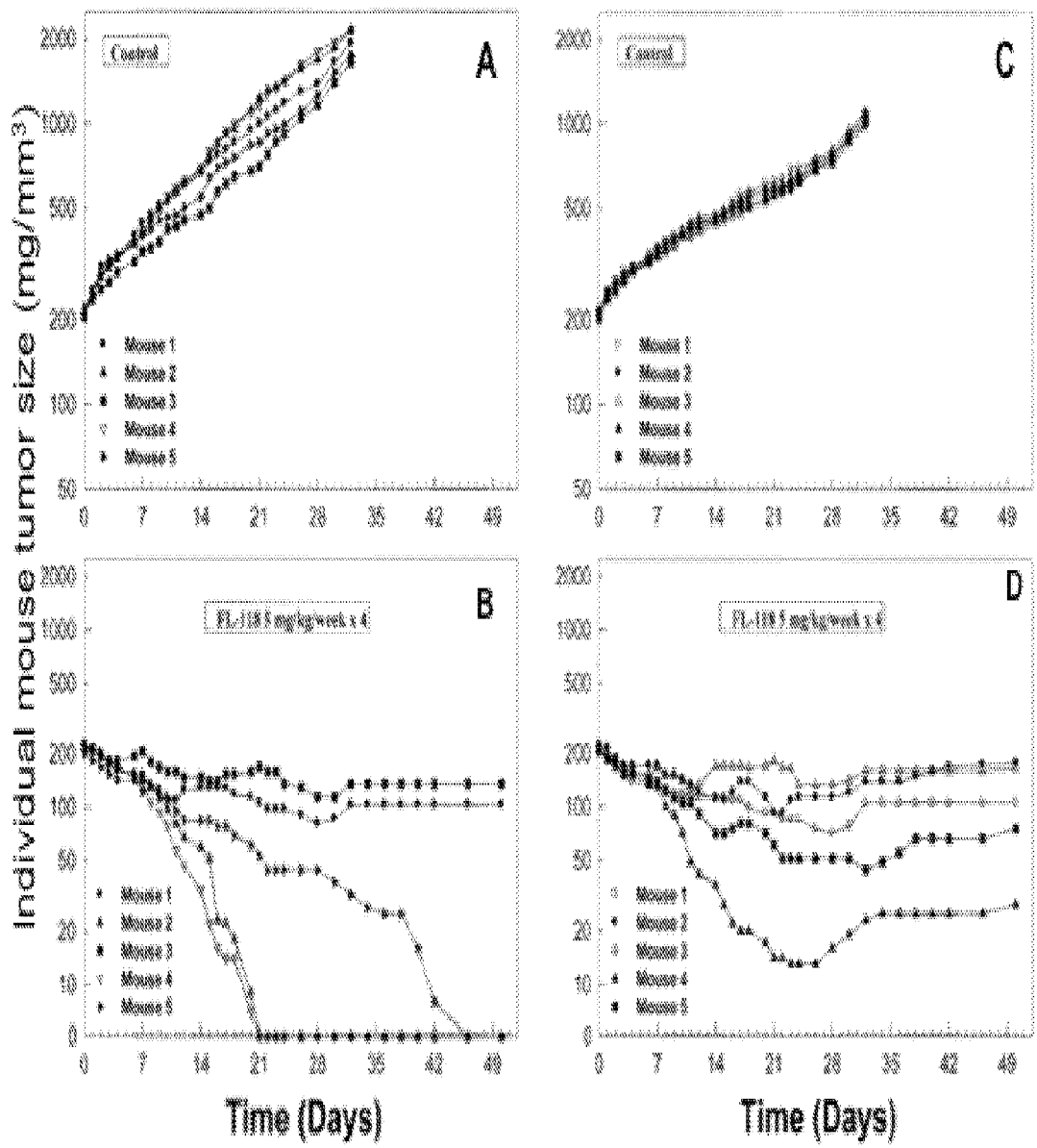

FORMULATIONS OF WATER-INSOLUBLE CHEMICAL COMPOUNDS AND METHODS OF USING A FORMULATION OF COMPOUND FL118 FOR CANCER THERAPY

CROSS-REFERENCE TO RELATED APPLICATION

This application claims priority to provisional application No. 61/407,996, filed on Oct. 29, 2010, the disclosure of which is incorporated by reference.

STATEMENT REGARDING FEDERALLY SPONSORED RESEARCH

This invention was made with government support under grant no. CA109481 from the National Cancer Institute. The government has certain rights in the invention.

FIELD OF THE INVENTION

The present invention related generally to compositions and methods for therapy of cancer.

BACKGROUND OF THE INVENTION

Anticancer efficacy and selectivity are two critical factors for successful anti-cancer treatment. The classical approach for anticancer drug discovery is the use of cytotoxicity as a drug selection marker. However, the drug candidates identified via this approach usually show little selectivity to cancer versus normal tissues. As a result, the selected compounds fail to be developed for use as anticancer drugs because of their high toxicity to normal cells and tissues. An additional challenge in anticancer drug discovery and development is that cytotoxicity-based screening of chemical compound libraries over the past several decades has derived overwhelming numbers of compounds that show inhibition of cancer cell growth in vitro. However, identification of compounds that can exhibit clinically relevant anti-cancer effect in relevant animal models has proven very difficult. Thus, there is an ongoing and unmet need to identify and develop existing compounds so that they can be used for inhibition of cancer growth in clinically relevant treatment modalities. The present invention meets these and other needs.

SUMMARY OF THE INVENTION

The present invention provides a method for inhibiting the growth of cancer in an individual. The method comprises administering to the individual a pharmaceutical preparation comprising an effective amount of 10H-1,3-Dioxolo[4,5-g]pyrano[3',4':6,7]indolizino[1,2-b]quinoline-8,11(7H,12H)-dione, 7-ethyl-7-hydroxy-, (S)- ("FL118"). Growth of the cancer in the individual is inhibited subsequent to the administration. The pharmaceutical preparations are suitable for administering to an individual using a wide variety of techniques, and are particularly useful for intravenous and/or oral administration. The pharmaceutical preparations provided by the invention comprise an aqueous solution, a cyclodextrin, and a polar aprotic solvent or an alcohol. They can further comprise helper cosolvents. The cyclodextrin in various embodiments is cyclodextrin (βCD), hydroxypropyl-β-cyclodextrin (HPβCD) sulfobutylether-β-cyclodextrin (SBE-βCD), or combinations thereof. In certain embodiments, the cyclodextrin is present as 0.125-2.5% of the formulation. The polar aprotic solvent can be present as 1-10% of the formulations. In one embodiment, the polar aprotic solvent is dimethyl sulfoxide (DMSO). In another embodiment, ethanol is included instead of the polar aprotic solvent. In certain embodiments, the pharmaceutical preparations of the invention include one or more additional anti-cancer agents, in addition to FL118.

The invention also provides a method for inhibiting cancer growth in an individual. The method comprises administering to the individual a pharmaceutical preparation that contains an effective amount of FL118. Preparations comprising various amounts of FL118 are disclosed herein, and include but are not necessarily limited to from 0.25-5.0 mg/ml FL118. Various dosage schedules and methods of providing a person suspected of having or diagnosed with cancer an effective amount of FL118 are also disclosed herein. Additionally, methods for using preparations of the invention with other anti-cancer agents in combination therapies are also provided.

The invention also provides strategies for preparing water-insoluble drug formulations for intravenous or oral administration. These methods generally comprise providing a Solvent A and a Solvent B, dissolving the Solvent A in the Solvent B to make a leading Solvent A/Solvent B mixture, and then dissolving a water-insoluble compound in the Solvent A/Solvent B mixture. These method are divided into Strategies I, II and III, which are explained in detail below.

Figure 5:
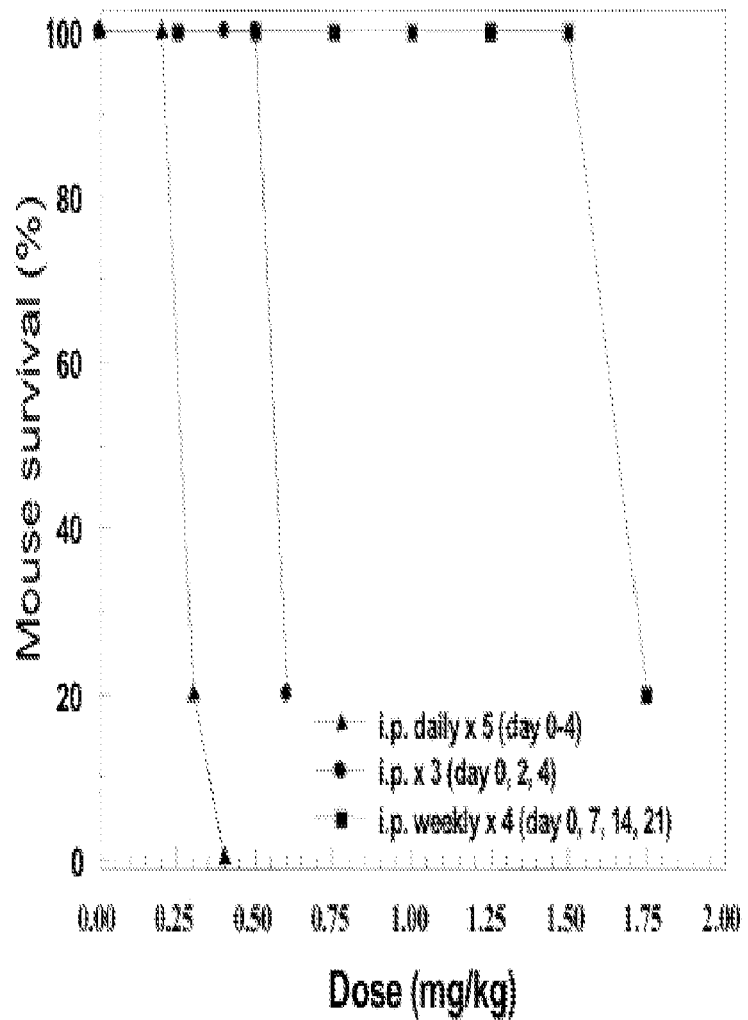

FIG. 5 A diagram of the dose response of FL118 in nude mice treated via i.p. routes at different doses and schedules. Routes and schedules are indicated.

Figure 6:
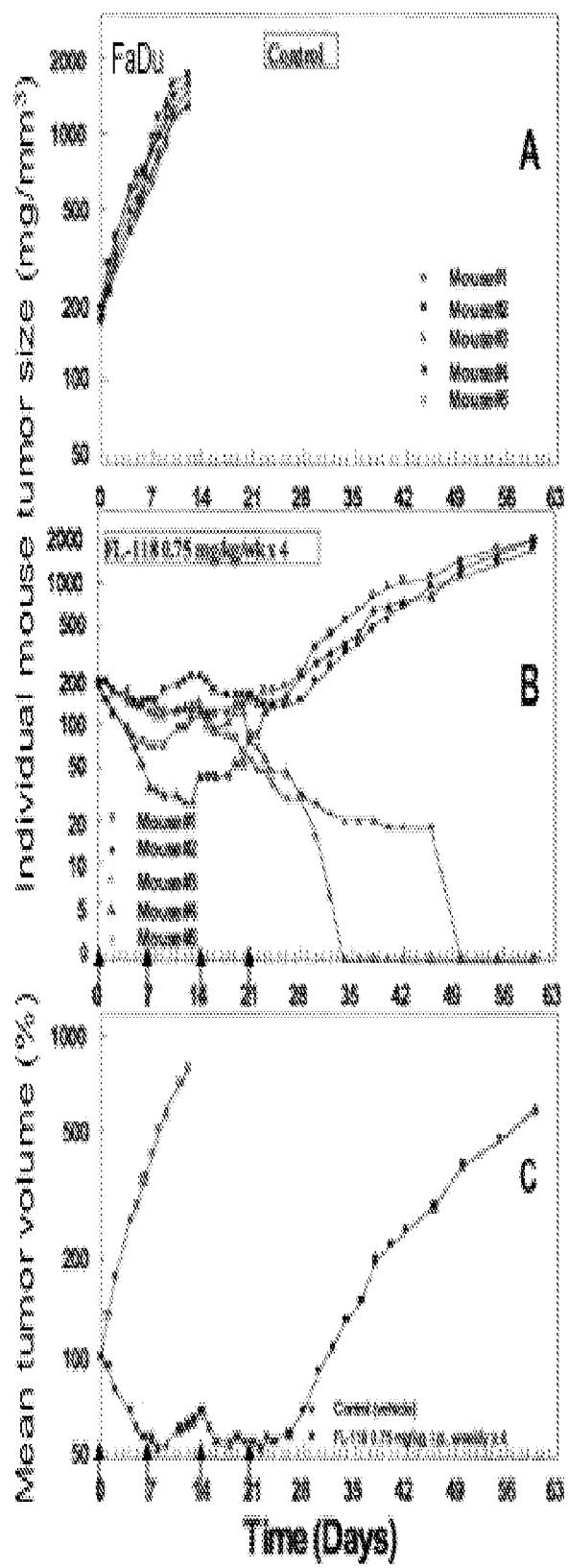

FIG. 6 is a representative experiment to show antitumor activity of FL118 on tumor in individual nude mice (B) or in an average of 5 mice (C) bearing FaDu (head and neck cancer) xenografts. FL118 was administered via i.p. once a week for 4 weeks at a dose of 0.75 mg/kg (50% MTD). Treatment was initiated 7 days after tumor implantation, which was designated as Day 0 (tumor weight is ~200-250 mg/mm³ at the time of treatment). Control mice were administered the same volume of vehicle solution and were euthanized on Day 12 due to large tumor masses (A).

Figure 7:
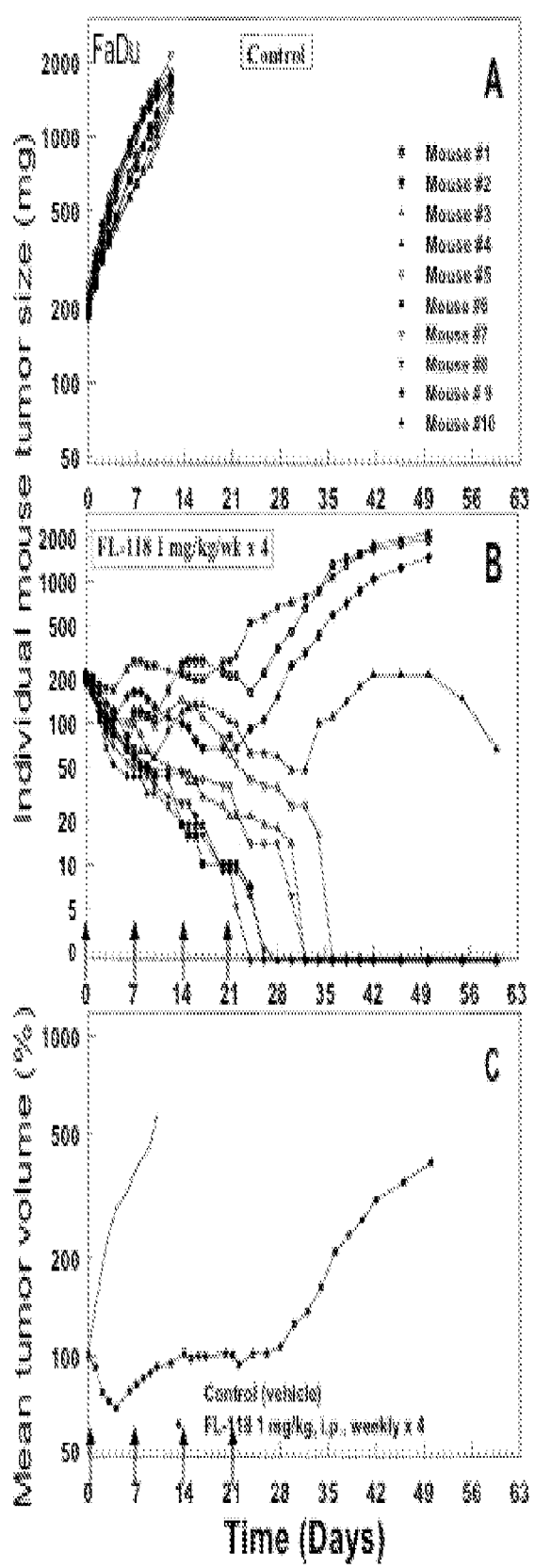

FIG. 7 is a representative experiment to show antitumor activity of FL118 at a dose of 1 mg/kg (a dose under MTD) on tumor in individual nude mice (B) or in an average of 10 mice (C) bearing FaDu xenografts. Other conditions are the same as described in FIG. 6. Control mice were administered the same volume of vehicle solution and were euthanized on Day 12 due to large tumor masses (A)

Figure 8:
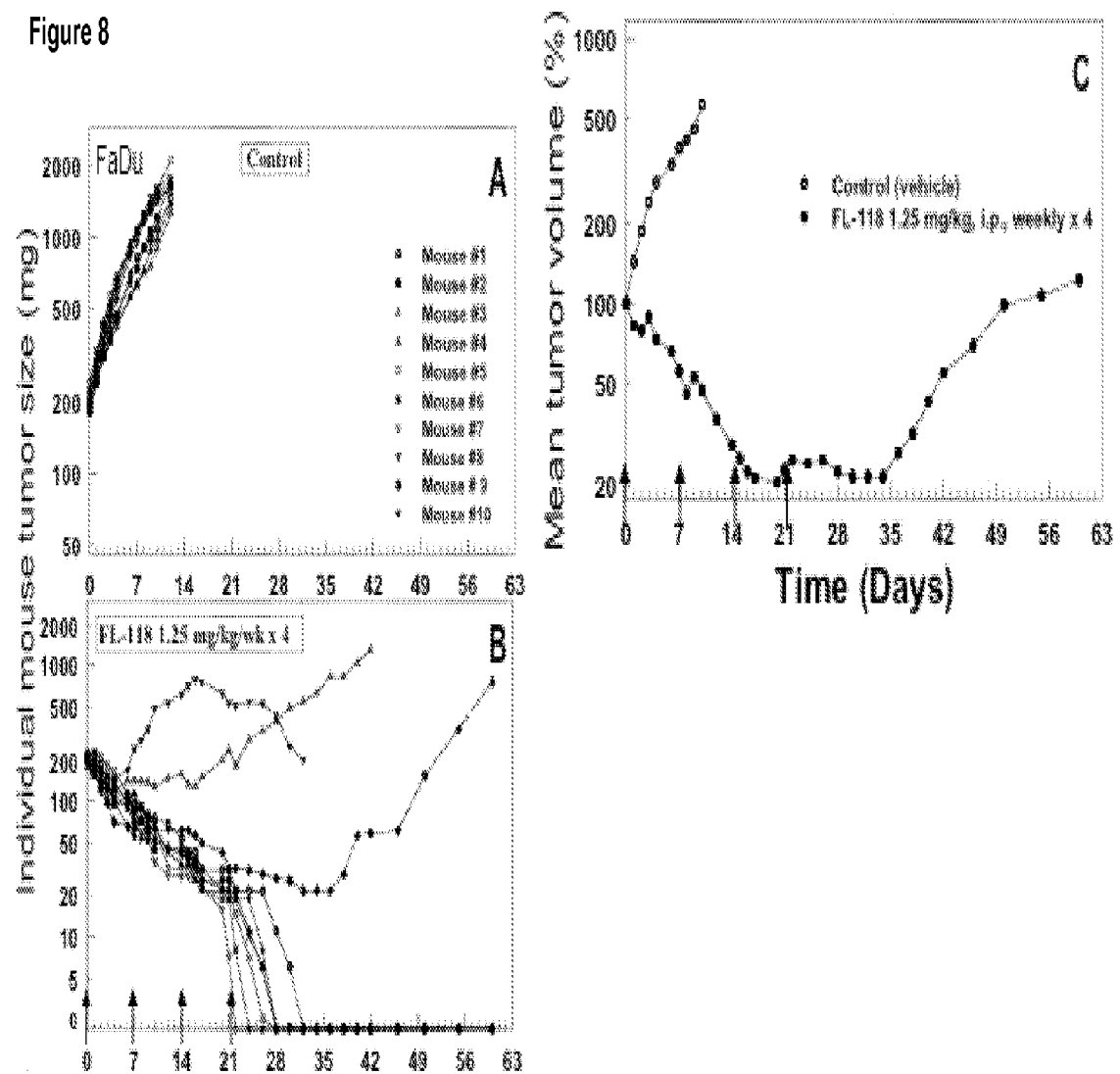

FIG. 8 is a representative experiment to show individual FaDu tumors in responses to vehicle control (A) or FL118 1.25 mg/kg (B). Other conditions are the same as described in FIG. 6. The average tumor growth inhibition from 10 individual tumor-bearing mice showed in B is presented in C.

Figure 9:
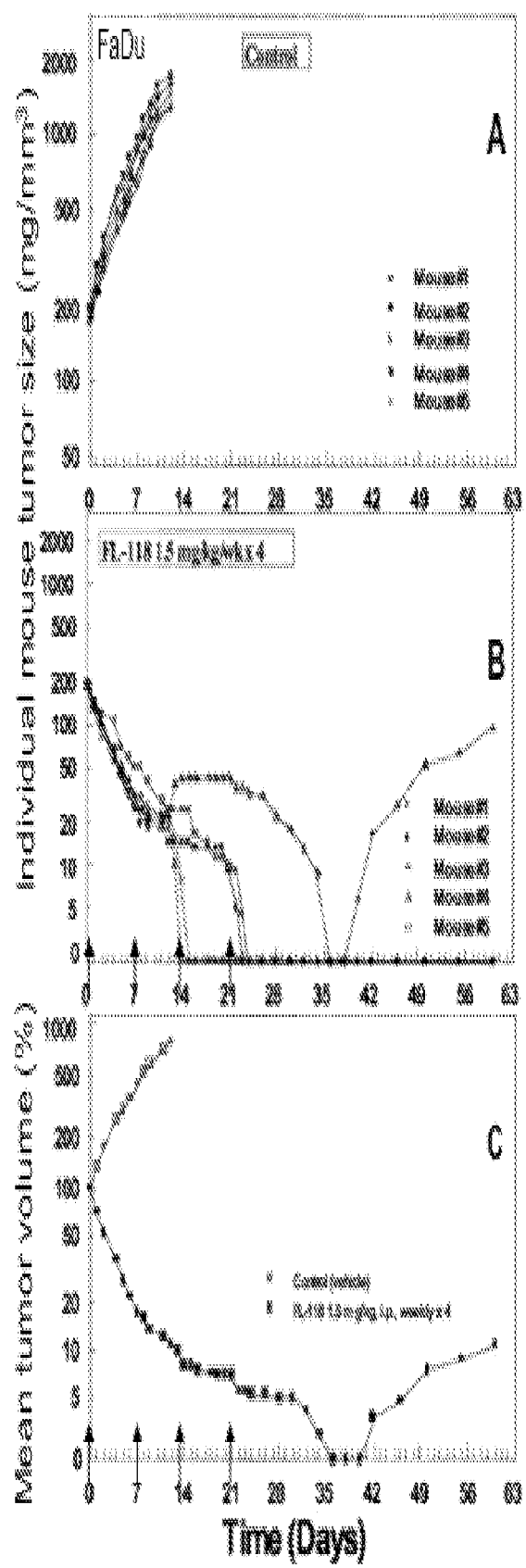

FIG. 9 is a representative experiment to show individual FaDu tumors in response to vehicle control (A) or FL118 1.5 mg/kg (MTD, B). Other conditions are the same as described in FIG. 6. The tumor growth inhibition in 5 individual tumor-bearing mice is shown in B. The average tumor growth inhibition from 5 individual mice is shown in C.

Figure 10:
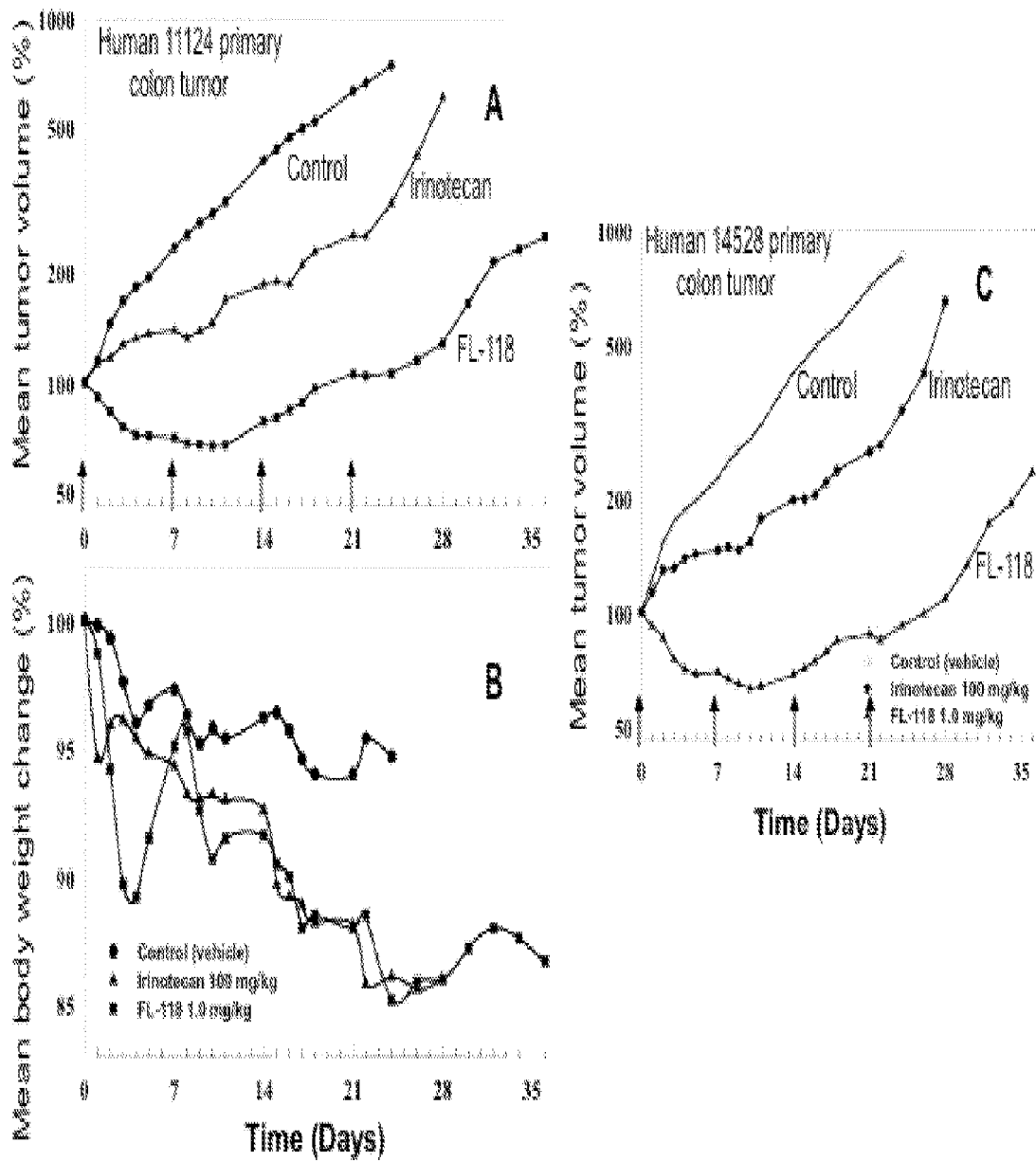

FIG. 10 Antitumor activity (A & C) and toxicity (body weight loss, B) of FL118 and irinotecan in SCID mice bearing human colon primary tumors, 11124 (A) and 14528 (C) are shown. FL118 was administered via i.p. at 1 mg/kg and was administered via i.p. at irinotecan 100 mg/kg (MTD) once a week for 4 weeks as indicated by arrows. Treatment was initiated 7 days after tumor implantation on Day 0 (tumor weight is ~200-250 mg/mm³ at the time of treatment).

Figure 11:
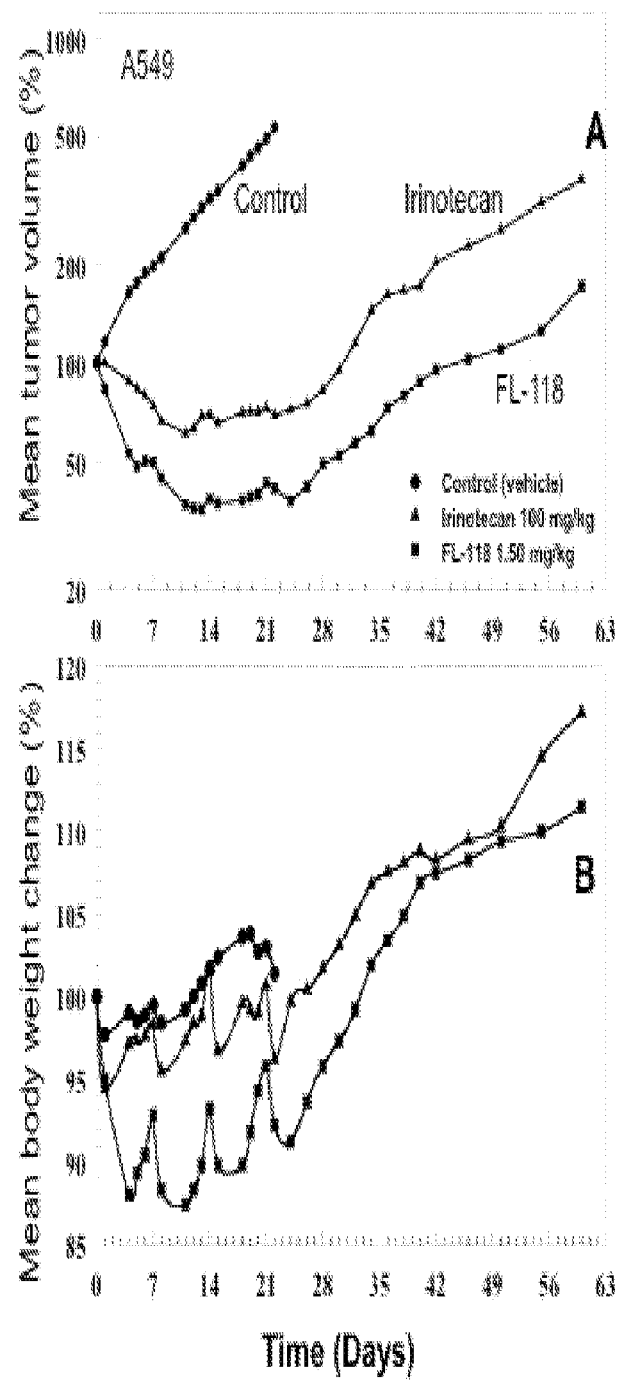

FIG. 11 is a representative experiment to compare antitumor activity (A) and toxicity (body weight loss, (B) of FL118 with irinotecan at their MTD in nude mice bearing A549 lung tumor xenografts. Drugs were administered via i.p. once a week for 4 weeks at their MTD as shown. Treatment was initiated 7 days after tumor implantation on Day 0 (tumor weight ~200-250 mg/mm³ at the time of treatment).

Figure 12:
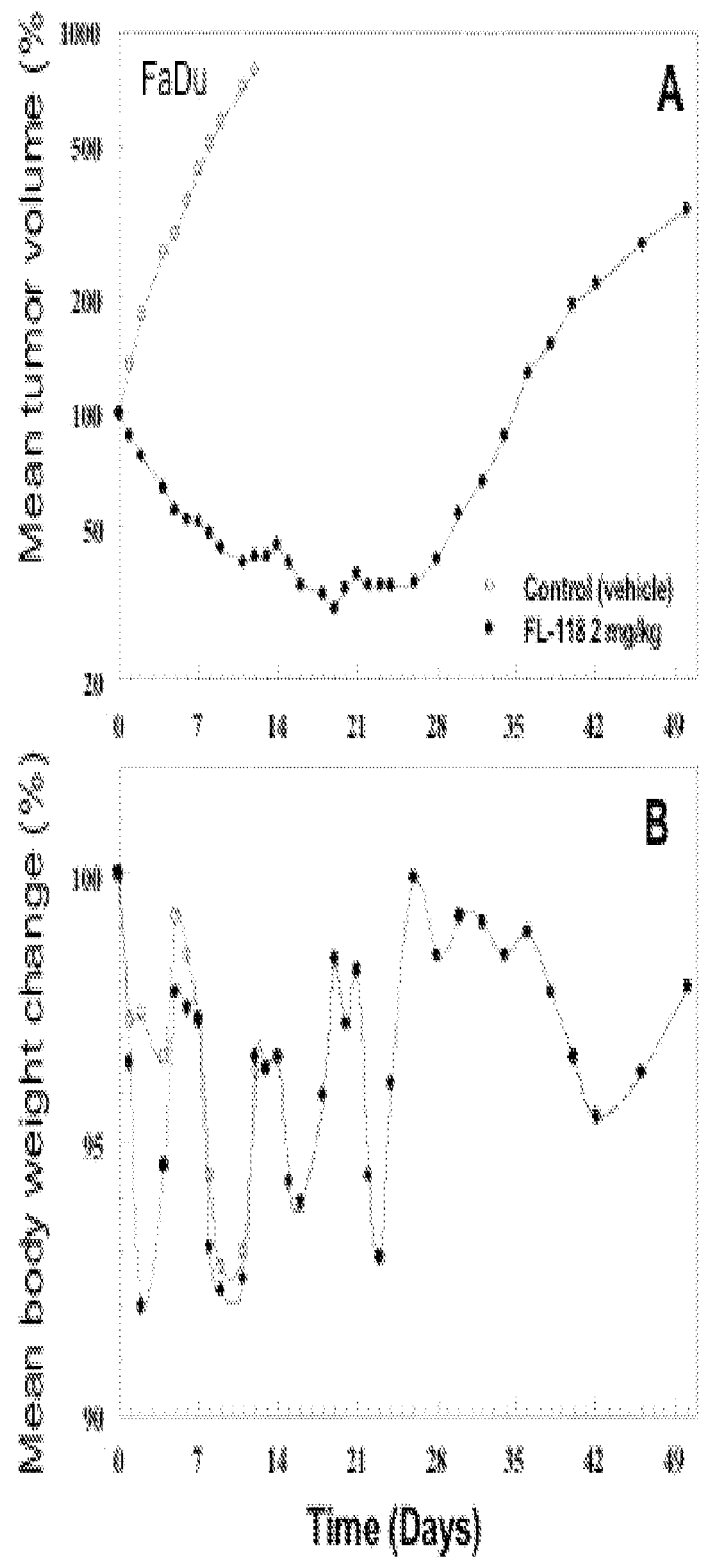

FIG. 12 Antitumor activity (A) and toxicity (B) of FL118 via the p.o. (oral/orally) route in nude mice bearing FaDu head & neck tumor xenografts. Drugs were administered per oral (p.o.) once a week for 4 weeks at a dose of 2 mg/kg. Treatment was initiated 7 days after xenograft tumor implantation on Day 0 (tumor weight ~200-250 mg/mm³ at the time of treatment).

Figure 13:
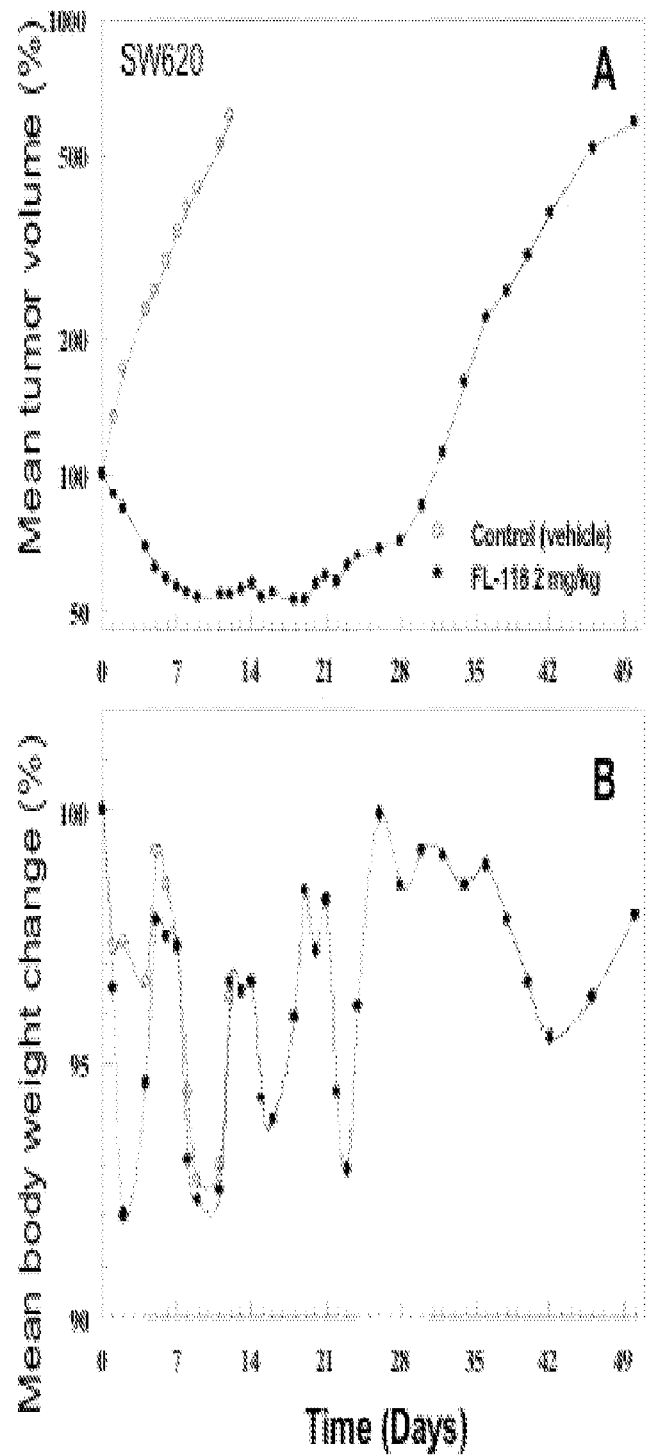

FIG. 13 Antitumor activity (A) and toxicity (body weight loss, B) of FL118 via p.o. in nude mice bearing human SW620 colon tumor xenografts. The experimental conditions and procedure are the same as in FIG. 12.

Figure 14:
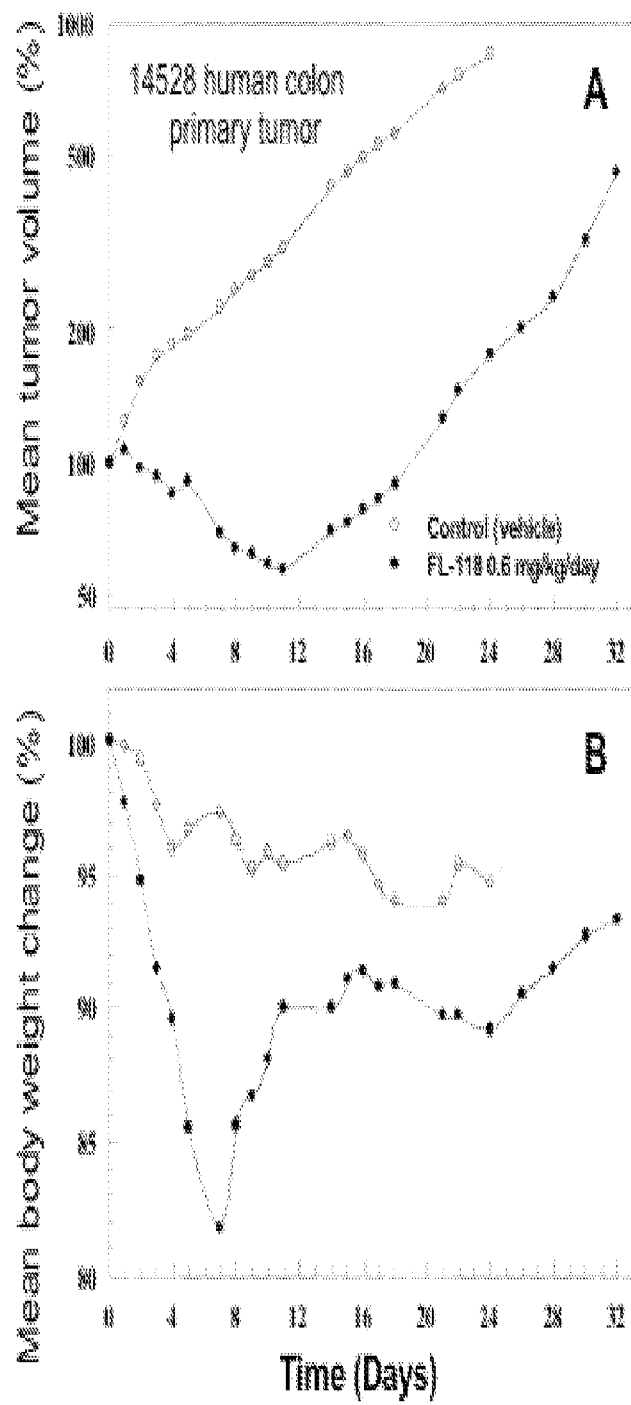

FIG. 14 Antitumor activity (A) and toxicity (body weight loss, B) of FL118 in SCID mice bearing the 14528 human primary colon cancer xenografts. FL118 (0.6 mg/kg) and vehicle control were administered via p.o. once a day for 5 days. Other conditions are the same as described in FIG. 12.

Figure 15:
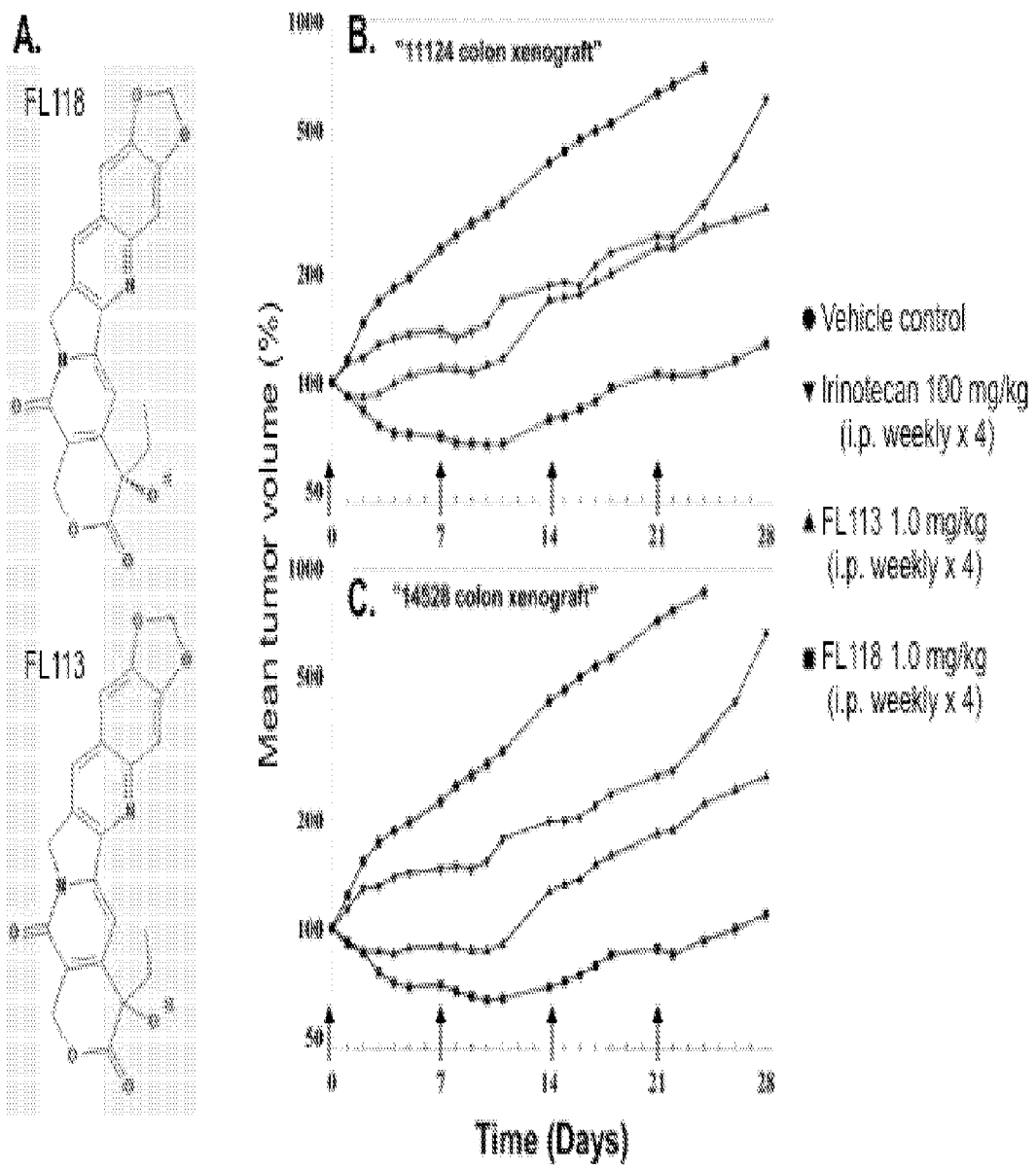

FIG. 15 A. Comparison of the steric structure of FL118 with FL113: The molecular weight for FL118 and FL113 is the same (MW=392). The difference between FL118 and FL113 is the steric conformation of the hydroxyl group (—OH). The "—OH" in FL118 is in the S position, while the "—OH" in FL113 is half in the S position and half in the R position. The name reflecting this difference in the chemical structure of the two compound is "10,11-Methylenedioxy-20S-camptothecin" for FL118 and is "10,11-methylenedioxy-20(RS)-camptothecin" for FL113. B and C. Comparison of the in vivo antitumor efficacy for FL113 and FL118 versus irinotecan: The SCID mouse models of human primary colon cancer xenografts were used for evaluating the relative antitumor activity for FL113 and FL118 versus irinotecan (control). Two human colon cancer tissues [11124 (B) and 14528 (C) originally from anonymous colon cancer patients) were used in the experiment. Drug treatment was conducted with the clinically relevant schedule of irinotecan (weekly×4) indicated by arrows. The initial drug treatment was designated Day 0, and the treatment was initiated 7 days after subcutaneous tumor implantation, on which tumor weight is about 200-250 mg. The tumor curve in each treatment condition is the mean derived from five tumors.

Figure 16:
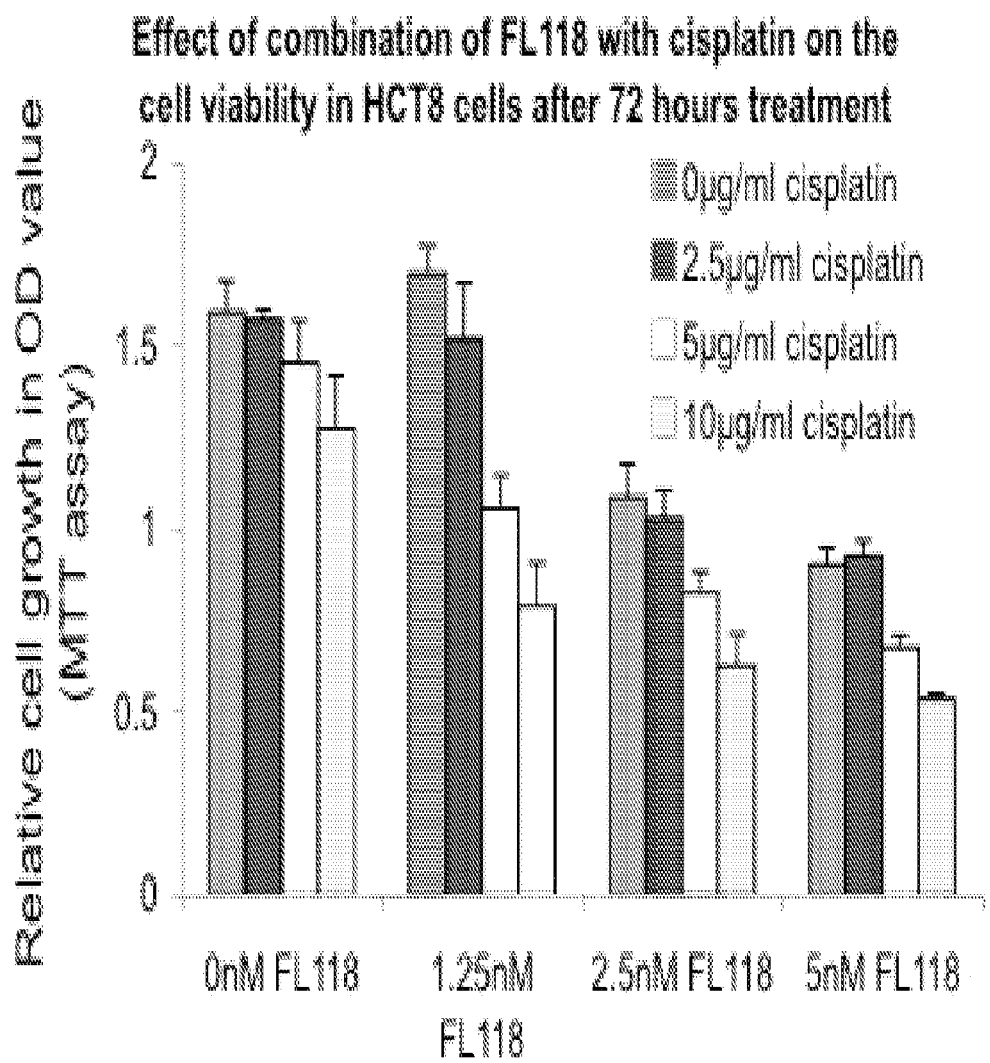

FIG. 16 A representative experiment to show the effect of FL118 in combination with cisplatin on HCT-8 colon cancer cells. Cells were grown in complete medium with serum to about 50% confluence and then treated with FL118 and cisplatin in a series of concentrations alone and in combination as shown. Cell growth and viability were determined by MTT assay 72 hours after treatment. Relative cell growth in OD values was presented in histogram. Each bar is the mean±SD derived from three independent parallel treatments.

Figure 17:
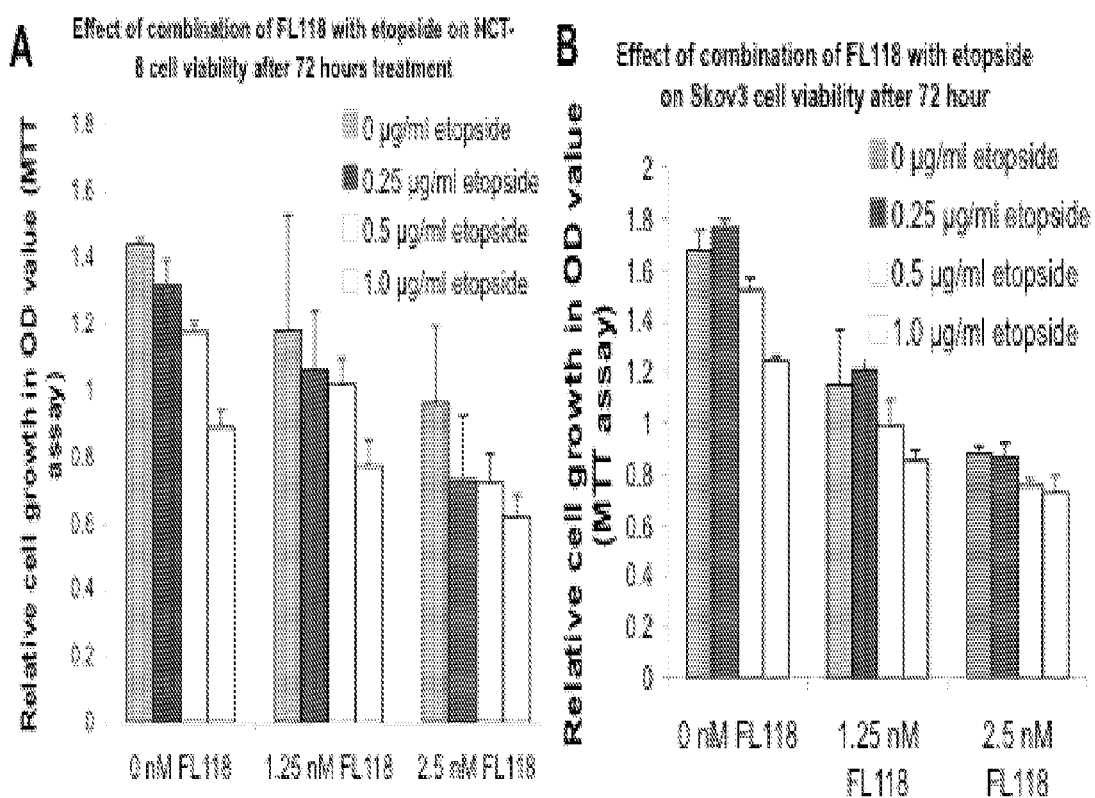

FIG. 17 Representative experiments to show the effect of FL118 in combination with etoposide on HCT-8 colon (A) and Skov3 ovarian (B) cancer cell growth: Cells were grown in complete medium with serum to 50% confluence. Cells were treated with FL118 and etoposide alone and in combination as shown. Cell growth and viability were determined using MTT assay 72 hours post treatment. Relative cell growth in OD values was presented in histogram. Each bar is the mean±SD derived from 3 independent treatments.

Figure 18:
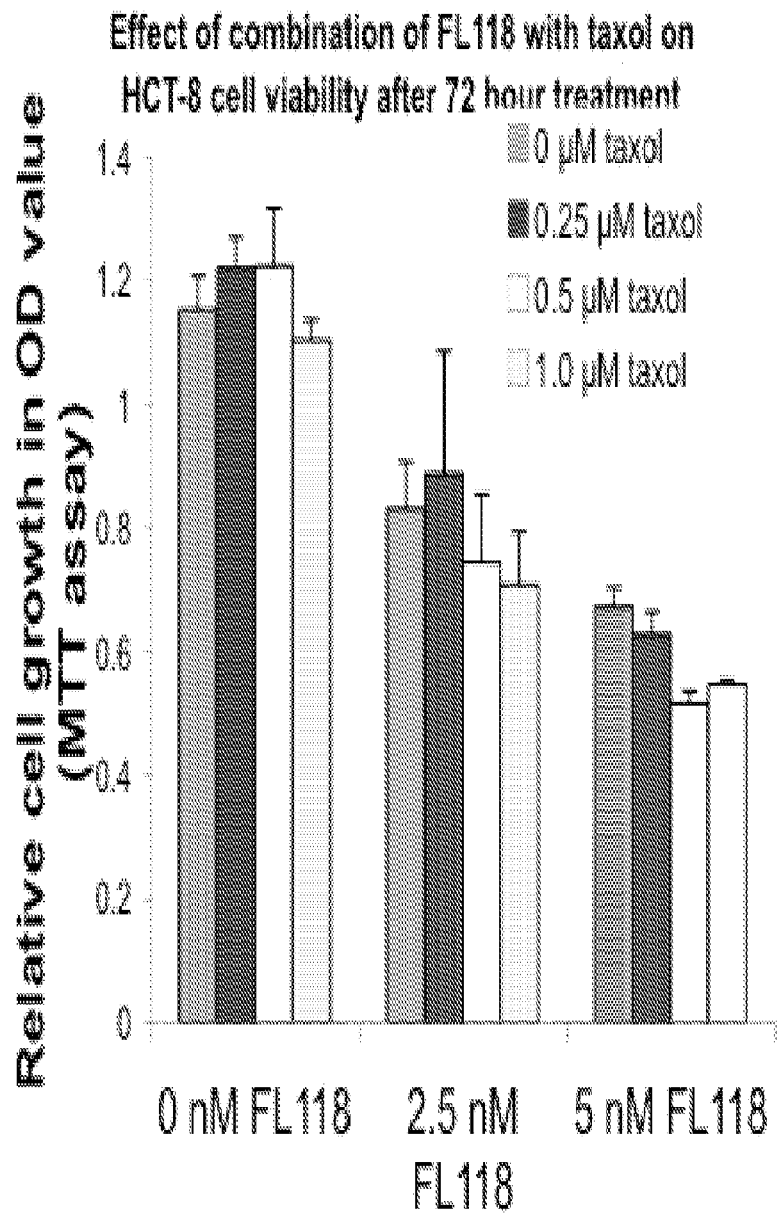

FIG. 18 A representative experiment for demonstration of the effect of FL118 in combination with taxol on HCT-8 colon cancer cell growth: Cells cultured in complete medium with serum were grown to 50% confluence. Cells were treated with FL118 and taxol alone and in combination as shown. Cell growth and viability were determined using MTT assay 72 hours post treatment. Relative cell growth in OD values was presented in histogram. Each bar is the mean±SD derived from 3 independent treatments.

Figure 19:
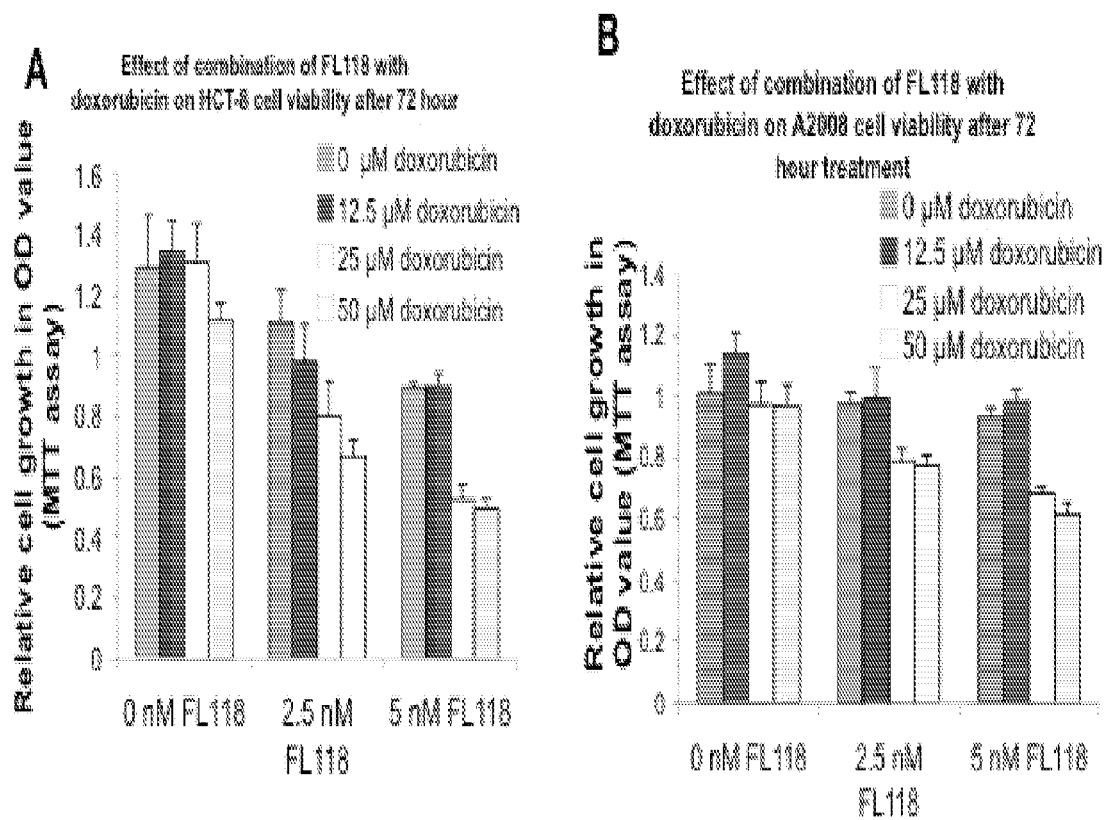

FIG. 19 Representative experiments to show the effect of FL118 in combination with doxorubicin on HCT-8 colon (A) and A2008 ovarian (B) cancer cell growth: Cells were grown in complete medium with serum. Cells were treated with FL118 and doxorubicin alone and in combination as shown when reaching to 50% confluence. Cell growth and viability were determined using MTT assay 72 hours post treatment. Relative cell growth in OD values was presented in histogram. Each bar is the mean±SD derived from 3 independent treatments.

Figure 20:
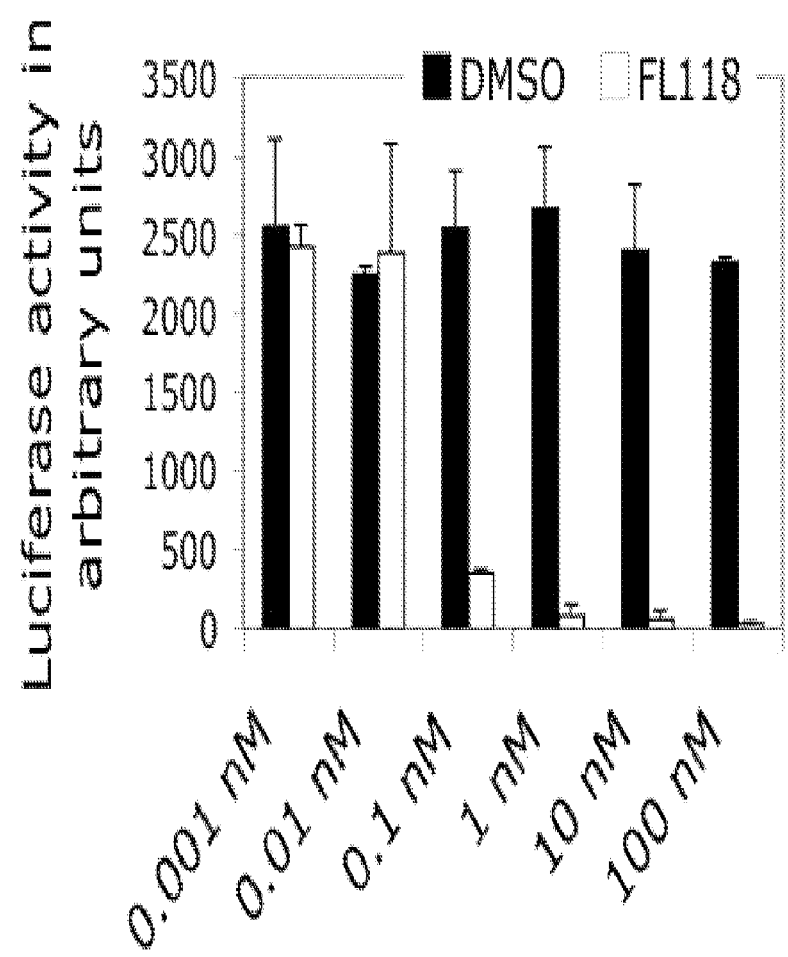

FIG. 20 is a representation of the effect of FL118 on human survivin promoter-driven luciferase activity in ovarian cancer cells. A2008 ovarian cancer cells that stably express human survivin promoter (6309 bp)-driven luciferase reporter gene were treated with FL118 in a series of concentration as shown. Cells were lysed 24 hours post treatment, followed by measuring luciferase activity using luciferase assay system from Promega. Data were plotted in histogram from data derived from 3 independent testing wells of a representative experiment.

Figure 21:
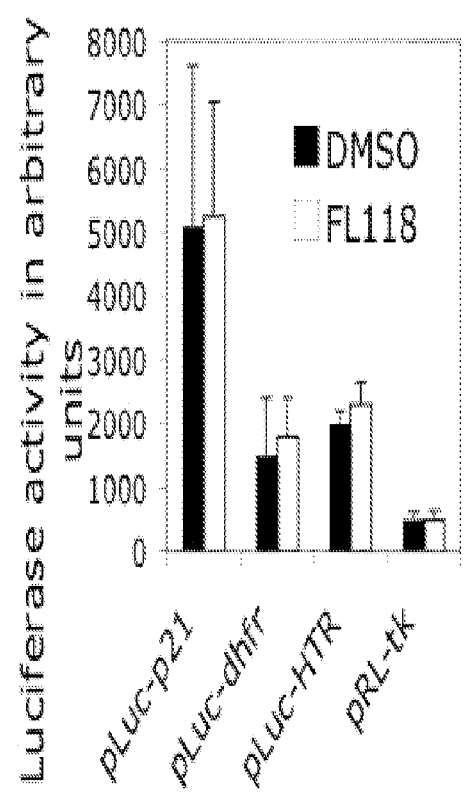
Figure 21:
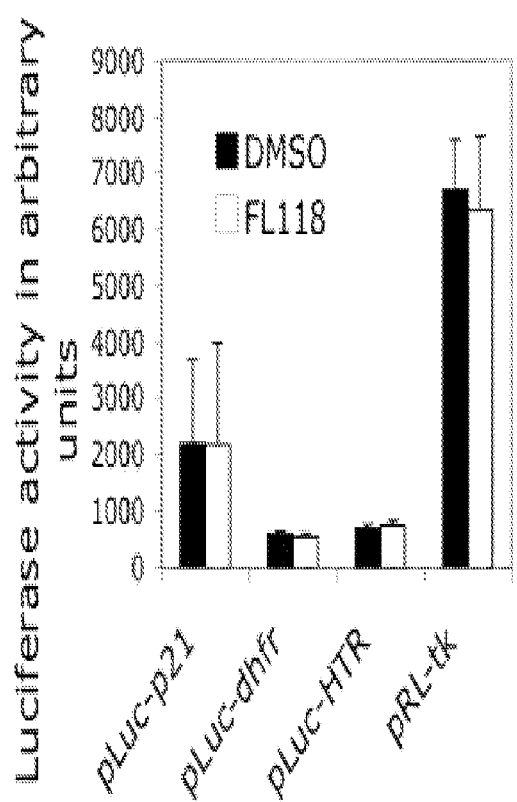

FIG. 21 Representative data to show the specificity of FL118 downregulation of survivin promoter activity but not other promoter activity. A. EKVX lung cancer cells. B. LNCaP prostate cancer cells. Cells were transfected with luciferase reporter vectors driven by a gene promoter from cyclin-dependent kinase inhibitor p21, dehydrofolate reductase (DHFR), human thrombin receptor (HTR) or thymidine kinase (TK). Cells were treated with FL118 at 10 nM 16 hours after transfection. Cells were lysed 24 hours after FL118 treatment, followed by measuring luciferase activity. Data (mean±SD) were plotted in histogram from data derived from 3 independent testing wells of a representative experiment.

Figure 22:
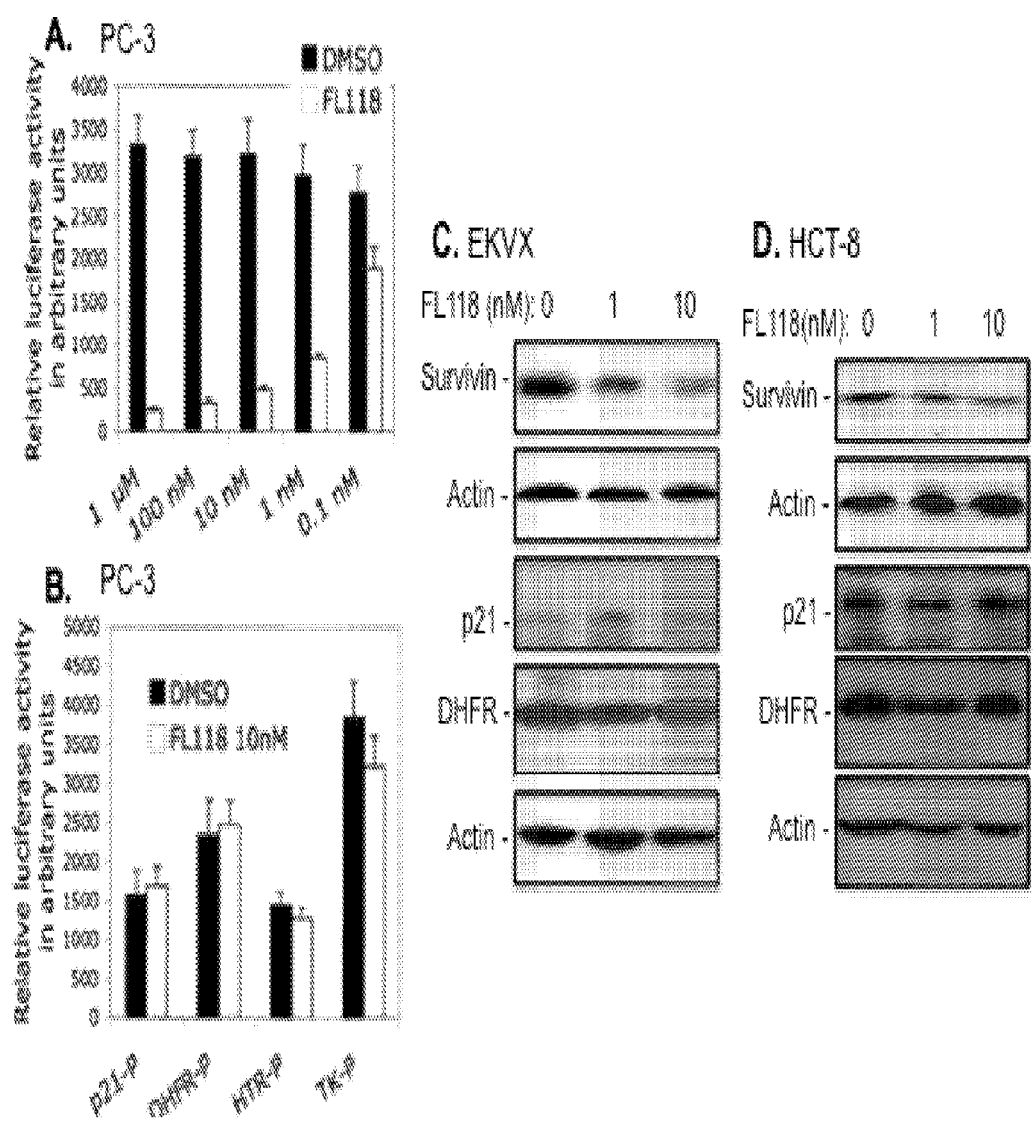

FIG. 22 Representative data to show selective inhibition of survivin promoter activity and endogenous relevant gene expression by FL118: A. PC-3 prostate cancer cells that stably express survivin promoter (6309 bp)-luciferase construct were treated with FL118 at different concentration. Luciferase activity was measured 24 hours after treatment. B. PC-3 cells were transfected with luciferase constructs driven by a gene promoter from p21, DHFR, HTR or TK genes, respectively, followed by FL118 treatment and luciferase activity assay at the same condition as in A. Each bar is the mean±SD from data derived from 3 independent testing wells of a representative experiment. C and D. FL118 inhibits endogenous survivin expression but not the expression of endogenous p21 and DHFR. Subconfluent EKVX and HCT-8 cells were treated with and without FL118 for 24 hours as shown. Cells were then lysed and the expression of survivin, p21 and DHFR was analyzed by western blots with their corresponding antibodies. Actin expression was used as internal controls.

Figure 23:
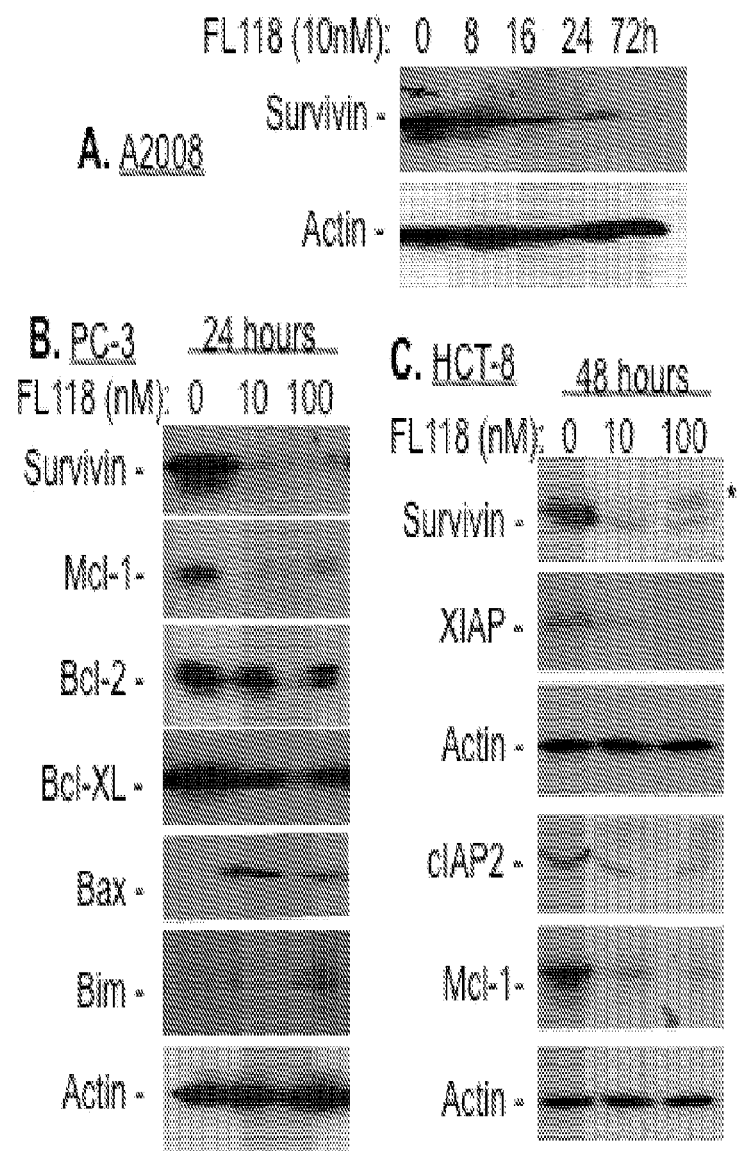

FIG. 23 Representative data to show the differential modulation of IAP/Bcl-2 family protein expression by FL118: Sub-confluent cells were treated with and without FL118 as shown. Cells were then lysed and analyzed by western blots using relevant antibodies. A. Time course for FL118 inhibition of survivin expression in A2008 ovarian cancer cells. B. Differential modulation of antiapoptotic and proapoptotic protein expression by FL118 in PC-3 prostate cancer cells. C. Downregulation of survivin, XIAP, cIAP2 and Mcl-1 by FL118 in HCT-8 colon cancer cells. Of note, the "*" in C marks the potential expression of the proapoptotic protein survivin-2B induced by FL118. Representative actin expression is shown as internal controls.

Figure 24:
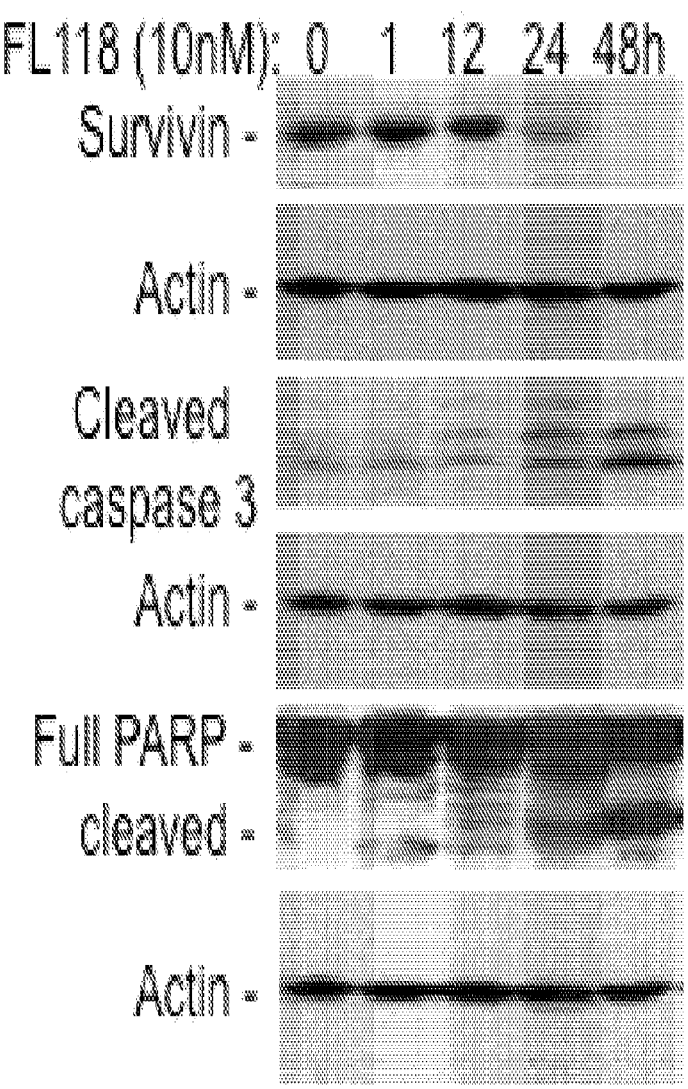

FIG. 24 Representative data to show that FL118-mediated inhibition of survivin and other antiapoptotic proteins is associated with caspase 3 activation and PARP cleavage, hallmarks of apoptosis: HCT-8 colon cancer cells at sub-confluence were treated with and without FL118 as shown, followed by cell lysis and western blot analysis with relevant antibodies. Actin is the internal control.

Figure 25:
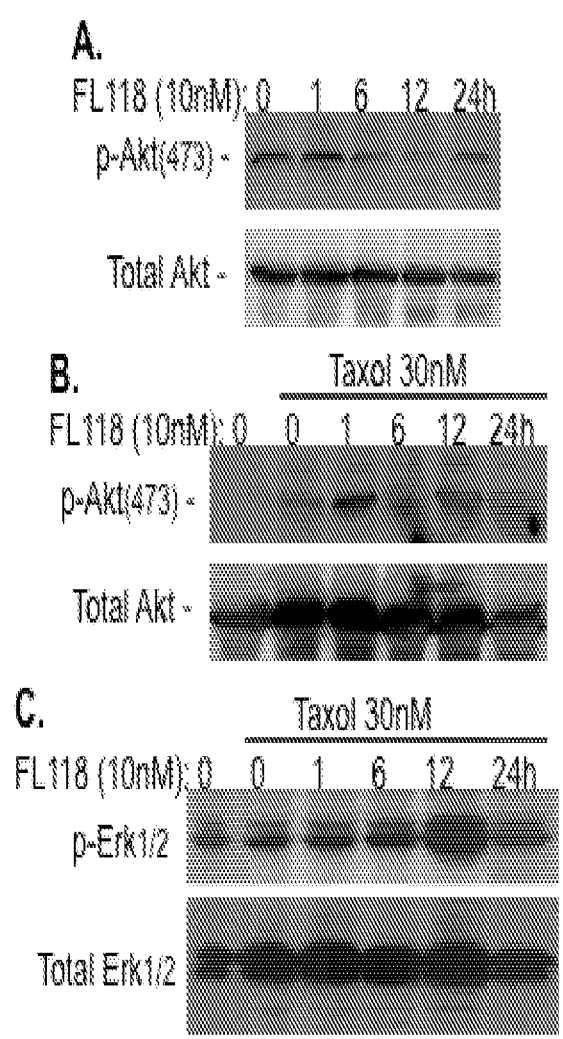

FIG. 25 Representative data to show differential effects of FL118 on Akt and MAP kinase pathways: Sub-confluent HCT-8 colon cancer cells were first treated with (B, C) and without (A) taxol (30 nM) for 2 hours, followed by a time course treatment with FL118 as indicated. After lysis of the treated cells, total and phosphorylated Akt and Erk1/2 were determined by western blots. As shown, FL118 inhibits both the constitutive and taxol-induced Akt survival signaling. In contrast, FL118 shows no inhibitory effects on Erk signaling, indicating its high-specific effect on distinct signaling pathways. Of note, the exposure time for p-Akt detection in A is about 4 times of p-Akt detection in B.

Figure 26:
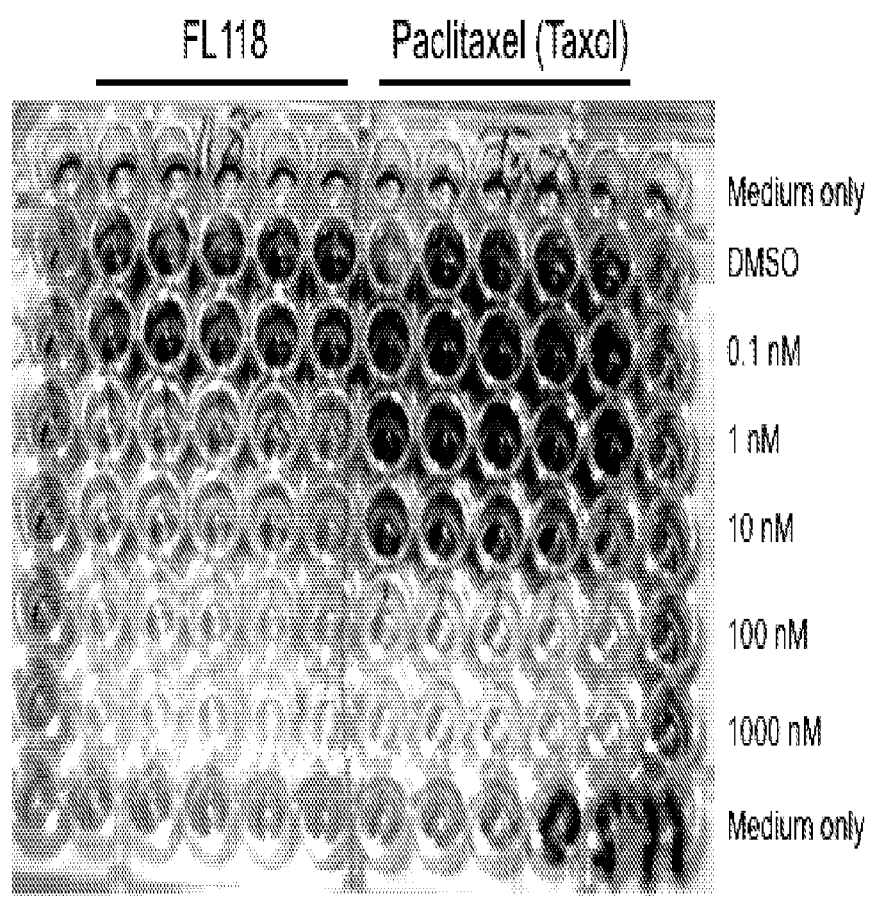

FIG. 26 A representation for comparison of the potential of FL118 and taxol (paclitaxel) in cancer cell survival/growth inhibition using MTT assay. H1650 lung cancer cells were seeded in 96 well plates (2000 cells per well). Cells were treated with FL118 or taxol at a series of different concentrations as shown 24 hours after seeding. Cell viability was determined by MTT assay 72 hours after treatment. As shown, FL118 is about 10-100 fold more effective than taxol in ablation of cell viability.

Figure 27:
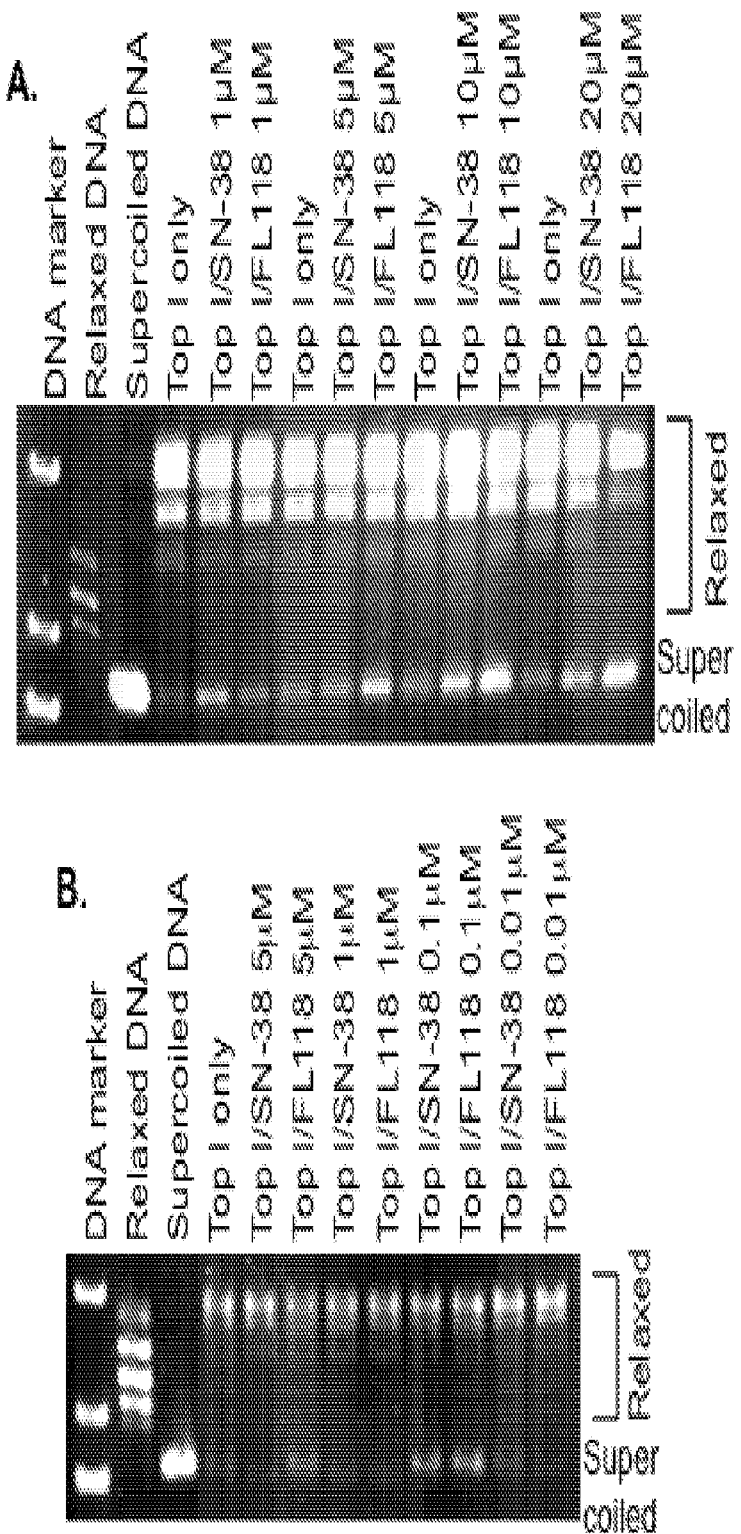
Figure 27:
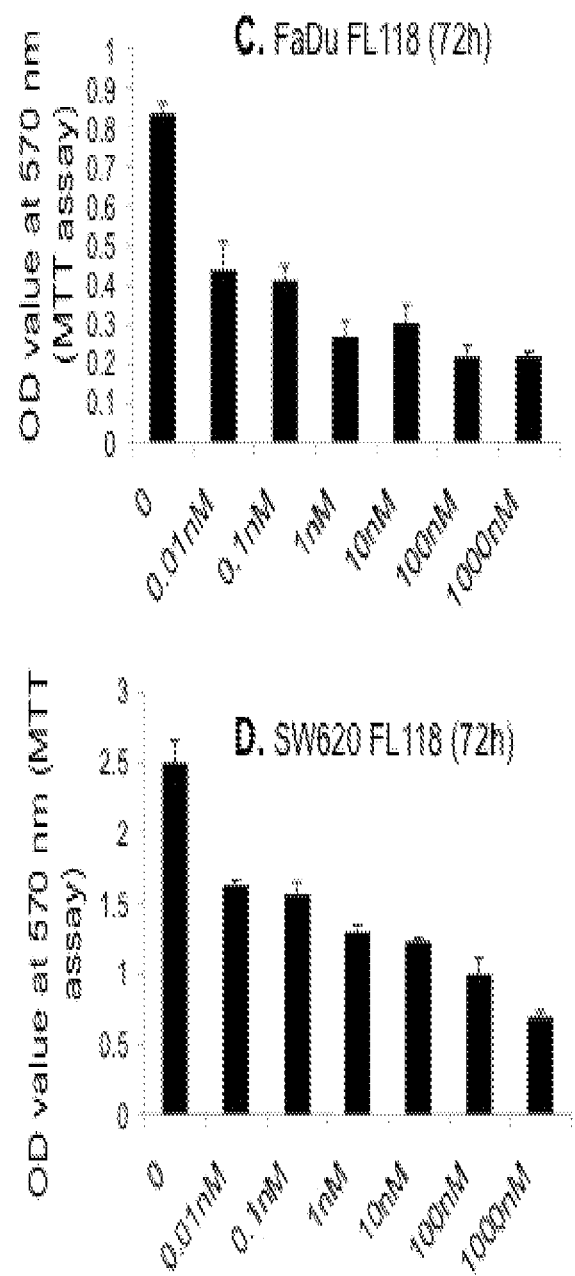

FIG. 27 Representative experiments to show the effect of FL118 and SN-38 (the active form of irinotecan) on topoisomerase I activity (A and B) and on cell growth/viability (C and D). The experimental condition is described in the Method section.

Figure 28:
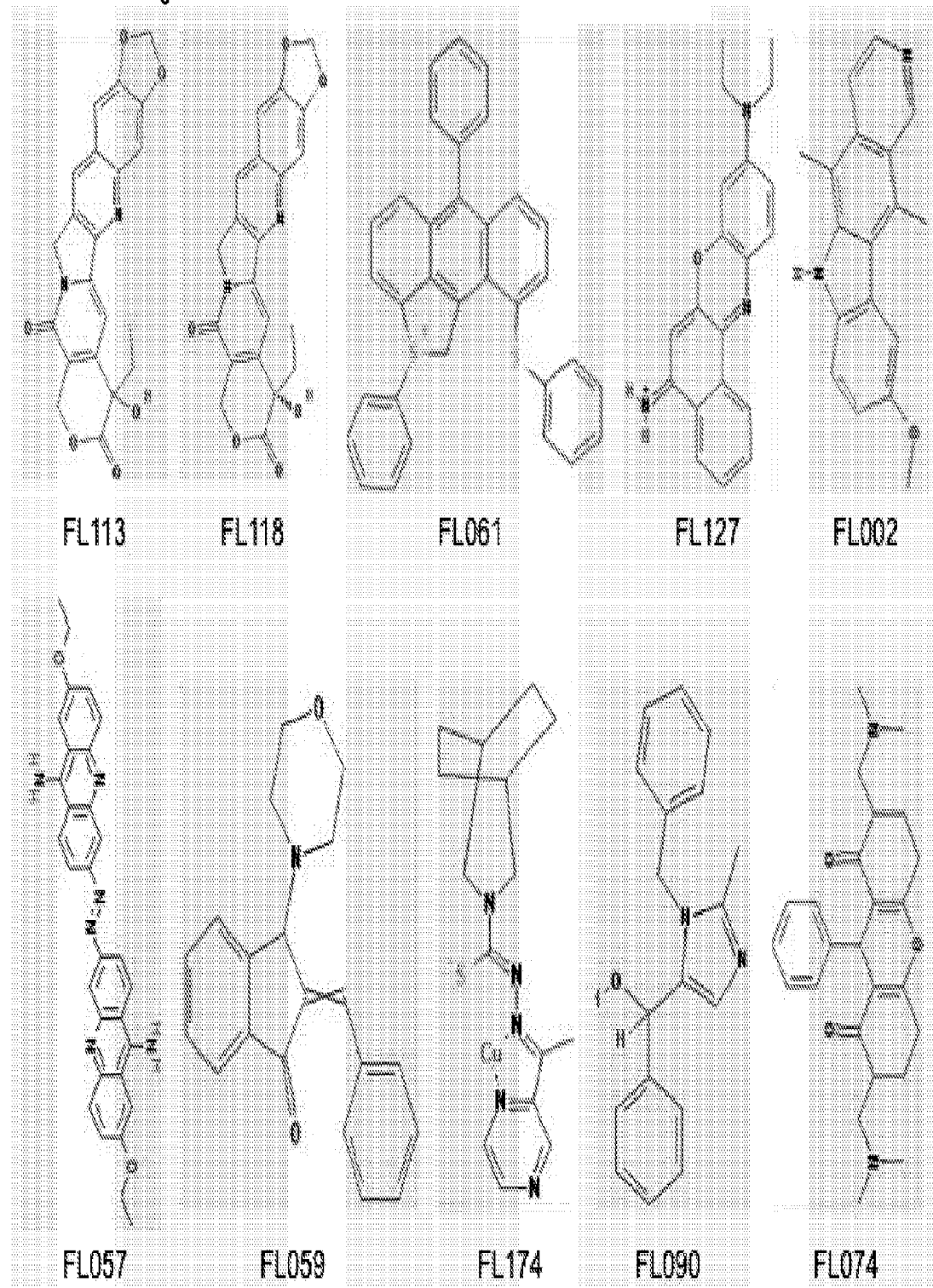

FIG. 28 Chemical structures of ten distinct compounds that were used for testing water-insoluble drug formulation according to the invention.

Figure 29:
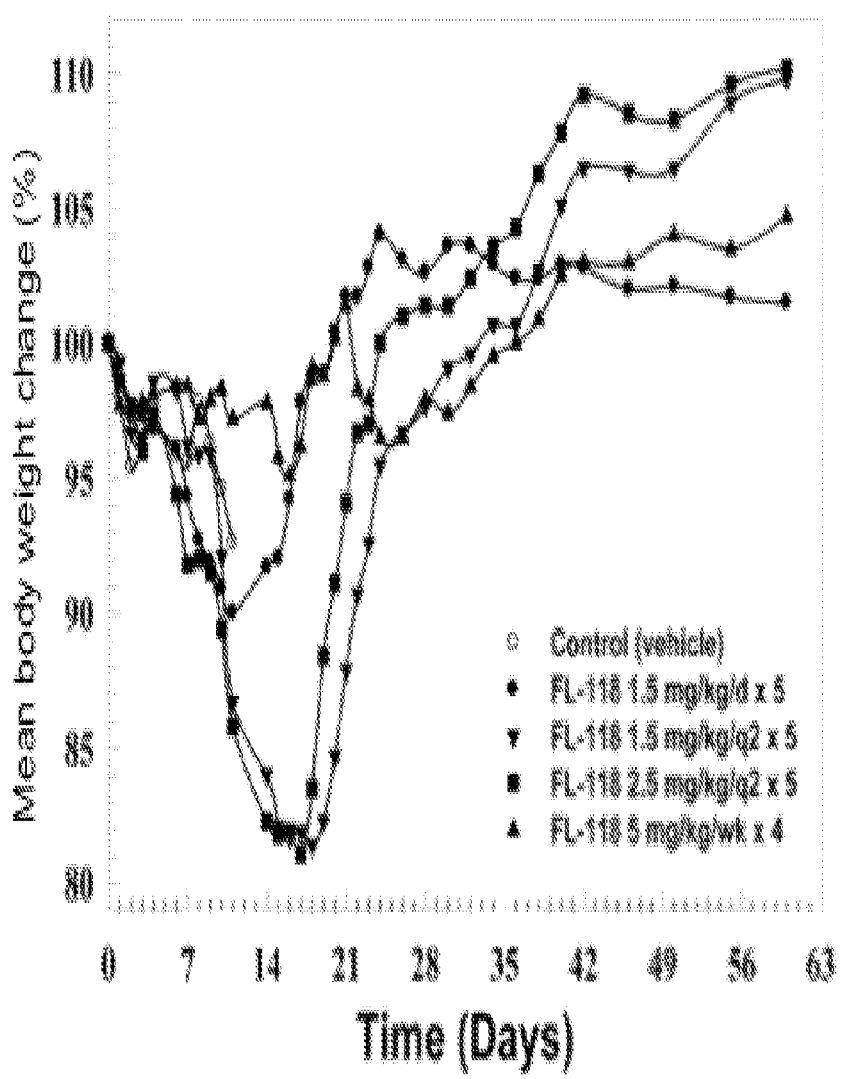

FIG. 29 Toxicity (mouse body weight loss) upon FL118 treatment with the doses and schedules as shown: SCID mice (3 mice per group) were treated at the dose of 1.5 mg/kg daily for 5 times from Day 0; at the doses of 1.5 and 2.5 mg/kg every other day for 5 times; and at the dose of 5 mg/kg weekly×4 for 4 times via the i.v. route, as shown. Each dose schedule curve is the average body weight loss from 3 mice. FL118 at 0.5 mg/ml were formulated in DMSO (5%), HPβCD (0.25%) and saline (95%,). Control group was treated with the control solution (DMSO, 5%; HPβCD, 0.25% and saline, 95%,) without FL118 daily for 5 times (d×5).

Figure 30:
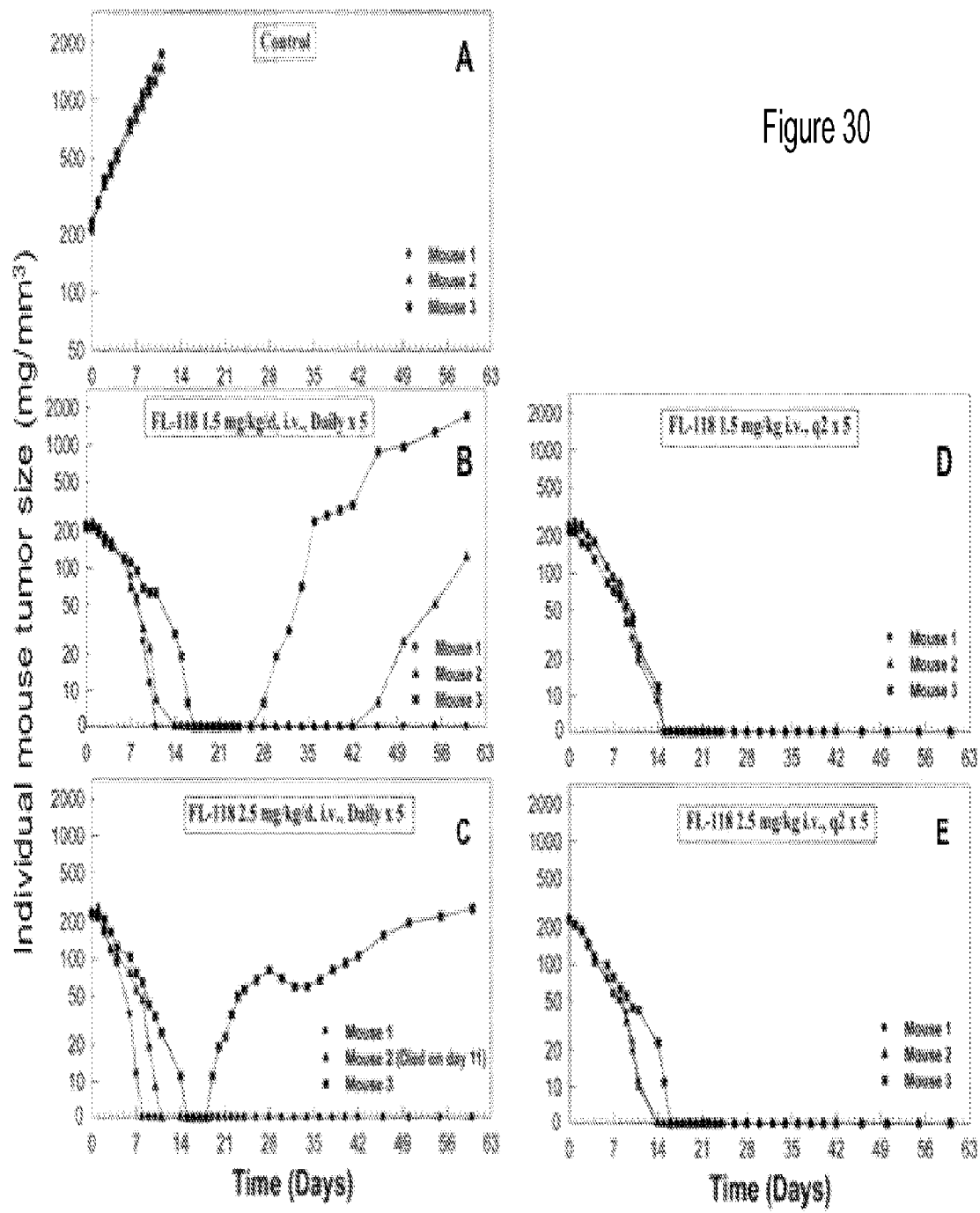
Figure 30:
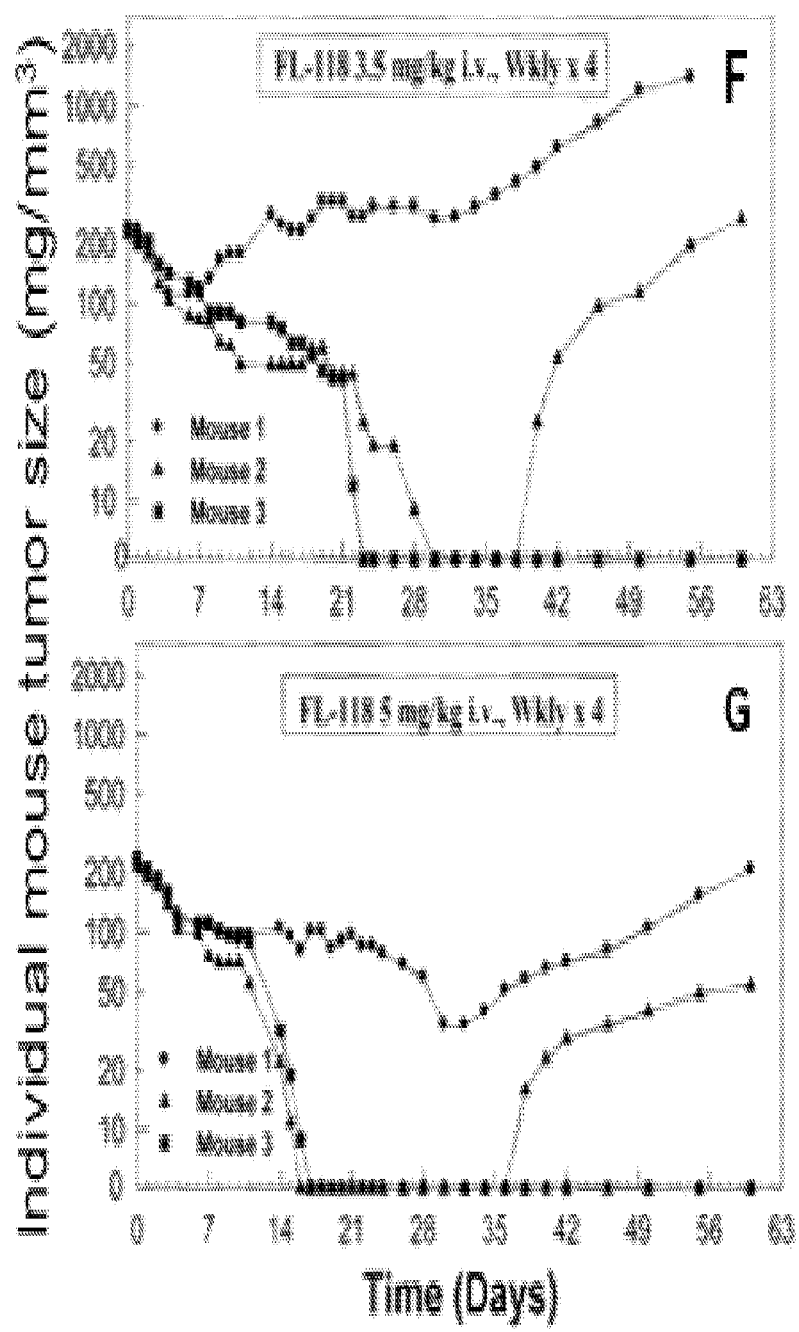

FIG. 30 Tumor curves from individual mice in three types of schedules for FL118 treatment in human FaDu head-&-neck tumor SCID mouse xenograft models: Treatment was initiated 7 days after subcutaneous tumor implantation (designated Day 0), on which tumor weight is about 200-250 mg. FL118 (0.5 mg/ml) formulated in DMSO (5%), HPβCD (0.25%) and saline (95%,) was administrated via the i.v. route on Day 0 at the doses and schedules as follows. A. Control group was treated with the control solution (DMSO, 5%; HPβCD, 0.25% and saline, 95%,) without FL118 daily for 5 times (d×5 schedule). B and C. Antitumor activity of FL118 at the dose of 1.5 mg/kg and 2.5 mg/kg with the daily×5 schedule (5 times). D and E. Antitumor activity of FL118 at the dose of 1.5 mg/kg and 2.5 mg/kg with the every other day×5 schedule (5 times). F and G. Antitumor activity of FL118 at the dose of 3.5 mg/kg and 5 mg/kg with the weekly×4 schedule (4 times).

Figure 31:
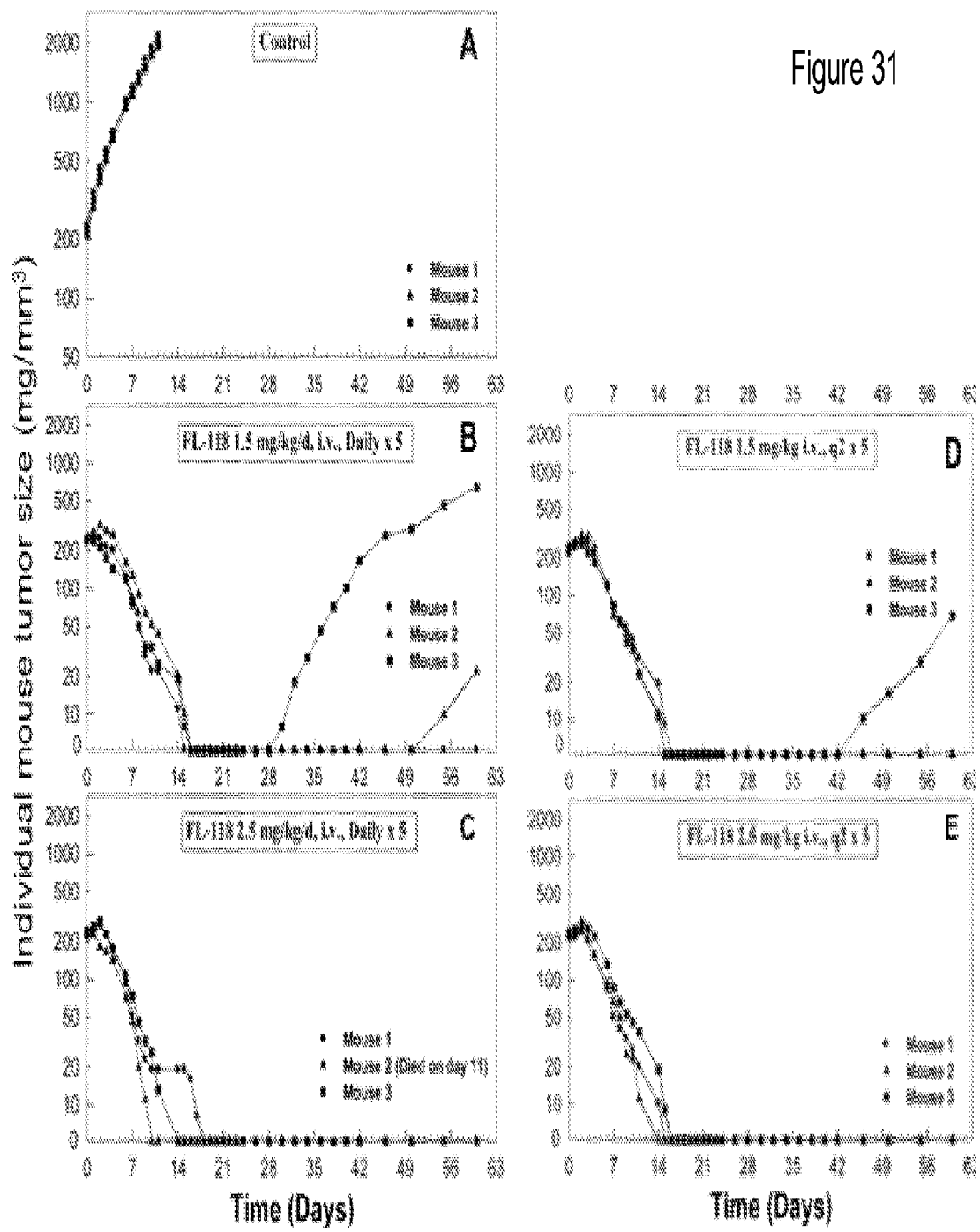
Figure 31:
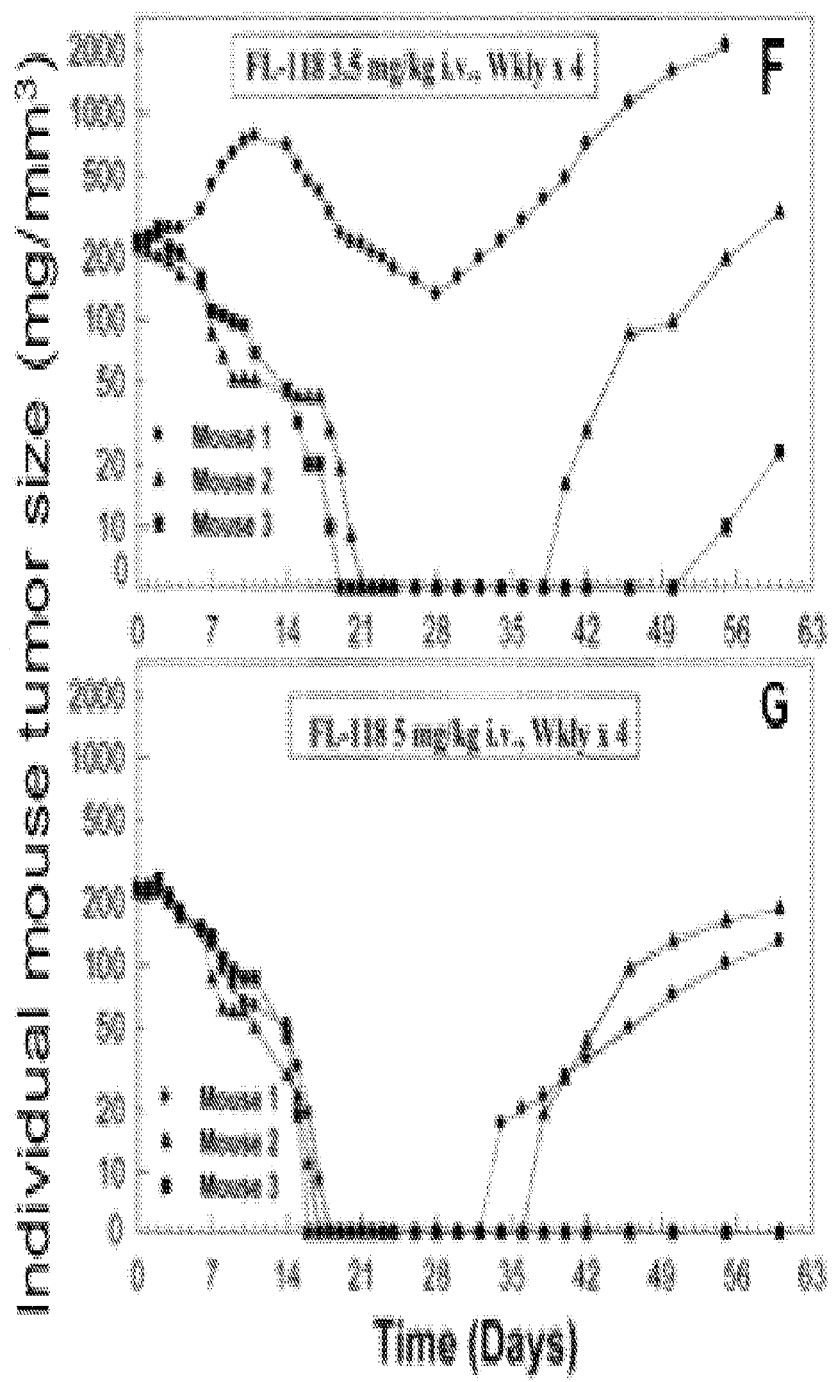

FIG. 31 Tumor curves from individual mice in three types of schedules for FL118 treatment in human SW620 colon tumor SCID mouse xenograft models: Treatment was initiated 7 days after subcutaneous tumor implantation (designated Day 0), on which tumor weight is about 200-250 mg. FL118 (0.5 mg/ml) formulated in DMSO (5%), HPβCD (0.25%) and saline (95%,) was administrated via the i.v. route on Day 0 at the doses and schedules as follows. A. Control group was treated with the control solution (DMSO, 5%; HPβCD, 0.25% and saline, 95%,) without FL118 daily for 5 times (d×5 schedule). B and C. Antitumor activity of FL118 at the dose of 1.5 mg/kg and 2.5 mg/kg with the daily×5 schedule (5 times). D and E. Antitumor activity of FL118 at the dose of 1.5 mg/kg and 2.5 mg/kg with the every other day×5 schedule (5 times). F and G. Antitumor activity of FL118 at the dose of 3.5 mg/kg and 5 mg/kg with the weekly×4 schedule (4 times).

FIG. 32 Tumor curves from individual mice in the weekly×4 schedules at the dose of 5 mg/kg for FL118 in human mesothelioma (211H and H226) tumor SCID mouse xenograft models: Treatment was initiated 7 days after subcutaneous tumor implantation (designated Day 0), on which tumor weight is about 200-250 mg. FL118 (0.5 mg/ml) formulated in DMSO (5%), HPβCD (0.25%) and saline (95%,) was administrated via the i.v. route on Day 0 at the weekly×4 schedules (4 times). A. Control group from 211H mesothelioma tumor was treated with the control solution (DMSO, 5%; HPβCD, 0.25% and saline, 95%,) without FL118 weekly×4 for 4 times (wk×4 schedule). B. Antitumor activity of FL118 for 211H mesothelioma tumor at the dose of 5 mg/kg with the weekly×4 schedule (4 times). C. Control group from H226 mesothelioma tumor was treated with the control solution (DMSO, 5%; HPβCD, 0.25% and saline, 95%,) without FL118 weekly×4 for 4 times (wk×4 schedule). D. Antitumor activity of FL118 for H226 mesothelioma tumor at the dose of 5 mg/kg with the weekly×4 schedule (4 times).

DESCRIPTION OF THE INVENTION

The present invention provides compositions, methods of making the compositions, and methods of using the compositions for cancer therapy. In general, the compositions comprise novel pharmaceutical preparations which contain effective concentrations of a chemical compound. In various embodiments, the chemical compound is an anticancer agent with poor water solubility. In this regard, we have also developed a general methodology for preparing pharmaceutical preparations which are expected to be suitable for intravenous (i.v.) and oral pharmaceutical preparations for a wide variety of drug compounds that are difficult to dissolve in water.

In the context of the present invention, poorly water-soluble drug compounds include but are not necessarily limited to compounds which are Biopharmaceutics Classification System (BCS) class 2 or class 4 drugs. The BCS is well known to those skilled in the art and is based on the aqueous solubility of drugs reported in readily available reference literature, and for drugs that are administered orally it includes a correlation of human intestinal membrane permeability. (See, for example, Takagi et al., (2006) Molecular Pharmaceutics, Vol. 3, No. 6, pp 631-643.) In one embodiment, solubility can be determined according to the parameters set forth in this matrix:

| Solubility in water | Parts of water solvent required for 1 part of solute | Solubility Range in water (mg/ml) |
|---|---|---|
| very soluble | <1 | ≥1000 |
| freely soluble | from 1 to 10 | 100-1000 |
| soluble | from 10 to 30 | 33-100 |
| sparingly soluble | from 30 to 100 | 10-33 |
| slightly soluble | from 100 to 1000 | 1-10 |
| very slightly soluble | form 1000 to 10000 | 0.1-1 |
| practically insoluble | ≥10000 | <0.1 |

For the purposes of the present invention, a poorly water-soluble pharmaceutical agent that can be provided as a pharmaceutical agent according to the invention is any drug that falls into the categories: very slightly soluble, and practically insoluble as set forth in the above matrix, although the formulation method described in this invention could increase a drug that falls into the categories sparingly soluble and slightly soluble for 10-100 folds of solubility in the formulated solution. This is very good for any drug with low potency and high maximum tolerated dose (MTD) such as irinotecan (MTD: 100-200 mg/kg) for disease treatment.

In one aspect of the invention, we provide formulations for use in cancer therapy which comprise 10H-1,3-Dioxolo[4,5-g]pyrano[3',4':6,7]indolizino[1,2-b]quinoline-8,11(7H,12H)-dione, 7-ethyl-7-hydroxy-, (S)-. This compound is referred to herein as "FL118." It corresponds to NSC number 634724. This composition is also alternatively referred to as 10,11-Methylenedioxy-20S-camptothecin. The structure of this compound, as well as other structurally diverse compounds which are used for providing pharmaceutical preparations in the present invention, are presented in FIG. 28.

In arriving at the present invention, we have made the surprising discovery that we can make pharmaceutical preparations using compounds which, under a variety of criteria which are conventionally used to assess the suitability of test agents for use in cancer therapy, are too toxic or cannot be properly formulated for clinically relevant applications. Using our newly developed method, we can provide such compounds in formulations such that they can be used to elicit unexpected and superior anti-cancer effects in clinically relevant animal models. Specifically, in view of the disclosure presented herein, the skilled artisan will recognize at least the following aspects of the invention: 1) FL118 possesses exceptional and surprising antitumor activity (with manageable toxicity) in human tumor xenograft animal models; 2) FL118 possesses broad potential in combination with other chemotherapeutic and chemopreventive agents for cancer treatment; 3) the invention provides formulations and methods of making formulations for water-insoluble drugs (e.g. FL118) for use as injectable and oral administration routes; 4) antitumor activity of FL118 has highly steric structural relevance, as the same compound with different steric structure (FL113) as described further below shows much weaker antitumor activity; and 5) FL118 possesses a unique mechanism of action (MOA).

With respect to its MOA, we show: a) FL118 selectively inhibits the expression of IAP (inhibitor of apoptosis) and Bcl-2 family antiapoptotic proteins including survivin, XIAP, cIAP-2 and Mcl-1; b) FL118 induces the expression of Bcl-2 family proapoptotic proteins (Bax, Bim) and apoptosis (caspase activation and PARP cleavage); and c) FL118 selectively inhibits both constitutive and taxol-induced activation of Akt survival signaling, while it shows little inhibitory effect on Erk1/2 signaling. Thus, we show for the first time that FL118 possesses unusual and surprising antitumor activity that can inhibit and even eradicate cancer, and it can be also used in combination with other chemotherapeutic and chemopreventive agents. The surprising antitumor activity of FL118 with manageable toxicity is consistent with its unique MOA that we characterize for the first time in this disclosure.

For each of the pharmaceutical preparations described herein all of the values described unless stated otherwise include each value at the upper and lower end of the range, and all integer numbers to the second decimal point, and all integer ranges there between. Thus, for example a drug concentration described as having a range of 0.5-1 mg/ml includes 0.5 mg/ml, 0.6 mg/ml, 0.7 mg/ml, 0.8 mg/ml, 0.9 mg/ml and 1.0 mg/ml. Each pharmaceutical preparation disclosed herein can comprise, consist essentially of, or consist of the components described for it. Further, any component of the solvents and co-solvents involved in the making and/or using the preparations may or may not be included in the pharmaceutical preparations provided by the invention.

In non-limiting embodiments of the invention, pharmaceutical preparations of drug compounds, such as FL118, are provided in combination with other formulation components. Generally, in addition to the drug compound, the formulations include a first solvent (also referred to herein as Solvent A or Sol A); a second solvent (also referred to herein as Solution B or Sol B); an aqueous solution, and optionally, one or more helper solvents. The type and amount of each of these components can be adjusted to accommodate for such factors as a desired drug concentration, method of making the preparation, and the intended route of administration and formulation volume. Each of these factors will be related to considerations such as the intended dosing schedule, the sex, age, and size of the individual being treated, and the type and stage of disease being treated.

In particular embodiments, pharmaceutical preparations of the invention comprise a drug, Solvent A, Solvent B, and 0-10% helper solvents. Solvent A can be a composition that forms a complex with the drug. For example, any of a variety of cyclodextrins (CD) known to increase drug solubility can be used. In particular non-limiting embodiments, Solvent A can be β cyclodextrin (βCD), hydroxypropyl-β-cyclodextrin (HPβCD) or sulfobutylether-β-cyclodextrin (SBEβCD). Solvent B can be a polar aprotic solvent such as dimethyl sulfoxide (DMSO), or it can be an alcohol, such as ethanol. The helper solvent can be a diol or double alcohol, such as propylene glycol (PG), or a polyether compound, such as polyethylene glycol 300 or 400 (PEG 300 or PEG 400). Combinations of helper solvents can also be included.

Methods of making exemplary formulations having these components are described below in detail for the selection of specific processes and parameters make the formulations. In general, the invention provides three approaches (Strategy I, Strategy II and Strategy III) for preparing a composition comprising a drug that is poorly soluble in water.

Strategy I:

First, a leading solvent solution is made—dissolve a Solvent A (βCD, HPβCD or SBEβCD) into a Solvent B (DMSO or ethanol) by gently swirling the solution in a tube for 5-15 minutes at room temperature to form a leading Solvent A/B mixture solution. Which Solvent A (βCD, HPβCD or SBEβCD) is selected to make the leading Solvent A/B mixture solution depends on the chemical property of the water-insoluble compound. Generally speaking, if a compound has acidic group, the Solvent A can be βCD or HPβCD, since they are neutral or basic; if a compound has one or more basic groups, Solvent A can be SBEβCD, since SBEβCD has acidic groups. Which Solvent B (i.e., DMSO or ethanol) to select depends on in which solvent (DMSO or ethanol) the water-insoluble compound dissolves better. For example, testing indicates that FL113 and FL118 poorly dissolve in ethanol but dissolve in DMSO with a low but reasonable concentration (~1 mg/ml). So DMSO is selected as Solvent B for FL113 and FL118 formulation. Solvent A (βCD, HPβCD or SBEβCD) in the final, ready-to-use formulation solution (W/V) is as low as 0.2% and as high as 5%, which depends on the compound final concentration in the ready-to-use formulated solution. Therefore, the percentage of Solvent A (βCD, HPβCD or SBEβCD) in Solvent B (DMSO or ethanol) is in the range of 2.5% to 50%, which is dependent on the amount of compound that we desire to formulate. 2) Make helper solvent solution. In general, an aqueous humor (distill water, saline or phosphate-buffered saline) is mixed with a helper solvent (PG, PEG 300 or PEG 400) by gently swirling on a swirling apparatus for up to overnight at 25-37° C. These helper solvent solutions include, but are not limited to: Recipe 1 saline (distill water or phosphate-buffered saline) is mixed with PG at 0%, (Helper solvent 1, Hsol-1), 1% (Hsol-2), 2% (Hsol-3), 3% (Hsol-4), 4% (Hsol-5), 5% (Hsol-6), 6% (Hsol-7), 7% (Hsol-8), 8% (Hsol-9), 9% (Hsol-10) and 10% (Hsol-11); Recipe 2 saline (distill water or phosphate-buffered saline) is mixed with PEG 400 (or PEG 300) at 1% (Hsol-1), 2% (Hsol-2), 3% (Hsol-3), 4% (Hsol-4), 5% (Hsol-5), 6% (Hsol-6), 7% (Hsol-7), 8% (Hsol-8), 9% (Hsol-9) and 10% (Hsol-10); and Recipe 3 saline (distill water or phosphate-buffered saline) is mixed with 1% PG/9% PEG 400 (Hsol-1), 2% PG/8% PEG 400 (Hsol-2), 3% PG/7% PEG 400 (Hsol-3), 4% PG/6% PEG 400 (Hsol-4), 5% PG/5% PEG 400 (Hsol-5), 6% PG/4% PEG 400 (Hsol-6), 7% PG/3% PEG 400 (Hsol-7), 8% PG/2% PEG 400 (Hsol-8), 9% PG/1% PEG 400 (Hsol-9). Of note, higher percentage of helper solvents (PG, PEG 300 or PEG 400) can be made but the higher these helper solvents in the ready-to-use formulated solution, the potential more toxic the formulated solution would be. 3) Formulate water-insoluble compounds using both leading solvent solution and helper solvent solution. Dissolve a water-insoluble compound in leading solvent solution (the compound may or may not completely dissolved) by Vortex for 5-15 minutes. Then dilute the drug dissolved in leading solvent solution with helper solvent solution by gently swirling the mixture in a container on a swirling apparatus for 10-20 minutes at room temperature. Using FL118 as an example, in order to make FL118 at a final concentration of 0.5 mg/ml, we can dissolve 1 mg FL118 (as an example, but this can be any amount of FL118, so long as the same ratio is maintained) in 0.1 ml≥5% HPβCD (βCD or SBEβCD) leading solution in DMSO via Vortex for 5 minutes. Then the resultant FL118/HPβCD/DMSO mixture is further diluted in 1.9 ml (20× dilution) in one of the above water-based helper solvent solutions in the above three recipes by gently swirling the tube on a swirling apparatus for 10-20 minutes at room temperature. Specifically, if the resultant FL118/HPβCD/DMSO mixture is further diluted in 1.9 ml Hsol-1 of Recipe 1 to reach a total volume of 2 ml, the final, ready-to-use FL118 formulation solution will be FL118 0.5 mg/ml, HPβCD≥0.25%, DMSO ~5% and PG 0%; if the resultant FL118/HPβCD/DMSO mixture is further diluted in 1.9 ml Hsol-11 of Recipe 1 to reach a total volume of 2 ml, the final, ready-to-use FL118 formulation solution will be FL118 0.5 mg/ml, HPβCD≥0.25%, DMSO ~5% and PG 9.5%). Similarly, in this case, if the resultant FL118/HPβCD/DMSO mixture is further diluted in 1.9 ml Hsol-1 of Recipe 3 to reach a total volume of 2 ml, the final, ready-to-use FL118 formulation solution will be FL118 0.5 mg/ml, HPβCD 0.25%, DMSO ~5%, PG 0.95% and PEG 400 8.55%; if the resultant FL118/HPβCD/DMSO mixture is further diluted in 1.9 ml Hsol-9 of Recipe 3 to reach a total volume of 2 ml, the final, ready-to-use FL118 formulation solution will be FL118 0.5 mg/ml, HPβCD≥0.25%, DMSO ~5%, PG 8.55% and PEG 400 0.95%. By application of the above formulation process using leading solvent solutions and helper solvent solutions, we are able to successfully formulate individual water-insoluble compounds with diverse chemical structures shown in FIG. 28 at a broad range of drug concentrations. Again using FL118 as an example, if FL118 at a final concentration of 0.25 mg/ml is desired, we can dissolve 1 mg FL118 (again, as an example, but FL118 can be any amount as long as the same ratio is maintained) in 0.2 ml≥2.5% HPβCD (CD or SBEβCD) solution in DMSO via Vortex for 3-10 minutes. Then the resultant FL118/HPβCD/DMSO mixture is further diluted in 3.8 ml (20× dilution) in one of the above 3 helper solvent solutions to reach a final volume of 4 ml (FL118 0.25 mg/ml, HPβCD≥0.125%, DMSO 5%, water-based helper cosolvents ~95%). If a higher concentration of FL118 for injectable solution with this formulation process is desired, such as a final injectable solution at 1 mg/ml, we can dissolve 2 mg FL118 in 0.1 ml≥20% HPβCD (CD or SBEβCD) solution in DMSO via Vortex for 5-15 minutes. Then the resultant FL118/HPβCD/DMSO mixture is further diluted in 1.9 ml (20× dilution) in one of the above helper solvent solutions to reach a final volume of 2 ml (FL118 1 mg/ml, HPβCD≥0.5%, DMSO ~5%, water-based helper cosolvents ~95%). In conclusion, Strategy I can be used to formulate a chemical compound for i.v. injection (which is inherently compatible for i.p. and p.o. routes) at the desired concentration in preclinical animal model studies or in clinical trials, and for treatment of patients. The ability to formulate a drug in a wide range of different concentrations in the final, ready-to-use solution is important, because evaluation of a drug either in preclinical animal models or in clinical trials needs a dose escalation from low dose to high dose, while keeping an optimal and consistent volume size—too small volume may produce a larger system error and technical difficulty for drug administration, while too large volume may not be able to practically inject all of the solution to reach the drug dose needed. Additionally, different drug administration routes (i.v., i.p. or p.o.) can be adapted for different volumes.

Strategy II:

In this approach, after a water-insoluble compound dissolves in the leading Solvent A ((βCD, HPβCD or SBEβCD)/Solvent B (DMSO or ethanol) mixture, one or two helper solvents (PG, PEG 300 or PEG 400) are added to the compound/Solvent A/Solvent B mixture by gently swirling the solution in a tube for up to overnight at 25-37° C. on a swirling apparatus. Then an aqueous humor (distill water, saline or phosphate-buffered saline) is used to dilute the resultant drug solution to a desired concentration and meanwhile, after drug dilution with an aqueous humor the percentage of helper solvents (PG, PEG 300 or PEG 400) in the final, ready-to-use drug formulation solution remains in the range from 1% to 10% in total. Using FL118 as an example, if we formulate FL118 for a final concentration of 0.25 mg/ml with 2% PG, we dissolve 1 mg FL118 (an example, but can be any amount as long as same ratio is used) in 0.2 ml≥2.5% HPβCD (βCD or SBEβCD) solution in DMSO via Vortex for 5-15 minutes. Then add 0.08 ml PG into the resultant FL118/HPβCD/DMSO mixture to mix for up to overnight at 25-37° C. by gently swirling the solution in a tube on a swirling apparatus. The resultant drug solution is further diluted with 3.72 ml aqueous humor (distill water, saline or phosphate-buffered saline) by gently swirling the tube on a swirling apparatus for up to overnight at 25-37° C. to reach a final volume of 4 ml (FL118 0.25 mg/ml, HPβCD≥0.125%, DMSO ~5%, PG 2%). If we formulate a higher concentration of FL118 injectable solution with this approach such as making a final injectable solution at 1 mg/ml with 2% PG and 2% PEG 400, we dissolve 2 mg FL118 (again as an example, but the drug can be provided in any amount as long as the same ratio is used) in 0.1 ml≥10% HPβCD (CD or SBEβCD) solution in DMSO via Vortex for 5-15 minutes. Then add 0.04 ml PG and 0.04 ml PEG 400 into the resultant FL118/HPβCD/DMSO mixture to mix by swirling the solution in a tube for up to overnight at 25-37° C. on a swirling apparatus. The resultant drug solution is further diluted with 1.72 ml aqueous humor (distill water, saline or phosphate-buffered saline) by gently swirling the tube on an apparatus for up to overnight at 25-37° C. to reach a final volume of 2 ml (FL118 1 mg/ml, HPβCD≥0.5%, DMSO ~5%, PG 2%, PEG 400 2%). By using this approach, we are able to make our desired drug formulation solution for i.v. administration (also compatible for i.p. and p.o.).

Strategy III:

In this approach, after Solvent A (βCD, HPβCD or SBEβCD) is dissolved in Solvent B (DMSO or ethanol), the resultant Solvent A/B mixture is further mixed with one or two helper solvents (PG, PEG 300 or PEG 400) to make a leading master solvent mixture. Then a water-insoluble compound is dissolved in this leading master solvent mixture by gently swirling the solution in a tube for a minimal overnight at 25-37° C. on a swirling apparatus. The water-insoluble compound dissolved in the leading master solvent mixture are then diluted in an aqueous humor (distill water, saline or phosphate-buffered saline) to reach the desired drug concentration by gently swirling the solution in a tube for up to overnight at 25-37° C. on a swirling apparatus. As with Strategy II above, after dilution of the leading master solvent solution with an aqueous humor, the percentage of helper solvents (PG, PEG 300 or PEG 400) in the final, ready-to-use drug formulation solution remains in a range of 1% to 10% in total. Using the same examples described in the Strategy II for FL118 formulation to illustrate, if FL118 is to be formulated at a final concentration of 0.25 mg/ml with 2% PG, we first mix 0.08 ml PG in 0.2 ml≥2.5% HPβCD (CD or SBEβCD) solution in DMSO by gently swirling the solution in appropriate size tube (e.g. 0.5 ml tube) for up to overnight at 25-37° C. on a lab swirling apparatus. Then dissolve 1 mg FL118 in the resultant leading master solvent (HPβCD/DMSO/PG) by gently swirling the solution in the tube for a minimal 16 hours at 25-37° C. on a swirling apparatus. The resultant FL118 solution is further diluted with 3.72 ml aqueous humor (distilled water, saline or phosphate-buffered saline) by gently swirling the solution in a large tube for up to overnight at 25-37° C. on a swirling apparatus to reach a final volume of 4 ml (FL118 0.25 mg/ml, HPβCD≥0.125%, DMSO ~5%, PG 2%). Similarly, if it is desirable to formulate a high concentration of FL118 for use as an injectable solution with this approach, such as making a final injectable solution at 1 mg/ml with 2% PG and 2% PEG 400, we first mix 0.04 ml PG and 0.04 ml PEG 400 in 0.1 ml≥10% HPβCD (CD or SBEβCD) solution in DMSO by gently swirling the solution in a tube for a minimal 16 hours at 25-37° C. on a swirling apparatus. Then dissolve 2 mg FL118 in the resultant leading master solvent (HPβCD/DMSO/PG/PEG 400) by gently swirling the solution in a tube for up to overnight at 25-37° C. on a swirling apparatus. The resultant FL118 solution is further diluted with 1.82 ml aqueous humor (distill water, saline or phosphate-buffered saline) by gently swirling the solution in a tube for up to overnight at 25-37° C. on a swirling apparatus to reach a final volume of 2 ml (FL118 1 mg/ml, HPβCD≥0.5%, DMSO ~5%, PG 2%, PEG 400 2%). By using this approach, we are also able to make desired drug formulation solution for i.v. administration (also compatible for i.p. and p.o.). We found that for the poorly water-insoluble compounds, Strategy II and Strategy III are more effective to dissolve such water-insoluble compounds in an acceptable concentration with better solution stability for i.v. administration. Additionally, when formulating water-insoluble compounds using the three approaches described above, it is preferable that the percentage of DMSO or ethanol remain in a range of percentage from 5% to 10% in the final, ready-to-use drug formulation solution. This can be realized by using different percentages of Solvent A in Solvent B (DMSO or ethanol) in association with appropriate dilution to make the final, ready-to-use drug formulation solution. Alternatively, this could be realized by adding additional Solvent B (DMSO or ethanol) into the leading master mixture before diluting the leading muster mixture with aqueous humor (distill water, saline or phosphate-buffered saline). Of course, the amount of additional Solvent A (DMSO or ethanol) added in the leading master mixture should be subtracted from the aqueous humor volume for drug dilution. It is also preferable that the molar concentration of Solvent A versus the molar concentration of a compound in the final, ready-to-use formulated solution should be between 1.1-10 (Solvent A molar concentration): 1 (compound molar concentration), which depends on the chemical compound molecular weight, shape and other chemical properties. Generally speaking, a water-insoluble compound with large molecular weight in a non-linear structure needs a higher Solvent A: compound ratio (i.e. need more Solvent A). For a particular water-insoluble compound, this needs to be determined with testing that will be routine for the skilled artisan, given the benefit of the present disclosure. Generally speaking, it is preferable to use helper solvents in low amounts as long as a water-insoluble compound could be dissolved in a state with sufficient stability that could be used for i.v. injection effectively. Comparison of the three formulation strategies described above for water-insoluble compound formulation is summarized in Table 5.

cipitation in a reasonable time period, the formulated solution would be suitable for i.v. injection. If additional solubility is desired, the addition of helper solvents (PG, PEG 300 or PEG 400) can be employed, particularly PG, PEG 300 or PEG 400 via the approaches described in Strategy II and Strategy III would obtain better solubility for water-insoluble drug especially for a difficult-to-solubilize drug. Using FL118 as an example, lack of helper solvents (PG, PEG 300 or PEG 400) in the finally formulated FL118 i.v. injection solution [FL118, Solvent A (HPβCD), Solvent B (DMSO) and aqueous humor (distilled water, saline or phosphate-buffered saline)] decrease the stability of the formulated FL118 solution, how-

TABLE 5

Comparison of the three formulation strategies for formulating water-insoluble compounds for i.v. injection

| Formulation Strategies | First Approach (Strategy I) | Second Approach (Strategy II) | Third Approach (Strategy III) | Comparison of compositions or processing among Strategies I, II and III |
|---|---|---|---|---|
| Solvent A (Sol A) | βCD, HPβCD or SBEβCD | βCD, HPβCD or SBEβCD | βCD, HPβCD or SBEβCD | Same |
| Solvent B (Sol B) | DMSO or Ethanol | DMSO or Ethanol | DMSO or Ethanol | Same |
| Helper solvent | PG, PEG300 or PEG 400 | PG, PEG300 or PEG 400 | PG, PEG300 or PEG 400 | Same |
| Aqueous humor | Distill water, saline or phosphate-buffered saline | Distill water, saline or phosphate-buffered saline | Distill water, saline or phosphate-buffered saline | Same |
| Leading Solvent | One Sol A dissolved in One Sol B (Sol A/B mixture) | One Sol A dissolved in One Sol B (Sol A/B mixture) | One Sol A dissolved in One Sol B plus one or two helper solvents | Difference |
| Compound dissolved in | Sol A/B mixture | Sol A/B mixture | Sol A/B mixture with one or two helper solvents | Difference |
| Add helper solvents after compound dissolved in Leading Solvent | No | Yes (add one or two helper solvents in the Sol A/B mixture with drug) | No | Difference |
| Drug dilution solution | An aqueous humor plus one or two helper solvents | An aqueous humor | An aqueous humor | Difference |
| Components in the final, ready-to-use formulation solution | A drug, a type of Sol A, a type of Sol B, with 0-10% helper solvents | A drug, a type of Sol A, a type of Sol B, with 1-10% helper solvents | A drug, a type of Sol A, a type of Sol B, with 1-10% helper solvents | Difference |

In summary, generally speaking, if the formulation contains helper solvents (PG, PEG 300 or PEG 400) in any one of the three formulation strategies described above, the formulated solution increases drug solution stability. However, the more the helper solvents are in the formulated ready-to-use drug solution, the higher the potential toxicity of the formulated ready-to-use solution is. Therefore, during processing of the formulation strategies described above, it is preferable to test solubility without helper solvents (PG, PEG 300 or PEG 400). Further, it is not necessary for the drug or a drug candidate in the ready-to-use solution to be a true solution, as long as after shaking, the formulated solution shows no preever, the formulated ready-to-use FL118 solution without helper solvents (PG, PEG 300 or PEG 400) is still suitable for i.v. injection. Importantly, this formulation of FL118 did not decrease FL118 antitumor activity, while keeping its non-toxic quality. In other words, if a water-insoluble drug or drug candidate formulated using the Strategies I, II and III in the final, ready-to-use solution without helper solvents (PG, PEG 300 or PEG 400) maintains reasonable stability for administration using an i.v. injection procedure, the helper solvents (PG, PEG 300 or PEG 400) can be excluded.

It should be emphasized that the pharmaceutical formulations described above do not have to comprise fully solubulized drug, as long as the water-insoluble drug is not in a solid state. Rather, each compound molecule is dissolved in the final solvent mixture. The water-insoluble compound mixture formulated in the three strategies described above could be semi-transparent or nontransparent clear state with or without a faint color. We find that the formulated water-insoluble drug or drug candidate in most cases is a milk-like or clear cloud solution with or without color after gently re-suspending by swirling. The water-insoluble compound solutions formulated in the three strategies described above are compatible with clinical practice to treat patients or animals with a disease via i.v., i.p. or per oral for single administration or combinational administration with other therapeutic drug such as cisplatin, etopside, taxol or doxorubicin. A comparison of FL118 solutions formulated via the three distinct strategies (Strategy I, Strategy II and Strategy III) described above is summarized in Table 6. The FL118 concentration at 0.25 mg/ml, 0.5 mg/ml or 0.75 mg/ml (Table 6) is suitable for i.v. administration to reach a dose escalation from 1 mg/kg to 7.5 mg/kg with a reasonable volume size for i.v. administration for our mouse model system used in this invention. We found that in the case of the FL118 formulations, although the formulated FL118 solution is more stable in the presence of one or two helper solvents (PG and/or PEG 400), the antitumor activity of FL118 shows no clear difference between with and without one or two helper solvents (PG and/or PEG 400). However, i.p. injection of the formulation solution (placebo, vehicle or control solution without FL118) to test the formulation solution toxicity indicated that if larger volumes are required, the formulation solution containing one or two helper solvents (PG and/or PEG 400) tends to be toxic, depending on the percentages of the helper solvent.

Table 6 Examples of Formulation Recipes for FL118 Formulation Comparison for i.v. Injection

| FL118 concentration | Formulation Solution Recipes | Strategies Used |
| --- | --- | --- |
| 0.25 mg/ml | DMSO, 5%; HPβCD, 0.125% and saline, 95% | Strategy I |
| 0.5 mg/ml | DMSO, 5%; HPβCD, 0.25% and saline, 95% | Strategy I |
| 0.75 mg/ml | DMSO, 5%; HPβCD, 0.375% and saline, 95% | Strategy I |
| 0.75 mg/ml | DMSO, 5%; HPβCD, 0.3755%, PG, 10% and saline, 85% | Strategy I |
| 0.75 mg/ml | DMSO, 5%; HPβCD, 0.375%, PEG 400, 10% and saline, 85% | Strategy I |
| 0.75 mg/ml | DMSO, 5%; HPβCD, 0.3755%, PG, 5%, PEG 400, 5% and saline, 85% | Strategy I |
| 0.75 mg/ml | DMSO, 5%; HPβCD, 0.3755%, PG, 10% and saline, 85% | Strategy II |
| 0.75 mg/ml | DMSO, 5%; HPβCD, 0.375%, PEG 400, 10% and saline, 85% | Strategy II |
| 0.75 mg/ml | DMSO, 5%; HPβCD, 0.3755%, PG, 5%, PEG 400, 5% and saline, 85% | Strategy II |
| 0.75 mg/ml | DMSO, 5%; HPβCD, 0.3755%, PG, 10% and saline, 85% | Strategy III |
| 0.75 mg/ml | DMSO, 5%; HPβCD, 0.375%, PEG 400, 10% and saline, 85% | Strategy III |
| 0.75 mg/ml | DMSO, 5%; HPβCD, 0.3755%, PG, 5%, PEG 400, 5% and saline, 85% | Strategy III |

For use, the compositions can be diluted in an aqueous solution (also referred to herein as an aqueous humor). In various embodiments, the aqueous humor can be distilled water, saline or phosphate-buffered saline. In preferred embodiments in the final, ready-to-use formulation solution, the percentage of aqueous humor varies from the least 85% to the most 95%; the percentage of DMSO or ethanol varies from the least 1% to the most 10%; the percentage of CD (βCD, HPβCD or SBEβCD) varies from the least 0.125% to the most 5%; and the percentage of PG, PEG 300 or PEG varies from the least 0% to the most 10% in total.

All of the pharmaceutical compositions described herein can be used in combination with other therapies, such as other anti-cancer agents, chemotherapies, dietary alterations, and surgical interventions.

In general, when FL118 is the drug compound in a pharmaceutical preparation provided by the invention, it is preferable to have between 0.25-5 mg/ml FL118 as an effective, final and ready-to-use concentration. In certain embodiments, the FL118 is provided in a pharmaceutical preparation which comprises 0.5-1.0 mg/ml FL118, 95% aqueous solution, 0.25-0.5% cyclodextrin, and 5% polar aprotic solvent (DMSO), which are suitable for the preclinical in vivo testing using human tumor mouse models. In one embodiment, a pharmaceutical preparation of the invention comprises 0.5-1 mg/ml FL118, 95% saline, 0.25-0.5% HPβCD, and 5% DMSO.

In various embodiments, the pharmaceutical preparations of the invention can be provided in any well of a number of known pharmaceutical containers, such as a screw capped sterile vial, an ampule, a pre-loaded syringe, etc. Formulations can be provided as a ready-to-use liquid formulation for oral, i.v. or i.p. administration, or as a concentrated solution in the leading solvent (a type of CD dissolved in DMSO or ethanol) suitable for diluting to a desirable concentration with aqueous humor (distill water, saline or phosphate-buffed saline) containing 0-10% one or two helper solvents (PG, PEG 300 or PEG 400) prior to administration. In terms of oral administration of the drug, the concentrated drug solution can be adopted to a tablet, or in caplet or capsule form. Further, we have determined that formulations made using the invention show high drug efficacy stability during refrigeration. Therefore, in various embodiments, the invention provides a pharmaceutical preparation of the invention that is held at a refrigerated temperature, such as from 1 degree Celsius, to less than 8 degrees Celsius. The compositions can be held in a refrigerated temperature for up to 1 year in a sterile condition of the formulation solution.

Pharmaceutical preparations of the invention can be administered to any human or non-human animal in need of therapy for one or more conditions for which the pharmaceutical preparation is intended to provide a prophylactic or therapeutic benefit. The present invention is expected to be useful for therapy of any of a wide variety of cancer types. Thus, the individual can be diagnosed with or suspected of having any of a variety of cancers, non-limiting examples of which include solid tumors and blood cancers (leukemia, lymphoma and myeloma). Specific examples of cancers include but are not limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, and thymoma.

Among the compounds listed in FIG. 28 that are formulated using the formulation approaches described herein (Strategy I, Strategy II and Strategy III), FL118 is an antitumor compound that has been extensively investigated with various formulations (Table 6) in the preclinical mouse models with or without human tumor for testing drug toxicity (mouse body weight loss) and evaluating drug antitumor activity (tumor growth inhibition, tumor regression and tumor eradication). In terms of preclinical mouse models, generally speaking, oral administration of FL118 formulated via the three formulation approaches (Strategy I, Strategy II and Strategy III; Table 6) could reach higher MTD doses than the dose that can be reached via the i.v. and i.p. routes. Usually, the oral administration of FL118 reaches a MTD with 25%-35% higher than the MTD reached via i.v. or i.p. administration of FL118, while the MTD that can be reached between i.v. and i.p. is very similar.

In terms of suitable FL118 administration schedules, from for instance the data provided in the Example 8, we can see the maximum tolerated doses (MTD) of FL118 formulated via Strategies I, II and III (Table 6) in mouse models are about 1.5 mg/kg in the daily×5 schedule (d×5), about 1.5 mg/kg in the every other day×5 schedule (q2×5), and 5 mg/kg in the weekly×4 schedule (wk×4). Without intending to be bound by any particular theory, based on our studies with FL118, more than once a day administration of FL118 is unnecessary and is not recommended because it does not significantly increase drug antitumor activity, while it significantly increases drug toxicity. On the other hand, more than weekly appears to further increase FL118 MTD.

In terms of clinical application of FL118 for cancer treatment, in addition to the three basic schedules (d×5, q2×5 and wk×4) other modified schedules based on the three defined basic schedules (d×5, q2×5 and wk×4) can be used. These include but are not necessarily limited to 1) d×5, every other week for three week administration of FL118 as one cycle, then approximately one month intervals, where a second and subsequent cycles could be performed depending upon continued improvement in outcome. Up to three cycles could be performed; 2) three time of q2×5 with one week interval between as one cycle; then approximately one month intervals; if the treatment yields favorable outcomes, another cycle could be performed. Up to three cycles can be applied; 3) every three day one time administration of FL118 for five time (q3×5) with a week to 10 days interval for three times as a cycle, with approximately one month between cycles; if the treatment shows favorable outcomes, another cycle could be applied. Up to three cycles can be applied; and 4) three time of wk×4 with approximately one month between each wk×4 for a cycle, and 2-3 cycles can be applied, which will depend on favorable outcomes. Additionally, the above four regimens can be used in combination among cycles to reach the best antitumor results with lowest toxicity to cancer patients.

With respect to the effective dose for FL118, it is an extremely potent anticancer drug when properly formulated as described herein. Although different schedules have different MTD, the MTD for FL118 in different schedules are all below 10 mg/kg in mouse models. In the daily schedule, MDT for FL118 is about 1.5 mg/kg. A sub-MTD of FL118 such as at 1.25 mg/kg, 1.0 mg/kg or 0.75 mg/kg for daily schedule still shows good antitumor activity. However, the percentage of human tumor in mouse models that are eradicated decreases. This is very similar to the situation in the data presented in FIGS. 6, 7, 8, 10, 14 and 15 with the wk×4 schedule. For these experiments, the FL118 formulation solution was generated using the initial formulation (0.05 mg/ml, Tween 80 20%, DMSO 5%, saline 75%) and was administrated via the i.p. route. However, it is important to note that with the initial FL118 formulation solution (0.05 mg/ml, Tween 80 20%, DMSO 5%, saline 75%), FL118 in the d×5 and q2×3 or q2×5 schedules was unable to reach a meaningful antitumor activity, because in these schedules the MTD for FL118 is too low (d×5, ~0.2 mg/kg; q2×3 or q2×5, ~0.5 mg/kg). In contrast, FL118 formulated via our novel formulation approaches (Strategy I, Strategy II and Strategy III; Table 6), the MTD for FL118 in d×5 and q2×5 schedules shifts from the 0.2-0.5 mg/kg in the initial formulation (0.05 mg/ml, Tween 80 20%, DMSO 5%, saline 75%) to 1.5-2.5 mg/kg, which show great antitumor activity and even eradicate tumor without relapse (FIGS. 30-32). The minimal dose for FL118 to show antitumor activity should not be less then 0.5 mg/kg for daily or longer schedule, as determined by the data presented herein.

Table 7 shows the comparative relationship of the FL118 MTD doses in different parameters/scales. for

TABLE 7

An example for the FL118 daily × 5 schedule at the 1.5 mg/kg (MTD) in mouse models*

| Subject | Body weight (kg) | Body surface area (sq. m) | Dose kg./day (mg) | Dose/sq. m/day (mg) |
| --- | --- | --- | --- | --- |
| Mouse | 0.018 | 0.0075 | 1.5 | 3.6 |
| Infant | 8 | 0.4 | 0.15 | 3.1 |
| Older Child | 20 | 0.8 | 0.12 | 3.1 |
| Adult | 70 | 1.85 | 0.07 | 2.7 |

*Adapted from Donald Pinkel: Cancer Research 18: 853-856, 1958.

The following Examples are intended to illustrate but not limit the invention.

Example 1

Compound Library and Drug Discovery

Compound Libraries Used for Drug Discovery:

The libraries of small molecular weight compounds used in this invention are from multiple resources including collaborative, self-developed compounds, proprietary compounds and compounds collected by NCI Developmental Therapeutics Program (DTP).

Processing of Drug Discovery:

More than 4000 structurally diverse small chemical molecular compounds were initially screened using genetically modified cancer cell models as described in U.S. Pat. No. 7,569,221. This screening resulted in about 250 hit compound candidates which showed effective downregulation of luciferase activity within 24 hours of compound treatment at a drug concentration of 1 µM, at which there is no significant cell death within 24 hours. Consecutive additional two round screening of the 250 hit candidates using a series of different concentrations (from 0.001 nM to 1000 nM) of the hit compounds resulted in 20 top-hit compounds, which showed inhibition of luciferase activity in a concentration range from 100 nM to 1 nM within 24 hours compound treatment. We further analyzed 207 analog compounds relevant to the 20 hit compounds in their chemical structure. FL118 is the highest scoring compound among the 207 analogs and shows unique MOA and unusual antitumor activity.

The compound FL118 is 10H-1,3-Dioxolo[4,5-g]pyrano[3',4':6,7]indolizino[1,2-b)]quinoline-8,11(7H,12H)-dione, 7-ethyl-7-hydroxy-, (S)- (chemical definition), and its corresponding NSC number is NSC634724

Example 2

Materials and Methods

Animals:

Six to 12-week-old female athymic nude mice (nu/nu, body weight 20-25 g) were purchased from Charles River Laboratories International, Inc. (Wilmington, Mass.) or Harlan Sprague Dawley Inc. (Indianapolis, Ind.). Six to 12-week-old female SCID mice were purchased from Roswell Animal facility (DLAR). Mice were housed at 5 mice per cage with water and food ad libitum. All animal experiments are performed in accordance with our IACUC-approved animal protocol.

Drugs and Control Solution (Vehicle):

FL118 was first dissolved in DMSO at a concentration of 1 mg/ml, and further diluted in a fresh Tween-80/saline solution. The final work solution consists of FL118 (0.05 mg/ml), 75% saline (V/V), 20% Tween-80 (V/V) and 5% DMSO (V/V). Control solution (placebo or vehicle) is 75% saline, 20% Tween-80 and 5% DMSO without FL118. Other FDA-approved anticancer drugs used in this invention for a comparison were used clinical formulations from the corresponding manufactures.

Tumors:

Human tumor xenografts were initially established by injecting s.c $1 \times 10^6$ cultured cancer cells. The xenografts were then passed several generations by transplanting 40-50 mg non-necrotic tumor tissues via a trocar from the passage tumors. Human primary tumors were initially obtained from cancer patients at Roswell Park Cancer Institute and established in SCID mice. Human tumor xenografts used in this study include human head & neck squamous cell carcinoma FaDu, human primary head & neck tumor 17073, human ileocecal adenocarcinoma HCT-8, human colon cancer SW620 and human primary colon cancer 11124 and 14528. Treatment was initiated 7 days after tumor transplantation when the tumor reaches 200-250 mg, at which the treatment was designated as Day 0. All cancer cells used for tumor establishment were tested for mycoplasma free. The transplantable tumor has similar histological profile of cultured cells.

Drug Doses and Schedule:

All drugs were administered by intraperitoneal injection (i.p.) or per oral (p.o.) at various doses (0.2-2 mg/kg). The following schedules were used: 1) i.p. daily×2: once a day for consecutive 2 days; 2) i.p. daily×3: once a day for consecutive 3 days; 3) daily×5: once a day for consecutive 5 days (i.p. or p.o.); 4) i.p.×3 (day 0, 2, 4): 3 times on day 0, 2, and 4; 5) i.p. 2 days/week×¾: 2 times a week for 3 or 4 consecutive weeks; 6) weekly×4: once a week for 4 consecutive weeks (i.p. or p.o.); 7) i.p. biweekly×4: once every two weeks for 8 weeks; 8) 2 days/week×4: give 2 times a week for 4 weeks; and 9) i.p.×1: one time drug i.p. injection on Day 0.

Tumor Measurement:

Two axes (mm) of a tumor (L, longest axis; W, shortest axis) were measured with a Vernier caliper. Tumor weight (mg) was estimated using a formula of "tumor weight=½ $(L \times W^2)$". Tumor measurement was taken daily for the first two weeks and/or during the FL118 treatment period (with the exception of weekend) and then three times a week for the following two weeks of post therapy and twice a week thereafter.

Maximum Tolerated Dose (MTD) and Toxicity Evaluation:

The MTD was defined as the highest drug dose causing no drug-related lethality in mice with a weight loss≤20% of original body weight with reversible toxicities. The kinetics of drug-induced toxicities (such as body weight loss, diarrhea, and lethality) were determined daily for the first two weeks upon treatment or during drug treatment if treatment is more than two weeks and, drug toxicity was evaluated every other day thereafter.

Antitumor Activity:

Antitumor activity was assessed by maximum tumor growth inhibition (MTGI), which is the mean tumor weight difference between treated group (MTWTG) and untreated control group (MTWCG) at the same time. The calculated formula is "MTGI=(MTWTG−MTWCG)÷MTWCG× 100%". The tumor doubling time (TDT) was defined as the mean time for the tumor reaching twice its initial weight from the time beginning the treatment (Day 0). Tumor response was expressed as 1) partial tumor response (PR) when tumor weight was reduced at least 50% initial tumor size on Day 0 and 2) complete tumor response (CR) which was defined as inability to detect tumor via palpitation at the initial tumor-transplanted site. The cure was defined as animals achieved CR and maintained tumor free for at least 30 days after the last time drug administration.

FL118 Shows Unusual and Surprising Antitumor Activity in Animal Models of Human Tumor Xenografts with Manageable Toxicity Antitumor Activity of FL118 is Superior to FDA-Approved Therapeutic Drugs Currently Used for Cancer Treatment in the Clinic:

To explore the anticancer efficacy potential of FL118, we compared antitumor activity of FL118 with those of FDA-approved therapeutic drugs including irinotecan and topotecan (topoisomerase I inhibitors), cisplatin and oxaliplatin (DNA platinating agents), docetaxel (microtubule polymerization promoter), gemcitabine and 5-FU (DNA synthesis inhibitors), doxorubicin (Topoisomerase II inhibitor) and Cytoxan (cyclophosphamide, alkylic agent). The results indicate that among all the tested compounds, FL118 showed surprising antitumor activity, which is strikingly superior to all the tested therapeutic drugs at the MTD in both head & neck and colon cancers (FIG. 1).

Figure 1:
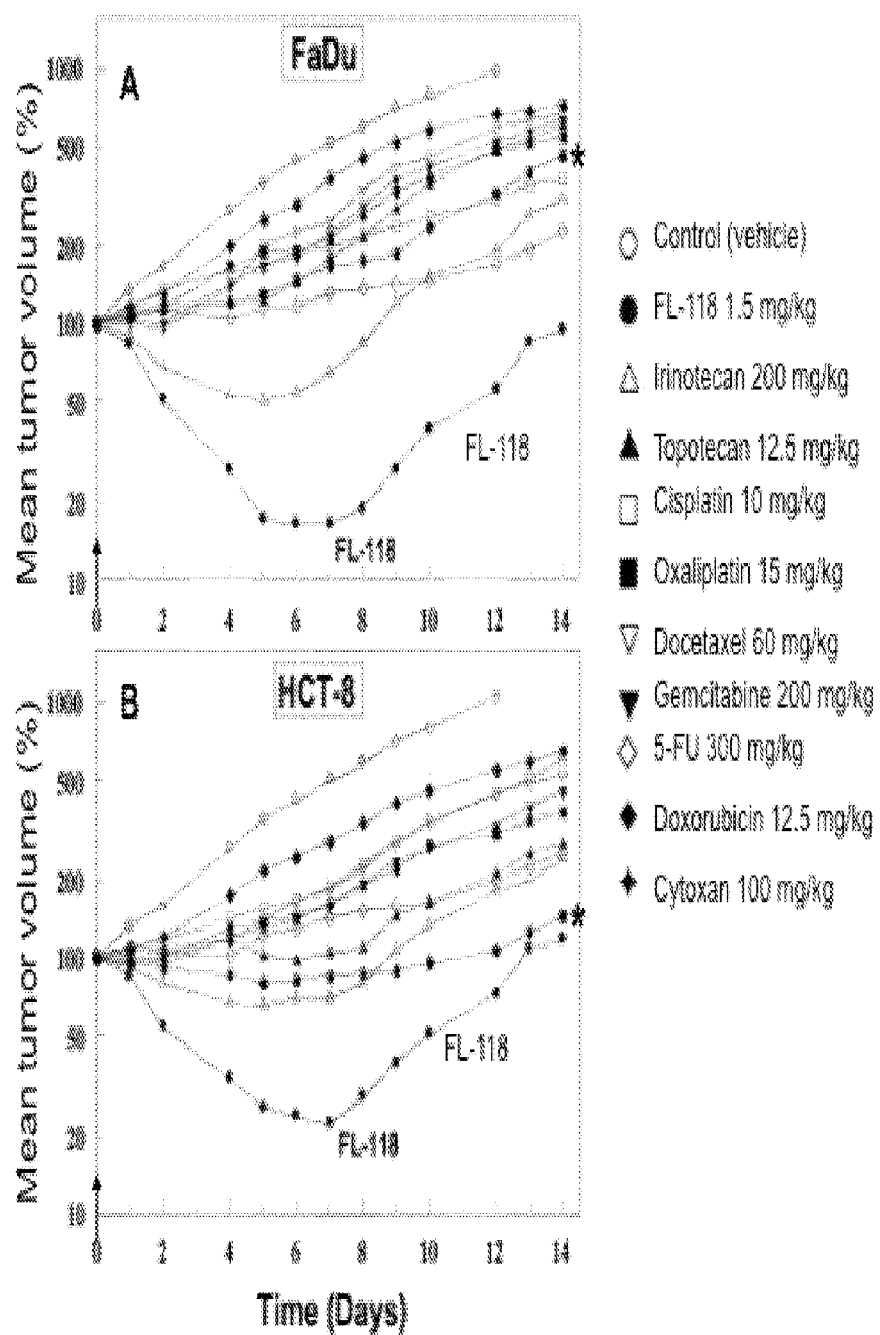
FIG. 1 FL118 shows superior antitumor activity in comparison with clinically used antitumor drugs: One-time intraperitoneal (i.p.) drug injection indicated by an arrow was performed at various doses as shown. The dose used for each of these drugs is roughly their maximum tolerated dose (MTD) for their single dose schedule. The FL118 dose is the MTD for its weekly×4 schedule. Treatment was initiated 7 days after tumor subcutaneous (s.c.) implantation, which was designated as Day 0 on which tumor weight is about 200-250 mg/mm$^3$. FaDu: Human head & neck tumor. HCT-8: Human colon tumor. Of note, the result from Cytoxan (cyclophosphamide) may over-represent its effectiveness (marked with *), since in this last experiment group (5 mice per group), the implanted tumor mass is smaller than required for other 10 groups (50 mice) due to insufficient tumor mass availability for implantation then. The tumor curve is the average from five tumors on five mice.
Figure 2:
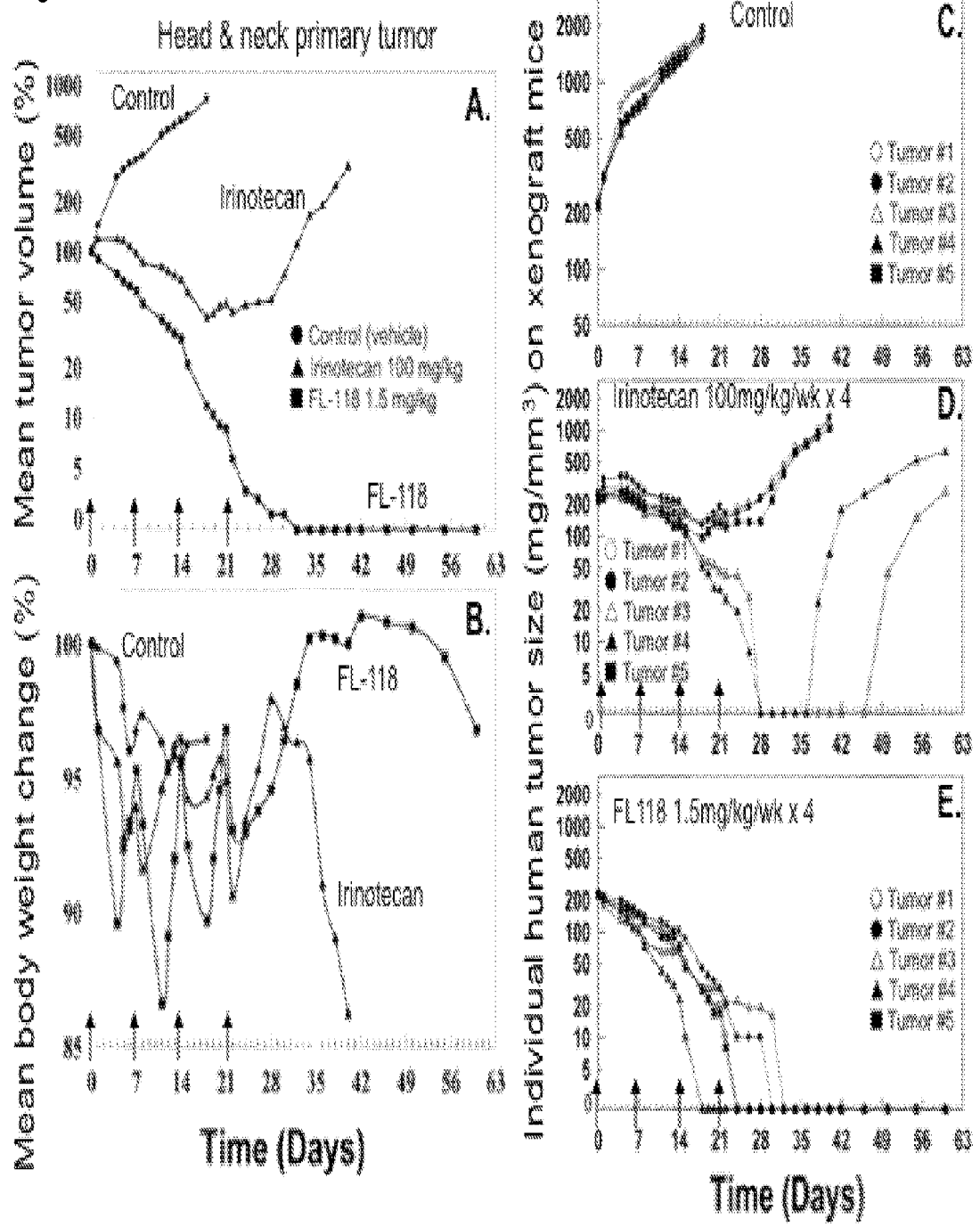
FIG. 2 Comparison of antitumor activity and toxicity (body weight loss) of FL118 with irinotecan in SCID mice bearing human 17073 primary head & neck xenografts: A and B. Antitumor activity and toxicity of FL118 and irinotecan against 17073 tumors. C, D and E. Individual 17073 tumor in response to FL118 and irinotecan. The treatment schedule was weekly×4 as indicated by arrows. The doses for FL118 and irinotecan were their MTD in the weekly×4 schedule.

FL118 but not Irinotecan Effectively Eradicates Human Primary Head & Neck Xenograft Tumor:

From data shown in FIG. 1, irinotecan is the second most effective compound against the experimental tumors. Both FL118 and irinotecan are structurally relevant to the camptothecin compound family and belong to camptothecin analogs. Therefore, we further compared antitumor activity of FL118 with irinotecan in a human primary head & neck tumor xenograft in SCID mouse models at their MTD using the clinical relevant schedule for irinotecan (weekly×4). The results showed that 2 out of 5 mice (40%) in the irinotecan-treated group showed complete response to irinotecan treatment. However, the tumor free period is short lived with rapid relapse. In contrast, in the FL118-treated group, 5 out of 5 mice (100%) showed complete response to FL118 treatment and no recurrent tumor was detected in all 5 mice during our experiment period (FIGS. 2D and 2E). Importantly, while irinotecan induced an accumulated body weight loss (reflect a long-term toxicity to normal tissues), FL118 only induced a temporary body weight loss with rapidly recovery after treatment (FIG. 2B).

Figure 3:
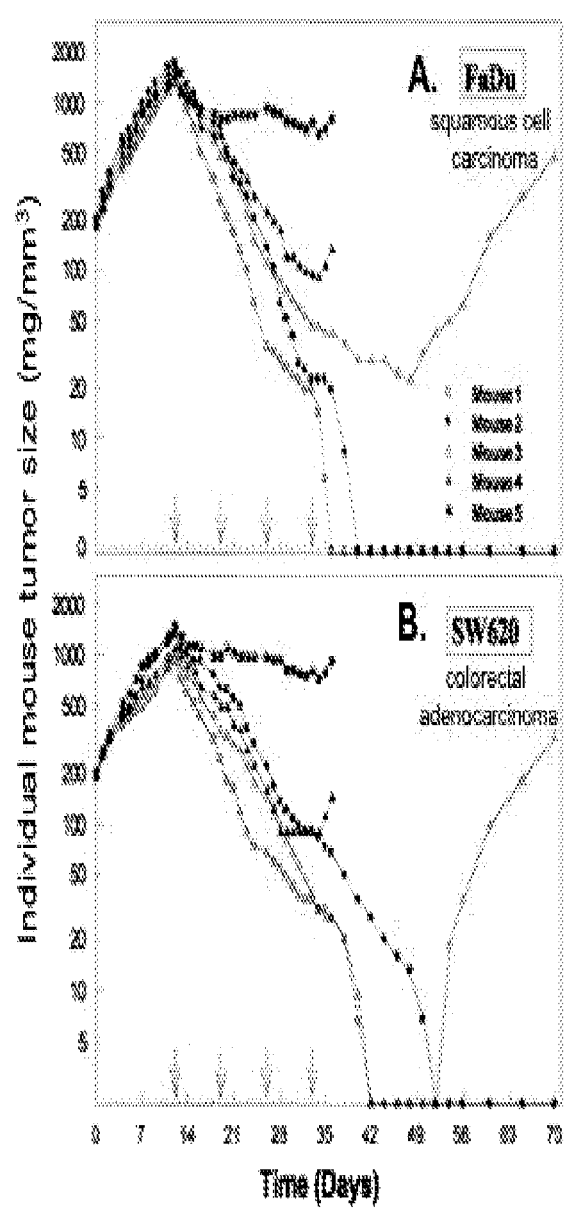
FIG. 3 Effect of FL118 on tumor growth inhibition with large tumors (1500-2000 mg/mm$^3$) of FaDu (head & neck cancer) and SW620 (colon cancer). The mice were treated with FL118 at the dose of 1.5 mg/kg once a week for 4 weeks as indicated by arrows. Two mice died on Day 37 for unclear reasons. One possibility is due to the rapid tumor breakdown after chemotherapy, which is known to be able to cause a life-threatening complication termed Tumor Lysis Syndrome (TLS). Consistent with this, the two died mice showed the largest tumor sizes at the time of initial treatment with FL118.

FL118 Effectively Eradicates Large and Later Stage Human Tumor Xenografts in Animal Models:

Generally speaking, large and late stage tumors respond poorly to chemotherapy. In contrast, mice bearing maximal human xenograft tumors allowed by IACUC (Institutional Animal Care and Use Committee) showed an unusual and surprising response to FL118 treatment in both FaDu head & neck tumors and SW620 colon tumors which could be even cured in many cases (FIG. 3).

FL118 is Functionally Stable and Shows Surprising Long Shelf Life.

Figure 4:
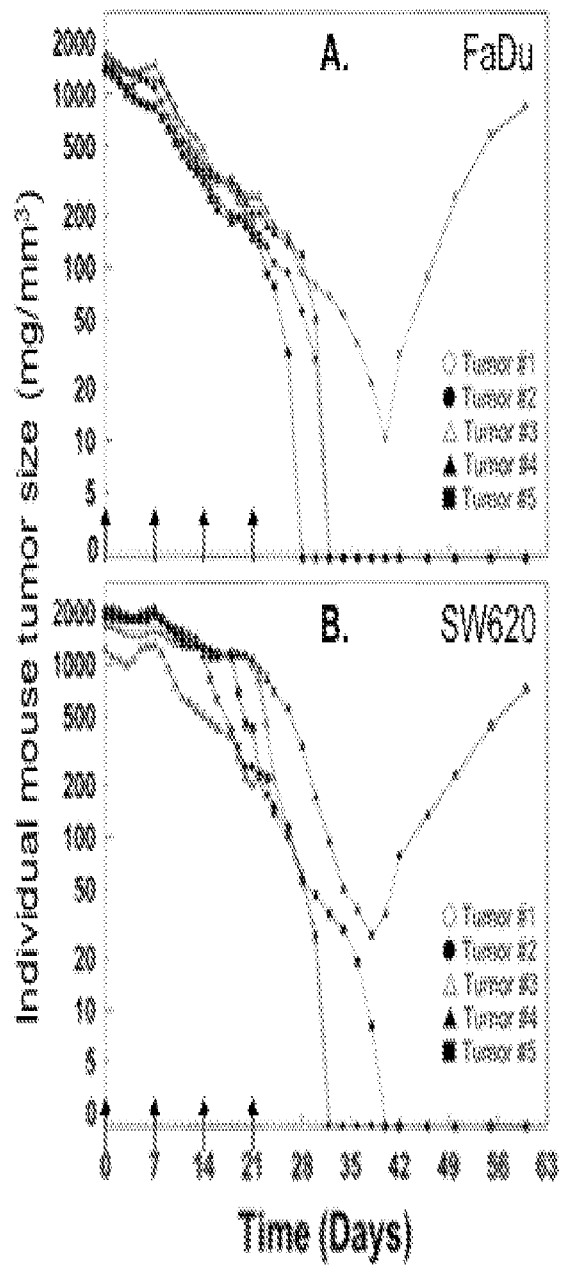
FIG. 4 The FL118 compound is functionally stable in the ready-to-use injection solution and may have a long shelf live. Athymic nude mice were xenografted with FaDu (head & neck cancer) and SW620 (colon cancer). After tumor mass grew to 1500-2000 mg/mm³, mice were weekly treated with a FL118 solution, which was formulated and stored at a 4° C. refrigerator for more than 6 months, at a dose of 1.5 mg/kg once a week for 4 weeks as indicated by arrows.

Using one formulation as an example (0.05 mg/ml in 75% saline+20% Tween 80+5% DMSO), to test the functional efficacy stability of FL118 in the final injection solution, a ready-to-use FL118 injection solution (0.05 mg/ml FL118, 75% saline, 20% Tween 80, 5% DMSO) was prepared and put in a +4° C. refrigerator for more than 6 months. The solution was then used for tumor treatment in human tumor mouse models. As shown in FIG. 4, FL118 showed as effective as newly prepared FL118 injection solution used in the experimental condition for the data shown in FIG. 3.

In summary, the data shown in FIGS. 1-4 demonstrate that the FL118 compound presented in this invention possesses unusual and surprising antitumor activity.

Example 3

Efficacy and Toxicity of FL118 at Different Doses, Routes and Schedules

Toxicity of FL118 to Animals Treated with Different Drug Doses, Schedules and Routes:

We discovered that toxicity of FL118 could be managed by different schedules and demonstrate that interval of administration of FL118, such as weekly or biweekly (but not daily) schedules at the given FL118 formulation (0.05 mg/ml FL118, 75% saline, 20% Tween 80, 5% DMSO), significantly diminished FL118 toxicity to animals. While the interval application of FL118 could lower FL118 toxicity in animals, at the same time, such approach increased its efficacy to inhibit tumor growth and eradicate tumor mass for a cure (FIGS. 1-4). Table 1 summarizes the toxicity profile of FL118 in nude mice at different doses and schedules with i. p. and p.o. routes. The diagram in FIG. 5 shows the toxicity profile of FL118 on its different doses and schedules in the i.p. route. The maximum tolerated dose (MTD) of FL118 via the i.p. and p.o. routes is shown in Table 2.

TABLE 1

Toxicity induced by FL-118 in nude mice

| Drug | Dose (mg/kg) | Schedule | Mice No[1] | Weight loss | Lethality |
|---|---|---|---|---|---|
| FL-118 | 0.75 | i.p. daily × 2 | 5 | 13.7 ± 11.0 | 20 |
| FL-118 | 0.50 | i.p. daily × 3 | 5 | 30.7 ± 4.2 | 100 |
| FL-118 | 0.75 | i.p. daily × 3 | 5 | 31.4 ± 2.3 | 100 |
| FL-118 | 0.20 | i.p. daily × 5 | 10 | 13.0 ± 3.7 | 0 |

TABLE 1-continued

Toxicity induced by FL-118 in nude mice

| Drug | Dose (mg/kg) | Schedule | Mice No[1] | Weight loss | Lethality |
|---|---|---|---|---|---|
| FL-118 | 0.30 | i.p. daily × 5 | 5 | 29.0 ± 5.6 | 80 |
| FL-118 | 0.40 | i.p. daily × 5 | 5 | 35.1 ± 4.2 | 100 |
| FL-118 | 0.50 | i.p. × 3 (day 0, 2, 4) | 15 | 8.7 ± 4.9 | 0 |
| FL-118 | 0.60 | i.p. × 3 (day 0, 2, 4) | 5 | 27.6 ± 13.4 | 80 |
| FL-118 | 0.75 | i.p. × 3 (day 0, 2, 4) | 5 | 30.3 ± 8.2 | 80 |
| FL-118 | 0.75 | i.p. 2 days/wk × 3 | 5 | 27.9 ± 7.6 | 60 |
| FL-118 | 0.50 | i.p. 2 days/wk × 3 | 5 | 13.3 ± 4.3 | 0 |
| FL-118 | 0.50 | i.p. weekly × 4 | 5 | 9.8 ± 5.7 | 0 |
| FL-118 | 0.75 | i.p. weekly × 4 | 10 | 9.1 ± 3.8 | 0 |
| FL-118 | 1.00 | i.p. weekly × 4 | 15 | 12.2 ± 4.8 | 0 |
| FL-118 | 1.25 | i.p. weekly × 4 | 10 | 12.1 ± 6.8 | 0 |
| FL-118 | 1.50 | i.p. weekly × 4 | 15 | 15.1 ± 3.7 | 0 |
| FL-118 | 1.75 | i.p. weekly × 4 | 5 | 29.0 ± 6.7 | 80 |
| FL-118 | 0.75 | p.o. daily × 5 | 5 | 30.5 ± 7.5 | 80 |
| FL-118 | 2.00 | p.o. weekly × 4 | 5 | 10.6 ± 5.8 | 0 |

[1]Five mice were used for each experimental group.

TABLE 2

The Maximum tolerated Dose (MTD) of FL-118

| Schedule | Route | Mice | MTD (mg/kg/dose) |
|---|---|---|---|
| Daily × 5 (5 doses) | i.p. | Nude & SCID | 0.2 |
| Daily × 3 (3 doses) | i.p. | Nude | <0.5 |
| Day 0, 2, & 4 (3 doses) | i.p. | Nude | 0.5 |
| 2 days/week × 4 (8 doses) | i.p. | Nude | 0.5 |
| Weekly × 4 (4 doses) | i.p. | Nude & SCID | 1.5 |
| Daily × 5 (doses) | p.o. | SCID | 0.6 |
| Weekly × 4 (4 doses) | p.o. | Nude | ≥2.0 |

Results from Human Head & Neck Cancer Animal Model:

FL118 showed unusual and surprising efficacy for treatment of human head & neck cancer. For example, the FaDu head & neck cancer cell line-established tumor was cured for 40% (2 out of 5 mice) by FL118 at 0.75 mg/kg (half of MTD) with a schedule of weekly×4 via i.p. administration of drug (FIG. 6); the FaDu tumor was cured for 60% (6 out of 10 mice) by FL118 at a dose of 1 mg/kg (a dose under MTD) with the same schedule of weekly×4 via i.p. injection (FIG. 7B) and, 70% (7 out of 10 mice) FaDu tumor was cured by FL118 at a dose of 1.25 mg/kg (a dose close to but still under MTD) with the same schedule of weekly×4 via i.p. injection (FIG. 8B). Treatment of FaDu-derived head & neck tumor on athymic nude mouse models with FL118 at the dose of 1.5 mg/kg with the schedule of weekly×4 showed that 4 of 5 mice resulted in a cure without relapse, while one showed a temporary cure with relapse (FIG. 9). Table 3 summarizes these experiments.

TABLE 3

Antitumor activity of FL-118 in nude mice bearing human FaDu head and neck tumor xenografts

| TREATMENT | ANTITUMOR ACTIVITY | | | | |
|---|---|---|---|---|---|
| | MTGI (%) | TDT (day) | PR (%) | CR (%) | Mice # |
| Control (vehicle) | — | 3.6 ± 0.4 | 0 | 0 | 20 |
| FL-118 0.75 mg/kg, i.p. weekly × 4 | 96.7 ± 3.9 | 29.2 ± 6.6 | 40 | 40 | 5 |
| FL-118 1.00 mg/kg, i.p. weekly × 4 | 96.7 ± 5.4 | 42.8 ± 12.6 | 40 | 50 | 10 |
| FL-118 125 mg/kg, i.p. weekly × 4 | 98.4 ± 3.6 | 48.8 ± 13.2 | 20 | 70 | 10 |
| FL-118 1.50 mg/kg, i.p. weekly × 4 | 100 | >80 | 20 | 80 | 5 |
| FL-118 2.0 mg/kg, p.o. weekly × 4 | 96.4 ± 3.4 | 36.2 ± 17.8 | 60 | 20 | 5 |

MTRI: maximum tumor growth inhibition;
TDT: tumor doubling time;
PR: partial tumor response;
CR: complete tumor response.
Treatment was initiated 7 days after the tumor transplantation when the tumor weight reaching ~200 mg (mm$^3$ in size). Control mice were given vehicle solution (75% saline, 20% Tween-80 and 5% DMSO). Five mice were used for each one experimental group.

Results from Human Colon Cancer Animal Model:

FL118 also showed outstanding efficacy for human colon cancer. Table 4 summarizes the results derived from different doses for FL118 treatment of nude mice bearing human HCT-8 and SW620 colon tumor xenografts.

TABLE 4

Antitumor activity of FL-118 in nude mice bearing human HCT-8 and SW620 colon tumor xenografts

| TREATMENT | ANTITUMOR ACTIVITY | | | | |
|---|---|---|---|---|---|
| | MTGI (%) | TDT (day) | PR (%) | CR (%) | Mice # |
| HCT-8 | | | | | |
| Control (vehicle) | — | 3.3 ± 0.4 | 0 | 0 | 20 |
| FL-118 0.75 mg/kg, i.p. weekly × 4 | 95.0 ± 4.2 | 29.9 ± 9.4 | 40 | 20 | 10 |
| FL-118 1.00 mg/kg, i.p. weekly × 4 | 90.9 ± 4.8 | 41.6 ± 12.2 | 60 | 20 | 10 |
| FL-118 1.25 mg/kg, i.p. weekly × 4 | 92.5 ± 8.2 | 42.2 ± 12.8 | 40 | 20 | 5 |
| FL-118 1.50 mg/kg, i.p. weekly × 4 | 98.3 ± 2.1 | 65.2 ± 9.8 | 40 | 50 | 10 |
| Irinotecan 100 mg/kg, i.p. weekly × 4 | 94.1 ± 3.6 | 32.7 ± 11.5 | 60 | 0 | 5 |
| SW620 | | | | | |
| Control (vehicle) | — | 5.0 ± 0.6 | 0 | 0 | 10 |
| FL-118 0.75 mg/kg, i.p. weekly × 4 | 98.8 ± 1.6 | 37.5 ± 9.6 | 40 | 60 | 5 |
| FL-118 1.00 mg/kg, i.p. weekly × 4 | 95.3 ± 6.0 | 42.1 ± 10.6 | 60 | 20 | 10 |
| FL-118 1.25 mg/kg, i.p. weekly × 4 | 100 | 48.8 ± 13.2 | 50 | 50 | 5 |
| FL-118 1.50 mg/kg, i.p. weekly × 4 | 99.2 ± 1.1 | >80 | 40 | 60 | 5 |
| FL-118 2.0 mg/kg, p.o. weekly × 4 | 91.5 ± 7.5 | 34.20 ± 19.5 | 60 | 0 | 5 |

We have also determined antitumor activity of FL118 in two human colon primary tumors in SCID mice. Antitumor activity and toxicity of FL118 at a dose of 1 mg/kg and of irinotecan at MTD in the best schedule of weekly×4 for irinotecan are compared and the outcome is shown in FIG. 10, which reveals that FL118 is superior to irinotecan.

Antitumor Activity and Toxicity of FL118 and Irinotecan in Human Lung Cancer Animal Models:

The A549 lung cancer cell line-established tumors were treated with FL118 and irinotecan at their MTD with a schedule of weekly×4 via i.p. administration. As shown, FL118 has a significant better antitumor activity in comparison with irinotecan (FIG. 11), while their toxicity is comparable.

Oral Administration (p.o.) of FL118 Shows Significant Antitumor Activity:

For development of a new anticancer drug like FL118, oral administration of drug provides an attractive advantage. This is because the p.o. route offers more convenience than i.v. routes for cancer patients, greatly saves medical costs by reducing times of hospital stay, provided comparable antitumor activity and toxicity can be achieved. Therefore, we have determined antitumor efficacy and toxicity with the clinically favorable p.o. route for FL118. Studies using both human cancer cell line-derived and primary head & neck and colon cancer animal models demonstrated that FL118 shows significant antitumor activity via p.o. routes. These data are shown in FIGS. 12-14. The body weight changes in the FL118-treated groups in comparison with the body weight changes in the vehicle-treated group shown in FIGS. 12 and 13 suggest that the MDT of FL118 is higher than 2 mg/kg via p.o. with this schedule.

Anticancer Activity of FL118 is Highly Associated with its Unique Steric Structure:

FL113 [10H,12H-1,3-Dioxolo[4,5-g]pyrano[3',4':6,7]indolizino[1,2-b]quinoline-8,11(7H,10H)-dione, 7-ethyl-7-hydroxy-, (+-) (chemical definition); NSC606174 (NSC number)] has the same molecular weight (MW, 392) as FL118 [10H-1,3-Dioxolo[4,5-g]pyrano[3',4':6,7]indolizino[1,2-b]quinoline-8,11(7H,12H)-dione, 7-ethyl-7-hydroxy-, (S)- (chemical definition); NSC634724 (NSC number)] has. However, FL118 has a distinct steric structure that is different from FL113 (FIG. 15A). Due to the steric structure difference between FL118 and FL113, FL118 shows its antitumor activity in the human tumor mouse models much better than those of FL113, although FL113 antitumor activity is better than irinotecan in most cases. A representative example is shown in FIG. 15.

Example 4

Effects of FL118 in Combination with Chemotherapeutic Agents on Cancer Cells Materials and Methods Cancer Cell Lines Used:

HCT-8 colon cancer cells, A2008 and Skov3 ovarian cancer cells were maintained in DMEM, supplemented with 10% fetal bovine serum (Mediatech Cellgro, Herndon, Va.) and penicillin (100 units/ml)/streptomycin (0.1 µg/ml) (Invitrogen, Grand Island, N.Y.) in a humidified incubator with 5% CO2 at 37° C. Cells were routinely subcultured every 3-4 days.

MTT Cell Growth/Viability Assay:

Cell growth and viability with and without FL118 and taxol treatment was determined by MTT assay. A tetrazolium salt, 3-[4,5-dimethylthiazol-2-yl]-2,5-diphenyltetrazolium bromide (MTT), was used as a colorimetric substrate for measuring cell viability. Non-viable cells, with altered cellular redox activity, are unable to reduce the MTT dye. After 72 hours with or without bortezomib treatment, MTT was added (to a final concentration of 0.5 mg/ml). Cells in 96-well plates were incubated in a 5% $CO_2$ incubator at 37° C. for 4 hours, and then lysed thoroughly with lysis buffer (20% SDS, 50% N,N-dimethylformamide, pH 4.7, 100 µl/well). The absorbance in the relevant wells was measured at 570 nm using an Ultra Microplate Reader (Bio-Tek Instruments).

FL118 can be Used Effectively in Combination with Other Chemotherapeutic Agents

The novel drug action mechanism of FL118 described further below prompted us to explore its potential for cancer treatment in combination with other classic chemotherapeutic and chemopreventive agents. In this regard, we tested a series of chemotherapeutic and chemopreventive compounds in combination with FL118. Results from example drug combinations are presented below.

Treatment of HCT-8 Colon Cancer Cells with FL118 in Combination with Cisplatin Produced Significant Better Results than Each Compound Alone:

HCT-8 colon cancer cells were grown in normal cell growth medium treated with a series of FL118 concentration alone or in combination with cisplatin at different concentrations. Cell growth/survival were determined 72 hours after treatment. Surprisingly, such combination resulted in a great inhibition of cancer cell growth in a wide range of drug concentration (FIG. 16).

Treatment of Cancer Cells with FL118 in Combination with Etoposide, Taxol or Doxorubicin Shows Positive Results:

Due to the unique MOA for FL118, it is expected that many classic chemotherapeutic drugs could be used in combination with FL118 for cancer treatment. Most classic chemotherapeutic compounds have distinct drug action mechanism from those of FL118. Therefore, distinct MOA from two compounds demonstrates cooperative (additive or synergistic) action, although there are possible exceptions. In this regard, FL118 combination with cisplatin (FIG. 16), etoposide (FIG. 17), taxol (FIG. 18) or doxorubicin (FIG. 19) shows promising results. In addition, we also observed positive effects of FL118 in combination with 5-FU, Gemzar, resveratrol and 5-aza-deoxycytidine in certain defined drug concentration (not shown). Of note, the last two compounds (resveratrol and 5-azacytidine) are known to downregulate survivin, which may therefore mechanistically overlap in part with FL118 MOA.

Example 5

Mechanism of Action (MOA)-FL118 Acts as an IAP and Bcl-2 Family Antiapoptotic Proteins-Selective Inhibitor Materials and Methods Luciferase Activity Assay:

Cells were seeded in 48-well plates ($2.5 \times 10^4$ per well) and grown at approximately 60-70% confluence in complete cell cultural medium containing 10% fetal bovine serum (FBS) in all experiments. Cells were either stably transfected with the pLuc-6309 survivin promoter-luciferase construct or untransfected cells or transiently transfected with relevant luciferase reporter vectors indicated in the data as follows: Briefly, 245 ng of targeting luciferase reporter constructs plus 5 ng of internal control vector, pRK-tk in 30 µl serum-free DMEM was mixed in a 1.5 ml tube containing 30 µl serum-free DMEM containing 0.4 Lipofectamine™ 2000. After incubation at room temperature for 20-25 minutes, the DNA/Lipofectamine 2000 mixture (60 µl) was added to each well of 48-well plates, which already contained 300 µl corresponding complete growth medium. The DNA/Lipofectamine 2000 mixture was replaced after incubation for 16 hours by new complete growth medium containing either DMSA or FL118. Cells were treated with FL118 up to 24 hours, followed by processing for luciferase assays. For the luciferase assay, a Dual-Luciferase Reporter Assay System (Promega) was used. The transfected cells in 48-well plates were washed with PBS and lysed with 60 µl 1× passive lysis buffer on a shaker for up to 1 hour at 4° C. Twenty µl cell lysate per well was used to measure the Firefly and *Renilla luciferase* activity in a Luminometer by subsequently adding 20 µl luciferase assay reagent and 20 µl Stop-Glo reagent. Data were normalized to *Renilla luciferase* activity (internal control) as arbitrary units and plotted as histogram.

MTT Cell Growth/Viability Assay:

Performed as described above.

Western Blot Analysis:

Western blot analysis of phosphorylated or unphosphorylated protein expression was performed as follows. Cells with and without drug treatment were washed with phosphate-buffered saline (PBS) and lysed on ice for 30 minutes in PBS containing 1% Nonidet P-40, 0.5% sodium deoxycholate, 0.1% sodium dodecyl sulfate (SDS), 10 µg/ml phenylmethyl sulfonyl fluoride, and 20 µM leupeptin. Cell lysates were then centrifuged at 15,000 g for 20 minutes at 4° C. Fifty µg total proteins from each sample were heated at 95° C. for 5 minutes after mixing with equal volume of 2×SDS loading buffer. Samples were separated on 12-15% SDS-polyacrylamide gel electrophoresis (SDS-PAGE) gels and electrotransferred to Pure Nitrocellulose Membranes (Bio-Rad, Hercules, Calif.). The membrane was then blocked in 5% skim milk in TBS-T buffer (20 mM Tris/HCl (pH 7.5), 0.137 M NaCl, and 0.05% Tween 20) at room temperature for 2-3 hours; followed by incubation of the membrane with relevant primary antibodies with appropriate dilution (500× to 5000×) in TBS-T containing 5% BSA overnight at 4° C. After washing with TBS-T, the membrane was incubated in TBS-T buffer containing 5% skim milk containing the corresponding secondary antibody (1:5000) for 45-60 minutes at room temperature with shaking. Protein of interest was detected using Western Lightning®-ECL (Perkin Elmer, Waltham, Mass.) and visualized by autoradiography with various times (5-60 seconds) of exposure. Actin was detected as the internal control for normalization of total protein loading in each lane.

Topoisomerase I (Top1) Assay:

Effects of FL118 on Top 1 activity were determined using a Topoisomerase I Assay Kit from TopoGEN (Port Orange, Fla.) following the protocol supplied by the manufacture. Effects of FL118 on Top1 activity was determined by FL118's ability to block Top1 to process supercoiled plasmid DNAs into relaxed plasmid DNAs. Each reaction contains one unit of Top1, 0.625 µg supercoiled plasmid DNA substrates, 10 mM Tris-HCl (pH7.9), 1 mM EDTA, 150 mM NaCl, 0.1% bovine serum albumin (BSA), 100 µM spermidine and 5% glycerol. The reaction was supplied with or without FL118 or SN-38 (the active form of irinotecan, a known Top1 inhibitor which can be processed in vivo but not in vitro). Incubations were carried out at 37° C. for 30 minutes and the reaction was stopped by adding 5 µl stop buffer/gel loading dye. The plasmid DNAs in each reaction were separated by electrophoresis in a 1% agarose gel in 1×TAE buffer and stained for 15 minutes in 1×TAE buffer containing 0.5 µg/ml ethidium bromide. An electronic image was taken under an ultraviolet light.

FL118 Possesses Unique Mechanism of Action (MOA)

FL118 Selectively Inhibits Survivin Promoter Activity:

FL118 effectively inhibits human survivin promoter-driven luciferase activity in A2008 ovarian cancer cells (FIG. 20) but shows no inhibitory effects on luciferase activity driven by gene promoters for the cyclin-dependent kinase inhibitor p21 (p21), dihydrofolate reductase (DHFR), human thrombin receptor (HTR) and thymidine kinase (TK) in either EKVX lung cancer cells (FIG. 21A) or LNCaP prostate cancer cells (FIG. 21B). Similar results were obtained in PC-3 prostate cancer cell as well (FIGS. 22 A and B). Importantly, consistent with these results, while FL118 selectively inhibits endogenous survivin expression, it shows no inhibitory effects on the endogenous expression of p21 and DHFR (FIGS. 22 C and D). These data indicate high specificity for FL118 for inhibition of survivin gene transcription.

FL118 Inhibits the Expression of Multiple Antiapoptotic Proteins in the IAP and Bcl-2 Families.

We tested whether the superior survivin expression inhibitor activity of FL118 not only inhibits survivin expression, but would also inhibit other antiapoptotic protein expression in the IAP/Bcl-2 families. Consistent with this, using commercially available antibodies we showed in western blots that FL118 inhibits the expression of survivin, XIAP, cIAP2 and Mcl-1, while it only showed a minimal effect on Bcl-2 and Bcl-XL (FIG. 23). In contrast, FL118 increases the expression of pro-apoptotic proteins (Bax, Bim), possibly including survivin-2B marked by an asterisk (FIG. 23), indicating its high selectivity.

FL118 Induces Apoptosis:

Consistent with our demonstration that FL118 differentially regulates the expression of pro-survival and proapoptotic proteins in the IAP and Bcl-2 families (FIG. 23), modulation of the expression of these proteins in the IAP/Bcl-2 families by FL118 is associated with caspase activation and PARP cleavage (FIG. 24), which are hallmarks of apoptosis.

FL118 Inhibits Cancer Cell Survival Akt Signaling, while it Shows No Inhibitory Effects on Erk1/2 Signaling:

Another unique feature of FL118 is that it inhibits both constitutive and taxol-induced Akt activation, while it shows no inhibitory effect on Erk signaling (FIG. 25), indicating its high selectivity and unique MOA. In addition to the foregoing data, FL118 is between 10 and 100 fold more effective than taxol for ablation of cancer cell viability (FIG. 26), which is consistent with the data from human tumor xenograft animal models presented herein. Additionally, one known MOA for camptothecin (CPT)-related compounds is their ability to inhibit topoisomerase I (Top1) activity. We compared the ability of FL118 and SN-38 (the active form of irinotecan, a known Top1 inhibitor) to inhibit Top1 activity; the result indicated that as high as 1 µM concentration of FL118 only shows a weak inhibitory effect on Top1 activity (about half of those of SN-38, FIGS. 27 A and B). In contrast, FL118 at a low nM level effectively inhibits cancer cell growth (FIGS. 27 C and D) and induces apoptosis (FIG. 24). Therefore, the weak inhibition of Top1 activity by FL118 in high concentration likely plays little role in FL118-mediated inhibition of cancer cell growth and induction of apoptosis. Additionally, the dose used for FL118 [0.75 (50% MTD)-1.5 (MTD) mg/kg] in animal models is about 100 fold lower than the dose used for irinotecan (100-200 mg/kg). Therefore, this is consistent with the notion that the minor effect of FL118 at high concentration on Top1 activity makes little contribution to the MOA and antitumor activity of FL118 if any, especially considering the results from SN-38 control compounds.

Example 6

Novel Formulations for Water-Insoluble Drugs or Drug Candidates, Method of Making Thereof, and Method of Using Thereof for Treating Diseases The following description provides a summary of extensive but unsuccessful efforts to develop formulations for use as pharmaceutical drug preparations, including FL118, for clinically relevant in vivo applications.

Ten compounds were selected from a compound pool for testing water-insoluble compound formulations (FIG. 28). While these compounds are structurally diverse with linear and non-linear dimensional characteristics, they share the property of being water-insoluble or having extremely low water solubility.

Our initial goal for drug formulation with these compounds was to find an i.p. acceptable formulation in order to be able to test these and other compounds for antitumor activity in animal models. Our testing revealed that all of these drug candidates could be dissolved in DMSO (dimethyl sulfoxide) at a range of 1-3 mg/ml. Therefore, our initial approach was to use an aqueous humor (e.g. water, saline or phosphate-buffered saline) to dilute the individual drug candidates that we determined were dissolved well in DMSO in the defined range. However, these approaches were unsuccessful because the drug candidates come out of the solution during the dilution process with the aqueous humor (e.g. water, saline or phosphate-buffered saline). Subsequent to this testing, we attempted to use an aqueous humor (e.g. saline) with an emulsifier (e.g. Tween 80/Polysorbate 80) to dilute the drug candidates dissolved in DMSO. We determined that increasing the percentage of Tween 80 improved the solubility of the drug. To restrict Tween 80 to an acceptable percentage for clinical applications, the final formulation solution was prepared using DMSO (5%), Tween 80 (20%) and saline (75%). To illustrate this process with FL118 as an example, since FL118 can be dissolved in DMSO at about 1 mg/ml (which is approximately the saturated concentration for FL118 in DMSO), when 5 ml DMSO containing 5 mg FL118 (an example) is diluted in 95 ml pre-mixed aqueous humor (20 ml Tween 80+75 ml saline), the final FL118 solution for i.p. administration contains FL118 (0.05 mg/ml), DMSO (5%), Tween 80 (20%) and saline (75%), which is the FL118 formulation used for i.p. injection for the data presented in FIGS. 1-15 and Tables 1-4. For this formulation, up to 0.6 ml formulated solution without drug (placebo, vehicle or control solution) for a 20 g mouse in i.p. routes showed little toxicity to nude or SCID mice. In parallel, up to 0.8 ml of this formulation solution for a 20 g mouse in oral routes showed little toxicity to mice. However, this formulation (saline 75%+Tween 80 20%+DMSO 5%) is not a suitable formation because of two inherent issues for water-insoluble drug formulation. First, the drug concentration in the formulation solution is too low and could not reach an acceptable higher concentration, and thus for the less potent compounds (e.g. irinotecan MTD is 100-200 mg/kg), this formulation cannot be used for drug evaluation in animal models. Second, the percentage of Tween 80 in the formulation is too high, and for clinically compatible delivery routes, such as the i.v. route, Tween 80 is not a favorable formulation solvent and it would be desirable to obviate the requirement for Tween 80 or other similar reagents.

Based on the foregoing and in consideration of i.p. injection of drug in clinical practice is rare (with certain exceptions, such as for ovarian cancer), finding a formulation for administration of water-insoluble compounds for drug evaluation in animal models via i.v. routes (which would inherently be compatible with the routes of i.p. and oral) delivery with less or no Tween 80, is important for testing drug candidates inn animal models using clinical compatible routes (i.v. and per oral) and thus to facilitate further drug testing in clinical trials and used to treat patients. In order to identify a suitable formulation for administration of FL118 via the i.v. route with less toxicity, we analyzed multiple additional solvents in combination with DMSO with the water-insoluble drug candidates with diverse chemical structures depicted in the FIG. 28. These solvents included DMSO, ethanol, propylene glycol (PG), polyethylene glycol 300 or 400 (PEG 300 or PEG 400), glycerin and a type of cyclodextrin (CD)-βCD, hydroxypropyl-β-cyclodextrin (HPβCD) or sulfobutylether-β-cyclodextrin (SBEβCD). The water-insoluble drug candidates were tested using either DMSO or ethanol as leading solvents (dimethylformamide or DMF, was not considered, since DMF is a FDA-unfavorable solvent for use in human) to evaluate whether the drug candidate is able to partially dissolve in an acceptable concentration, even if at a low level (e.g. <0.5 mg/ml). If both leading solvents partially dissolve a water-insoluble drug candidate (FIG. 28), we chose the solvent that dissolves the drug candidate better. For example, FL113 and FL118 are poorly dissolved in ethanol but are able to be dissolved in DMSO, although with a relative low concentration (about 1 mg/ml). So DMSO instead of ethanol was chosen for FL113 and FL118 initial formulation as their leading solvent. Independently, a separate water-based cosolvent mixture is made via mixing an aqueous humor (e.g. distilled water, saline or phosphate-buffered saline) with helper cosolvents (PG, PEG 400 or a type of CD). Specifically, in simple combinations for helper cosolvent mixtures: Recipe 1) saline with 5% PG (Solution 1), saline with 10% PG (Solution 2), saline with 15% PG (Solution 3), saline with 20% PG (Solution 4), saline with 25% PG (Solution 5); Recipe 2) saline with 5% PEG 400 (Solution 1), saline with 10% PEG 400 (Solution 2), saline with 15% PEG 400 (Solution 3), saline with 20% PEG 400 (Solution 4), saline with 25% PEG 400 (Solution 5), saline with 30% PEG 400 (Solution 6); Recipe 3) saline with 5% glycerin (Solution 1), saline with 10% glycerin (Solution 2); Recipe 4) saline with 2.5% HPβCD (Solution 1), saline with 5% HPβCD (Solution 2), saline with 10% HPβCD (Solution 3), saline with 15% HPβCD (Solution 4), saline with 20% HPβCD (Solution 5), saline with 25% HPβCD (Solution 6), saline with 30% HPβCD (Solution 7), saline with 35% HPβCD (Solution 8), saline with 40% HPβCD (Solution 9). In complex combination: Recipe 5) saline with 2.5% PG/2.5% PEG 400 (Solution 1), saline with 2.5% PG/5% PEG 400 (Solution 2), saline with 5% PG/2.5% PEG 400 (Solution 3), saline with 5% PG/10% PEG 400 (Solution 4), saline with 10% PG/5% PEG 400 (Solution 5), saline with 10% PG/10% PEG 400 (Solution 6), saline with 15% PG/15% PEG 400 (Solution 7); Recipe 6) saline with 5% PG/5% HPβCD (Solution 1), saline with 5% PG/10% HPβCD (Solution 2), saline with 10% PG/10% HPβCD (Solution 3), saline with 10% PG/15% HPβCD (Solution 4), saline with 10% PG/20% HPβCD (Solution 5), saline with 10% PG/25% HPβCD (Solution 6); Recipe 7) saline with 5% PEG 400/5% HPβCD (Solution 1), saline with saline with 5% PEG 400/10% HPβCD (Solution 2), saline with 5% PEG 400/15% HPβCD (Solution 3), saline with 5% PEG 400/20% HPβCD (Solution 4), saline with 10% PEG 400/20% HPβCD (Solution 5), saline with 10% PEG 400/25% HPβCD (Solution 6); Recipe 8) saline with 2.5% PG/2.5% PEG 400/5% HPβCD (Solution 1), saline with 2.5% PG/2.5% PEG 400/10% HPβCD (Solution 2), saline with 2.5% PG/2.5% PEG 400/15% HPβCD (Solution 3), saline with 2.5% PG/2.5% PEG 400/20% HPβCD (Solution 4), saline with 5% PG/5% PEG 400/10% HPβCD (Solution 5), saline with 5% PG/5% PEG 400/20% HPβCD (Solution 6), saline with 5% PG/5% PEG 400/25% HPβCD (Solution 7). Such tests are performed to determine if a partially dissolved drug candidate in a leading solvent (DMSO or ethanol) will significantly increase its solubility when a water insoluble drug candidate partially dissolved in a leading solvent (DMSO or ethanol) is diluted with a water-based helper cosolvent mixture (i.e. Embodiments Recipe1-8). Using FL118 as an example, 5 mg FL118 (for example) is partially dissolved in 1 ml DMSO (only about 20% of FL118 is able to dissolve). Then the 1 ml DMSO mixed with 5 mg FL118 is diluted in 19 ml water-based helper cosolvent mixture of the Embodiments 1 to 8, respectively, to make a solution containing 0.25 mg/ml FL118, 5% DMSO and helper cosolvents in aqueous humor 95%. For example, for Recipe 1-Solution 1 (Embodiment 1), the ready-to-use solution formulated in this approach contains 0.25 mg/ml FL118, 5% DMSO, 4.76% PG and 90.25% saline. For Recipe 1-Solution 2 (Embodiment 2), the formulated ready-to-use solution contains 0.25 mg/ml FL118, 5% DMSO, 9% PG and 86% saline. For Recipe 5-Solution 1 (Embodiment 3), the formulated ready-to-use solution contains 0.25 mg/ml FL118, 5% DMSO, 2.44% PG, 2.44% PEG 400 and 90.12% saline. For Recipe 6-Solution 1 (Embodiment 4), the formulated ready-to-use solution contains 0.25 mg/ml FL118, 5% DMSO, 4.75% PG, 4.75% HPβCD and about 90.5% saline (here the percentage of saline is not exactly 90.5% because one gram HPβCD does not exactly occupy 1 ml volume; 1 g HPβCD roughly occupies 0.5 ml volume). For Recipe 8-Solution 1 (Embodiment 5), the final formulated solution contains 0.25 mg/ml FL118, 5% DMSO, 2.44% PG, 2.44% PEG 400, 4.75% HPβCD and about 90.47% saline.

From the above representative 5 Embodiments for the formulated ready-to-use solution, both FL118 and DMSO keep consistence at 0.25 mg/ml (FL118) and 5% (DMSO). From these formulation experiments, we found that pH is the key for a water-insoluble drug in the solid phase of the leading solvent (DMSO for the FL118 particular example) to be dissolved into the cosolvent phase. Specifically, in the case of FL118 solvent mixture, a pH<1 adjusted with HCl is required to drive FL118 in the solid phase to be dissolved into the solvent phase. Then, the pH is readjusted back to pH 3-7 with NaOH, which does not cause FL118 to come out from the solvent phase. Generally speaking, the water based solvent mixture that contains a higher percentage of helper cosolvent will be preferred because it could help dissolve more drug to reach a higher concentration. Using FL118 as an example, some of these formulations can reach higher concentrations of FL118 in the formulated solution (the drug formulated in the cosolvent mixture for up to 0.5 mg/ml). In contrast to this, the formulation with Tween 80 (saline 75%+Tween 80 20%+ DMSO 5%) could only reach 0.05 mg/ml of FL118.

Evaluation of the FL118 formulations in animal models described in the foregoing section of the Example exhibits poor outcomes. In particular, the FL118 formulated in the approach described above resulted in not only poor antitumor activity at 1.5 mg/kg with weekly×4 schedules for FL118, but also significantly increased FL118 toxicity to animals. Thus, the extensive testing described above in this Example did not result in formulations that could be used for meaningful evaluation of water-insoluble drugs or drug candidates in animal models of human cancer, and therefore are also not clinically useful.

Example 7

Novel Formulations for Water-Insoluble Drugs or Drug Candidates, Method of Making Thereof, and Method of Using Thereof for Treating Diseases In view of the failure of the extensive testing described in Example 6, we developed three new strategies to make water-insoluble compounds for i.v. injection, which are also suitable for i.p. and p.o. administration. The description of the three strategies to formulate water-insoluble compounds is below. First Approach (Strategy I) to Formulate Water-Insoluble Compounds for i.v. Injection Formulation Components:

The formulation in this strategy comprises a water-insoluble compound, Solvent A, Solvent B, distilled water buffered with or without sodium chloride and/or phosphate in the presence or absence of a low concentration of other helper cosolvents, which are very similar to the components used in the failed formulation experiments described above. Solvent A is selected from μCD, HPβCD or SBEβCD. Solvent B is selected from DMSO or ethanol. Helper solvents are selected from propylene glycol (PG), polyethylene glycol 300 ((PEG 300) or polyethylene glycol 400 (PEG 400). Aqueous humor is distilled water, saline or phosphate-buffered saline.

Formulation Process, and Selection of Solvent Type and Concentration:

1) Make leading solvent solution. Dissolve a Solvent A (βCD, HPβCD or SBEβCD) into a Solvent B (DMSO or ethanol) by gently swirling the solution in a tube for 5-15 minutes at room temperature to form a leading Solvent A/B mixture solution. Which Solvent A (βCD, HPβCD or SBEβCD) is selected to make the leading Solvent A/B mixture solution depends on the chemical property of the water-insoluble compound. Generally speaking, if a compound has acidic group, the Solvent A can be βCD or HPβCD, since they are neutral or basic; if a compound has one or more basic groups, Solvent A can be SBEβCD, since SBEβCD has acidic groups. Which Solvent B (i.e., DMSO or ethanol) to select depends on in which solvent (DMSO or ethanol) the water-insoluble compound dissolves better. For example, testing indicates that FL113 and FL118 poorly dissolve in ethanol but dissolve in DMSO with a low but reasonable concentration (~1 mg/ml). So DMSO is selected as Solvent B for FL113 and FL118 formulation. Solvent A (βCD, HPβCD or SBE-βCD) in the final, ready-to-use formulation solution (W/V) is as low as 0.2% and as high as 5%, which depends on the compound final concentration in the ready-to-use formulated solution. Therefore, the percentage of Solvent A (βCD, HPβCD or SBEβCD) in Solvent B (DMSO or ethanol) is in the range of 2.5% to 50%, which is dependent on the amount of compound that we desire to formulate. 2) Make helper solvent solution. In general, an aqueous humor (distill water, saline or phosphate-buffered saline) is mixed with a helper solvent (PG, PEG 300 or PEG 400) by gently swirling on a swirling apparatus for up to overnight at 25-37° C. These helper solvent solutions include, but are not limited to: Recipe 1 saline (distill water or phosphate-buffered saline) is mixed with PG at 0%, (Helper solvent 1, Hsol-1), 1% (Hsol-2), 2% (Hsol-3), 3% (Hsol-4), 4% (Hsol-5), 5% (Hsol-6), 6% (Hsol-7), 7% (Hsol-8), 8% (Hsol-9), 9% (Hsol-10) and 10% (Hsol-11); Recipe 2 saline (distill water or phosphate-buffered saline) is mixed with PEG 400 (or PEG 300) at 1% (Hsol-1), 2% (Hsol-2), 3% (Hsol-3), 4% (Hsol-4), 5% (Hsol-5), 6% (Hsol-6), 7% (Hsol-7), 8% (Hsol-8), 9% (Hsol-9) and 10% (Hsol-10); and Recipe 3 saline (distill water or phosphate-buffered saline) is mixed with 1% PG/9% PEG 400 (Hsol-1), 2% PG/8% PEG 400 (Hsol-2), 3% PG/7% PEG 400 (Hsol-3), 4% PG/6% PEG 400 (Hsol-4), 5% PG/5% PEG 400 (Hsol-5), 6% PG/4% PEG 400 (Hsol-6), 7% PG/3% PEG 400 (Hsol-7), 8% PG/2% PEG 400 (Hsol-8), 9% PG/1% PEG 400 (Hsol-9). Of note, higher percentage of helper solvents (PG, PEG 300 or PEG 400) can be made but the higher these helper solvents in the ready-to-use formulated solution, the potential more toxic the formulated solution would be. 3) Formulate water-insoluble compounds using both leading solvent solution and helper solvent solution. Dissolve a water-insoluble compound in leading solvent solution (the compound may or may not completely dissolved) by Vortex for 5-15 minutes. Then dilute the drug dissolved in leading solvent solution with helper solvent solution by gently swirling the mixture in a container on a swirling apparatus for 10-20 minutes at room temperature. Using FL118 as an example, in order to make FL118 at a final concentration of 0.5 mg/ml, we can dissolve 1 mg FL118 (as an example, but this can be any amount of FL118, so long as the same ratio is maintained) in 0.1 ml≥5% HPβCD (βCD or SBEβCD) leading solution in DMSO via Vortex for 5 minutes. Then the resultant FL118/HPβCD/DMSO mixture is further diluted in 1.9 ml (20× dilution) in one of the above water-based helper solvent solutions in the above three recipes by gently swirling the tube on a swirling apparatus for 10-20 minutes at room temperature. Specifically, if the resultant FL118/HPβCD/DMSO mixture is further diluted in 1.9 ml Hsol-1 of Recipe 1 to reach a total volume of 2 ml, the final, ready-to-use FL118 formulation solution will be FL118 0.5 mg/ml, HPβCD≥0.25%, DMSO ~5% and PG 0%; if the resultant FL118/HPβCD/DMSO mixture is further diluted in 1.9 ml Hsol-11 of Recipe 1 to reach a total volume of 2 ml, the final, ready-to-use FL118 formulation solution will be FL118 0.5 mg/ml, HPβCD≥0.25%, DMSO ~5% and PG 9.5%). Similarly, in this case, if the resultant FL118/HPβCD/DMSO mixture is further diluted in 1.9 ml Hsol-1 of Recipe 3 to reach a total volume of 2 ml, the final, ready-to-use FL118 formulation solution will be FL118 0.5 mg/ml, HPβCD≥0.25%, DMSO ~5%, PG 0.95% and PEG 400 8.55%; if the resultant FL118/HPβCD/DMSO mixture is further diluted in 1.9 ml Hsol-9 of Recipe 3 to reach a total volume of 2 ml, the final, ready-to-use FL118 formulation solution will be FL118 0.5 mg/ml, HPβCD≥0.25%, DMSO ~5%, PG 8.55% and PEG 400 0.95%. By application of the above formulation process using leading solvent solutions and helper solvent solutions, we are able to successfully formulate individual water-insoluble compounds with diverse chemical structures shown in the FIG. 28 at a broad range of drug concentrations. Again using FL118 as an example, if FL118 at a final concentration of 0.25 mg/ml is desired, we can dissolve 1 mg FL118 (again, as an example, but FL118 can be any amount as long as the same ratio is maintained) in 0.2 ml≥2.5% HPβCD (CD or SBEβCD) solution in DMSO via Vortex for 3-10 minutes. Then the resultant FL118/HPβCD/DMSO mixture is further diluted in 3.8 ml (20× dilution) in one of the above 3 helper solvent solutions to reach a final volume of 4 ml (FL118 0.25 mg/ml, HPβCD≥0.125%, DMSO 5%, water-based helper cosolvents ~95%). If a higher concentration of FL118 for injectable solution with this formulation process is desired, such as a final injectable solution at 1 mg/ml, we can dissolve 2 mg FL118 in 0.1 ml≥20% HPβCD (CD or SBEβCD) solution in DMSO via Vortex for 5-15 minutes. Then the resultant FL118/HPβCD/DMSO mixture is further diluted in 1.9 ml (20× dilution) in one of the above helper solvent solutions to reach a final volume of 2 ml (FL118 1 mg/ml, HPβCD≥0.5%, DMSO ~5%, water-based helper cosolvents ~95%). In conclusion, Strategy I can be used to formulate a chemical compound for i.v. injection (which is inherently compatible for i.p. and p.o. routes) at the desired concentration in preclinical animal model studies or in clinical trials for treatment of patients. The ability to formulate a drug in a wide range of different concentrations in the final, ready-to-use solution is important, because evaluation of a drug either in preclinical animal models or in clinical trials needs a dose escalation from low dose to high dose, while keeping an optimal and consistent volume size—too small volume may produce a larger system error and technical difficulty for drug administration, while too large volume may not be able to practically inject all of the solution to reach the drug dose needed. Additionally, different drug administration routes (i.v., i.p. or p.o.) can be adapted for different volumes.

Second Approach (Strategy II) to Formulate Water-Insoluble Compounds for i.v. Injection In the second approach, after a water-insoluble compound dissolves in the leading Solvent A ((βCD, HPβCD or SBEβCD)/Solvent B (DMSO or ethanol) mixture, one or two helper solvents (PG, PEG 300 or PEG 400) are added to the compound/Solvent A/Solvent B mixture by gently swirling the solution in a tube for up to overnight at 25-37° C. on a swirling apparatus. Then an aqueous humor (distill water, saline or phosphate-buffered saline) is used to dilute the resultant drug solution to a desired concentration and meanwhile, after drug dilution with an aqueous humor the percentage of helper solvents (PG, PEG 300 or PEG 400) in the final, ready-to-use drug formulation solution remains in the range from 1% to 10% in total. Using FL118 as an example, if we formulate FL118 for a final concentration of 0.25 mg/ml with 2% PG, we dissolve 1 mg FL118 (an example, but can be any amount as long as same ratio is used) in 0.2 ml≥2.5% HPβCD (βCD or SBEβCD) solution in DMSO via Vortex for 5-15 minutes. Then add 0.08 ml PG into the resultant FL118/HPβCD/DMSO mixture to mix for up to overnight at 25-37° C. by gently swirling the solution in a tube on a swirling apparatus. The resultant drug solution is further diluted with 3.72 ml aqueous humor (distill water, saline or phosphate-buffered saline) by gently swirling the tube on a swirling apparatus for up to overnight at 25-37° C. to reach a final volume of 4 ml (FL118 0.25 mg/ml, HPβCD≥0.125%, DMSO ~5%, PG 2%). If we formulate a higher concentration of FL118 injectable solution with this approach such as making a final injectable solution at 1 mg/ml with 2% PG and 2% PEG 400, we dissolve 2 mg FL118 (again as an example, but the drug can be provided in any amount as long as the same ratio is used) in 0.1 ml≥10% HPβCD (CD or SBEβCD) solution in DMSO via Vortex for 5-15 minutes. Then add 0.04 ml PG and 0.04 ml PEG 400 into the resultant FL118/HPβCD/DMSO mixture to mix by swirling the solution in a tube for up to overnight at 25-37° C. on a swirling apparatus. The resultant drug solution is further diluted with 1.72 ml aqueous humor (distill water, saline or phosphate-buffered saline) by gently swirling the tube on an apparatus for up to overnight at 25-37° C. to reach a final volume of 2 ml (FL118 1 mg/ml, HPβCD≥0.5%, DMSO ~5%, PG 2%, PEG 400 2%). By using this approach, we are able to make our desired drug formulation solution for i.v. administration (also compatible for i.p. and p.o.).

Third Approach (Strategy III) to Formulate Water-Insoluble Compounds for i.v. Injection In the third approach, after Solvent A (βCD, HPβCD or SBEβCD) is dissolved in Solvent B (DMSO or ethanol), the resultant Solvent A/B mixture is further mixed with one or two helper solvents (PG, PEG 300 or PEG 400) to make a leading master solvent mixture. Then a water-insoluble compound is dissolved in this leading master solvent mixture by gently swirling the solution in a tube for a minimal overnight at 25-37° C. on a swirling apparatus. The water-insoluble compound dissolved in the leading master solvent mixture are then diluted in an aqueous humor (distill water, saline or phosphate-buffered saline) to reach the desired drug concentration by gently swirling the solution in a tube for up to overnight at 25-37° C. on a swirling apparatus. As with Strategy II above, after dilution of the leading master solvent solution with an aqueous humor, the percentage of helper solvents (PG, PEG 300 or PEG 400) in the final, ready-to-use drug formulation solution remains in a range of 1% to 10% in total. Using the same examples described in the Strategy II for FL118 formulation to illustrate, if FL118 is to be formulated at a final concentration of 0.25 mg/ml with 2% PG, we first mix 0.08 ml PG in 0.2 ml≥2.5% HPβCD (CD or SBEβCD) solution in DMSO by gently swirling the solution in appropriate size tube (e.g. 0.5 ml tube) for up to overnight at 25-37° C. on a lab swirling apparatus. Then dissolve 1 mg FL118 in the resultant leading master solvent (HPβCD/DMSO/PG) by gently swirling the solution in the tube for a minimal 16 hours at 25-37° C. on a swirling apparatus. The resultant FL118 solution is further diluted with 3.72 ml aqueous humor (distilled water, saline or phosphate-buffered saline) by gently swirling the solution in a large tube for up to overnight at 25-37° C. on a swirling apparatus to reach a final volume of 4 ml (FL118 0.25 mg/ml, HPβCD≥0.125%, DMSO ~5%, PG 2%). Similarly, if it is desirable to formulate a high concentration of FL118 for use as an injectable solution with this approach, such as making a final injectable solution at 1 mg/ml with 2% PG and 2% PEG 400, we first mix 0.04 ml PG and 0.04 ml PEG 400 in 0.1 ml≥10% HPβCD (CD or SBEβCD) solution in DMSO by gently swirling the solution in a tube for a minimal 16 hours at 25-37° C. on a swirling apparatus. Then dissolve 2 mg FL118 in the resultant leading master solvent (HPβCD/DMSO/PG/PEG 400) by gently swirling the solution in a tube for up to overnight at 25-37° C. on a swirling apparatus. The resultant FL118 solution is further diluted with 1.82 ml aqueous humor (distill water, saline or phosphate-buffered saline) by gently swirling the solution in a tube for up to overnight at 25-37° C. on a swirling apparatus to reach a final volume of 2 ml (FL118 1 mg/ml, HPβCD≥0.5%, DMSO ~5%, PG 2%, PEG 400 2%). By using this approach, we are also able to make desired drug formulation solution for i.v. administration (also compatible for i.p. and p.o.). We found that for the poorly water-insoluble compounds, Strategy II and Strategy III are more effective to dissolve such water-insoluble compounds in an acceptable concentration with better solution stability for i.v. administration. Additionally, when formulating water-insoluble compounds using the three approaches described above, it is preferable that the percentage of DMSO or ethanol remain in a range of percentage from 5% to 10% in the final, ready-to-use drug formulation solution. This can be realized by using different percentages of Solvent A in Solvent B (DMSO or ethanol) in association with appropriate dilution to make the final, ready-to-use drug formulation solution. Alternatively, this could be realized by adding additional Solvent B (DMSO or ethanol) into the leading mater mixture before diluting the leading muster mixture with aqueous humor (distill water, saline or phosphate-buffered saline). Of course, the amount of additional Solvent A (DMSO or ethanol) added in the leading master mixture should be subtracted from the aqueous humor volume for drug dilution. It is also preferable that the molar concentration of Solvent A versus the molar concentration of a compound in the final, ready-to-use formulated solution should be between 1.1-10 (Solvent A molar concentration): 1 (compound molar concentration), which depends on the chemical compound molecular weight, shape and other chemical properties. Generally speaking, a water-insoluble compound with large molecular weight in a non-linear structure needs a higher Solvent A: compound ratio (i.e. need more Solvent A). For a particular water-insoluble compound, this needs to be determined with testing that will be routine for the skilled artisan, given the benefit of the present disclosure. Generally speaking, it is preferable to use helper solvents in low amounts as long as a water-insoluble compound could be dissolved in a state with sufficient stability that could be used for i.v. injection effectively. Comparison of the three formulation strategies described above for water-insoluble compound formulation is summarized in Table 5.

In summary, generally speaking, if the formulation contains helper solvents (PG, PEG 300 or PEG 400) in any one of the three formulation strategies described above, the formulated solution increases drug solution stability. However, the more the helper solvents are in the formulated ready-to-use drug solution, the higher the potential toxicity of the formulated ready-to-use solution is. Therefore, during processing of the formulation strategies described above, it is preferable to test solubility without helper solvents (PG, PEG 300 or PEG 400). Further, it is not necessary for the drug or a drug candidate in the ready-to-use solution to be a true solution, as long as after shaking, the formulated solution shows no precipitation in a reasonable time period, the formulated solution would be qualified for i.v. injection. If additional solubility is desired, the addition of helper solvents (PG, PEG 300 or PEG 400) can be employed, particularly PG, PEG 300 or PEG 400 via the approaches described in Strategy II and Strategy III would obtain better solubility for water-insoluble drug especially for the tough water-insoluble drug. Using FL118 as an example, lack of helper solvents (PG, PEG 300 or PEG 400) in the finally formulated FL118 i.v. injection solution [FL118, Solvent A (HPβCD), Solvent B (DMSO) and aqueous humor (distilled water, saline or phosphate-buffered saline)] decrease the stability of the formulated FL118 solution, however, the formulated ready-to-use FL118 solution without helper solvents (PG, PEG 300 or PEG 400) is still suitable for i.v. injection. Importantly, this formulation of FL118 did not decrease FL118 antitumor activity, while keeping its non-toxic quality. In other words, if a water-insoluble drug or drug candidate formulated using the Strategies I, II and III in the final, ready-to-use solution without helper solvents (PG, PEG 300 or PEG 400) maintains reasonable stability for administration using an i.v. injection procedure, the helper solvents (PG, PEG 300 or PEG 400) can be excluded.

It should be emphasized that the pharmaceutical formulations described above do not have to comprise fully solubulized drug, as long as the water-insoluble drug is not in a solid state. Rather, each compound molecule is dissolved in the final solvent mixture. The water-insoluble compound mixture formulated in the three strategies described above could be semi-transparent or nontransparent clear state with or without a faint color. We find that the formulated water-insoluble drug or drug candidate in most cases is a milk-like or clear cloud solution with or without color after gently re-suspending by swirling. The water-insoluble compound solutions formulated in the three strategies described above are compatible with clinical practice to treat patients or animals with a disease via i.v., i.p. or per oral for single or combinational administration. A comparison of FL118 solutions formulated via the three distinct strategies (Strategy I, Strategy II and Strategy III) described above is summarized in Table 6 above. The FL118 concentration at 0.25 mg/ml, 0.5 mg/ml or 0.75 mg/ml (Table 6) is suitable for i.v. administration to reach a dose escalation from 1 mg/kg to 7.5 mg/kg with a reasonable volume size for i.v. administration for our mouse model system used in this invention. We found that in the case of the FL118 formulations, although the formulated FL118 solution is more stable in the presence of one or two helper solvents (PG and/or PEG 400), the antitumor activity of FL118 shows no clear difference between with and without one or two helper solvents (PG and/or PEG 400). However, i.p. injection of the formulation solution (placebo, vehicle or control solution without FL118) to test the formulation solution toxicity indicated that if larger volumes are required, the formulation solution containing one or two helper solvents (PG and/or PEG 400) tends to be toxic, depending on the percentages of the helper solvent.

Example 8

The Novel Formulations for FL118 Made in the Strategies Described Above Significantly Improve FL118 Maximum Tolerated Dose (MTD) without an Apparent Decrease in FL118 Antitumor Activity As showed in Table 2, by i.p. administration of FL118 formulated in the previous formulation recipe (FL118, 0.05 mg/ml; DMSO, 5%; Tween 80, 20% and saline, 75%,), the MTD in the daily×5 schedule (5 does) is 0.2 mg/kg; the MTD in the day 0, 2 & 4 schedule (3 doses) is 0.5 mg/kg; and the MTD in the schedule of weekly×4 (4 doses) is 1.5 mg/kg. Of further note, FL118 in the daily×5 schedule and the day 0, 2 & 4 schedule (3 doses) fails to reach a drug concentration that produces meaningful antitumor activity in the formulation containing Tween 80. In contrast, the i.v. administration of FL118 in the example new formulation (FL118, 0.5 mg/ml; DMSO, 5%; HPβCD, 0.25% and saline, 95%) significantly increase MTD. Specifically, in the new formulation as shown in FIG. 29, the data from the toxicity (mouse body weight loss) of the daily×5 schedule (d×5, 5 does) for FL118 indicated that the MTD is about 1.5 mg/kg in this schedule (i.e. from 0.2 mg/kg in the old formulation increases to 1.5 mg/kg in this novel formulation); for the every other day on day 0, 2, 4, 6 and 8 schedule (q2×5, 5 doses), the MTD is about 1.5 mg/kg; and for the schedule of weekly×4 (wk×4, 4 doses), the MTD is about 5 mg/kg. Importantly, with the new FL118 MTD dose in the example formulation (FL118, 0.5 mg/ml;

DMSO, 5%; HPβCD, 0.25% and saline, 95%) in the three clinical compatible drug administration schedules (d×5, q2×5 and wk×4) using the most strict drug administration route (i.v.), FL118 effectively inhibits tumor growth and even appears to result in a cure (FIG. 30 A), while control mice without FL118 treatment grow tumor to the maximal size allowed by the IACUC (Institute Animal Care and Use Committee) in two weeks (FIG. 30 B,C,D,E,F,G). These exciting results appear not only in head & neck cancer (FaDu) (FIG. 30), but also in colon cancer (SW620) (FIG. 31) and mesothelioma cancer (211H, H226), a specialized lung cancer (FIG. 32). Of note, i.v. administration of selected FL118 solution formulated in the Strategy II or Strategy III shown in Table 6 that contains FL118, 0.75 mg/ml; DMSO, 5%; HPβCD, 0.375%, PG, 5%; PEG 400, 5% and saline, 85%, obtains antitumor effects similar to those shown in the FIGS. 30-32 with the FL118 solution without helper solvents (PG and PEG 400).

Advantages and Improvements of the Invention Over Existing Methods

In view of the foregoing, it will be recognized by those skilled in the art that FL118 has not been previously recognized as a highly effective antitumor compound, nor has its MOA for cancer treatment. Accordingly, this invention has, for the first time, discovered 1) in the formulation (0.05 mg/ml FL118, 75% saline, 20% Tween 80, 5% DMSO) for i.p. injection, exceptional and unexpected superior antitumor efficacy of FL118 for its use in an interval schedule, such as weekly or biweekly but not frequent administration, such as daily, to maximize its antitumor activity potential and minimize its toxicity to normal tissues; 2) in the formulation (0.25-1 mg/ml FL118, 95% saline, 0.125-0.5% HPβCD, 5% DMSO) for injectable and oral administration, exceptional and unexpectedly superior antitumor efficacy of FL118 was observed for its use in an interval schedule, such as daily for five times, every other day for five times, weekly for four times to maximize its antitumor activity potential and minimize its toxicity to normal tissues; 3) Due to its unique MOA, FL118 is suitable for use in combination therapy with many other classic chemotherapeutic and chemopreventive agents to further enhance its antitumor potential; 4) In contrast to using a high dose of AITC or selenium compounds to enhance chemotherapeutic drug efficacy (although exhibiting some effectiveness), we provide data suggesting that creation of a AITC or selenium deficiency via consumption of AITC and selenium-free foods during chemotherapy could surprisingly enhance the antitumor potential of chemotherapeutic drugs, including FL118, which could avoid the potential complexity for therapeutic drugs in combination with AITC or its related compounds and/or selenium; 5) we are the first to consider FL118 formulation for injectable and oral administration. We discovered multiple novel recipes which can be made by three approaches (Strategy I, Strategy II, Strategy III) to increase its efficacy, and in so doing, discovered method to formulate water-insoluble drug and drug candidates; and 6) we disclose the MOA for FL118 which results in selectively inhibiting expression of multiple IAP/Bcl-2 family antiapoptotic proteins and cancer cell survival Akt signaling, while increasing the expression of selective Bcl-2 family proapoptotic proteins. It is believed that all of these in vitro or in vivo effects were previously unknown.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

We claim:

1. A method for inhibiting the growth of cancer in an individual comprising administering to the individual a pharmaceutical preparation comprising 0.125-0.5% hydroxypropyl-β-cyclodextrin, 5%-10% dimethyl sulfoxide, and an effective amount of 10H-1,3-Dioxolo[4,5-g]pyrano[3',4':6,7]indolizino[1,2-b]quinoline-8,11(7H,12H)-dione, 7-ethyl-7-hydroxy-, (S)- ("FL118"), wherein the effective amount of FL118 is 0.25 mg/ml-5.0 mg/ml, such that growth of the cancer in the individual is inhibited subsequent to the administration.

2. The method of claim 1, wherein the pharmaceutical preparation is administered intravenously, orally or intraperitoneally.

3. The method of claim 1, wherein the pharmaceutical preparation comprises 1-10% polar aprotic solvent.

4. The method of claim 1, wherein the pharmaceutical comprises 0.25-1 mg/ml FL118, 0.125-0.5% hydroxypropyl-β-cyclodextrin, and 5% dimethyl sulfoxide.

5. The method of claim 1, wherein pharmaceutical preparation comprises at least one additional anti-cancer compound.

6. A pharmaceutical preparation comprising an aqueous solution comprising 0.25 mg/ml-5.0 mg/ml 10H-1,3-Dioxolo[4,5-g]pyrano[3',4':6,7]indolizino[1,2-b]quinoline-8,11(7H,12H)-dione, 7-ethyl-7-hydroxy-, (S)- ("FL118"), 0.125-0.5% hydroxypropyl-β-cyclodextrin, and 5-10% dimethyl sulfoxide.

7. The pharmaceutical preparation of claim 6, wherein the pharmaceutical preparation comprises at least one additional anti-cancer compound.

8. A method for preparing a water-insoluble drug formulation for intravenous (i.v.) administration that is suitable for intraperitoneal (i.p.) and oral (p.o.) administration comprising providing a Solvent A and a Solvent B, dissolving the Solvent A in the Solvent B to make a leading Solvent A/Solvent B mixture, and then dissolving a water-insoluble compound in the Solvent A/Solvent B mixture wherein the Solvent A is selected from the group consisting of β cyclodextrin (βCD), hydroxypropyl-β-cyclodextrin (HPβCD) and sulfobutylether-β-cyclodextrin (SBEβCD), and combinations thereof, and the Solvent B is selected from the group consisting of dimethyl sulfoxide (DMSO) and ethanol.

9. The method of claim 8, wherein the water-insoluble compound is dissolved in the leading Solvent A/Solvent B mixture and then diluted with an aqueous humor selected from the group consisting of distilled water, saline or phosphate-buffered saline, or combinations thereof, with 0-10% one or two Helper Solvents to the desired drug concentration for disease treatment by administrating the resulting solution intravenously, orally or intraperitoneally wherein the Helper Solvents are selected from the group consisting propylene glycol (PG), polyethylene glycol 300 (PEG 300) and polyethylene 400 (PEG 400), and combinations thereof.

10. The method of claim 8, wherein the leading Solvent A/Solvent B mixture comprises one or two Helper Solvents to make a leading master solution mixture, the method further comprising dissolving the water-insoluble compound in the leading master solution mixture, and diluting the leading master solution mixture comprising the water-insoluble compound with an aqueous humor selected from the group consisting of distilled water, saline, phosphate-buffered saline, or combinations thereof, to provide a ready-to-use drug formulation solution with a desired drug concentration, wherein the ready-to-use drug formulation contains up to 10% of the Helper Solvent, wherein the ready-to-use drug formulation is suitable for disease treatment by administrating the ready-to-use drug formulation intravenously, orally or intraperitoneally.

11. The method of claim 8, wherein the water-insoluble compound is dissolved in the leading Solvent A/Solvent B mixture, wherein the leading Solvent A/Solvent B mixture comprising the water-insoluble compound is then supplied with one or two Helper Solvents to make a leading master solution mixture, wherein the leading master solution mixture comprising the water-insoluble compound is diluted with an aqueous humor selected from the group consisting of distilled water, saline, phosphate-buffered saline, or combinations thereof, to provide a ready-to-use drug formulation solution which comprises up to 10% Helper Solvent, wherein the ready-to-use drug formulation solution is suitable for disease treatment by administrating the formulated solution intravenously, orally or intraperitoneally.

* * * * *